US012615909B2

(12) United States Patent
Yoshiyasu et al.

(10) Patent No.: US 12,615,909 B2
(45) Date of Patent: Apr. 28, 2026

(54) LIGHT-EMITTING DEVICE AND LIGHT-EMITTING APPARATUS

(71) Applicant: Semiconductor Energy Laboratory Co., Ltd., Kanagawa-ken (JP)

(72) Inventors: Yui Yoshiyasu, Atsugi (JP); Sachiko Kawakami, Atsugi (JP); Naoaki Hashimoto, Sagamihara (JP); Tsunenori Suzuki, Yokohama (JP); Satoshi Seo, Sagamihara (JP)

(73) Assignee: Semiconductor Energy Laboratory Co., Ltd. (JP)

(*) Notice: Subject to any disclaimer, the term of this patent is extended or adjusted under 35 U.S.C. 154(b) by 946 days.

(21) Appl. No.: 17/851,288

(22) Filed: Jun. 28, 2022

(65) Prior Publication Data

US 2023/0025460 A1 Jan. 26, 2023

(30) Foreign Application Priority Data

Jun. 30, 2021 (JP) ................................ 2021-109302

(51) Int. Cl.
*H10K 50/16* (2023.01)
*C07D 401/14* (2006.01)
(Continued)

(52) U.S. Cl.
CPC ......... *H10K 50/166* (2023.02); *C07D 401/14* (2013.01); *C07D 403/10* (2013.01);
(Continued)

(58) Field of Classification Search
CPC ........................... H10K 50/166; H10K 50/844
See application file for complete search history.

(56) References Cited

U.S. PATENT DOCUMENTS 5,953,985 A 9/1999 Kobayashi
6,120,338 A 9/2000 Hirano et al.
(Continued)

FOREIGN PATENT DOCUMENTS

JP 2000-036385 A 2/2000
JP 2003-059663 A 2/2003
(Continued)

OTHER PUBLICATIONS

Lamprecht, B. et al., "Organic Optoelectronic Device Fabrication Using Standard UV Photolithography," Physica Status Solidi. Rapid Research Letters, Oct. 30, 2007, vol. 2, No. 1, pp. 16-18.
(Continued)

*Primary Examiner* — Sean M DeGuire
(74) *Attorney, Agent, or Firm* — Husch Blackwell LLP

(57) ABSTRACT

A light-emitting device with high resistance to heat in a fabrication process is provided. The light-emitting device includes an EL layer between an anode and a cathode. The EL layer includes at least a light-emitting layer and an electron-transport layer that includes a first electron-transport layer in contact with the light-emitting layer and a second electron-transport layer in contact with the first electron-transport layer. The first electron-transport layer includes a first heteroaromatic compound including at least one heteroaromatic ring. The second electron-transport layer includes a second heteroaromatic compound that includes at least one heteroaromatic ring and is different from the first heteroaromatic compound. The first heteroaromatic compound has a difference of 20° C. or less between the crystallization temperature (Tpc) of a powder state and the crystallization temperature (Ttc) of a thin film state. The second heteroaromatic compound has a difference of 100° C. or less between Tpc and Ttc.

13 Claims, 24 Drawing Sheets

100

(51) Int. Cl.

| | |
|---|---|
| ***C07D 403/10*** | (2006.01) |
| ***C07D 403/14*** | (2006.01) |
| ***C07D 409/10*** | (2006.01) |
| ***C07D 471/04*** | (2006.01) |
| ***C07D 491/048*** | (2006.01) |
| ***C07D 519/00*** | (2006.01) |
| ***C07F 7/22*** | (2006.01) |
| ***C07F 15/00*** | (2006.01) |
| ***H10K 50/17*** | (2023.01) |
| ***H10K 85/30*** | (2023.01) |
| ***H10K 85/60*** | (2023.01) |

(52) U.S. Cl.
CPC ......... *C07D 403/14* (2013.01); *C07D 409/10* (2013.01); *C07D 471/04* (2013.01); *C07D 491/048* (2013.01); *C07D 519/00* (2013.01); *C07F 7/2284* (2013.01); *C07F 15/0093* (2013.01); *H10K 50/171* (2023.02); *H10K 85/30* (2023.02); *H10K 85/346* (2023.02); *H10K 85/654* (2023.02); *H10K 85/656* (2023.02); *H10K 85/657* (2023.02); *H10K 85/6572* (2023.02); *H10K 85/6576* (2023.02)

(56) References Cited

U.S. PATENT DOCUMENTS

| | | | | |
|---|---|---|---|---|
| 8,358,057 | B2 | 1/2013 | Oota | |
| 10,476,009 | B2 | 11/2019 | Yamada et al. | |
| 2002/0072139 | A1 | 6/2002 | Kashiwabara | |
| 2008/0238297 | A1 | 10/2008 | Oota | |
| 2011/0148290 | A1 | 6/2011 | Oota | |
| 2012/0256204 | A1 | 10/2012 | Yoshizumi et al. | |
| 2012/0273804 | A1 | 11/2012 | Hatano | |
| 2012/0276484 | A1 | 11/2012 | Izumi et al. | |
| 2013/0084531 | A1 | 4/2013 | Hamaguchi et al. | |
| 2013/0084664 | A1 | 4/2013 | Yoshitoku et al. | |
| 2013/0084666 | A1 | 4/2013 | Oshige | |
| 2013/0280839 | A1 | 10/2013 | Sonoda et al. | |
| 2013/0295705 | A1 | 11/2013 | Sonoda et al. | |
| 2014/0004640 | A1 | 1/2014 | Hamaguchi et al. | |
| 2014/0004642 | A1 | 1/2014 | Otsuka et al. | |
| 2015/0060826 | A1 | 3/2015 | Matsumoto. et al. | |
| 2015/0069360 | A1 | 3/2015 | Sato | |
| 2015/0076476 | A1 | 3/2015 | Odaka et al. | |
| 2016/0075718 | A1 | 3/2016 | Mitsumori et al. | |
| 2016/0172595 | A1 | 6/2016 | Malinowski et al. | |
| 2016/0240794 | A1 * | 8/2016 | Yamada ............... | H10K 85/626 |
| 2016/0315133 | A1 | 10/2016 | Sato | |
| 2017/0141167 | A1 | 5/2017 | Naganuma | |
| 2017/0256754 | A1 | 9/2017 | Defranco et al. | |
| 2018/0190908 | A1 | 7/2018 | Ke et al. | |
| 2020/0203662 | A1 | 6/2020 | Mollard et al. | |
| 2021/0363151 | A1 * | 11/2021 | Seo .................... | H10K 85/6576 |
| 2022/0077397 | A1 | 3/2022 | Hashimoto et al. | |

FOREIGN PATENT DOCUMENTS

| | | | | |
|---|---|---|---|---|
| JP | 2008-098106 A | 4/2008 | | |
| JP | 2008-147072 A | 6/2008 | | |
| JP | 2008-251270 A | 10/2008 | | |
| JP | 2012-160473 A | 8/2012 | | |
| JP | 2014-120218 A | 6/2014 | | |
| JP | 2014-135251 A | 7/2014 | | |
| JP | 2014-232568 A | 12/2014 | | |
| JP | 2015-115178 A | 6/2015 | | |
| JP | 2016-197494 A | 11/2016 | | |
| JP | 2019-179696 A | 10/2019 | | |
| JP | 2020-160305 A | 10/2020 | | |
| WO | WO-2019229583 A1 * | 12/2019 | ............. | C09K 11/06 |

OTHER PUBLICATIONS

Zakhidov, A. et al., "Orthogonal Processing: A New Strategy for Organic Electronics," Chemical Science, Apr. 7, 2011, vol. 2, No. 6, pp. 1178-1182.

Malinowski, P. et al., "High Resolution Photolithography for Direct View Active Matrix Organic Light-Emitting Diode Augmented Reality Displays," Journal of the Society for Information Display, Apr. 2, 2018, vol. 26, No. 3, pp. 128-136.

Malinowski, P. et al., "Photolithographic Patterning of Organic Photodetectors with a Non-Fluorinated Photoresist System," Organic Electronics, Jul. 12, 2014, vol. 15, No. 10, pp. 2355-2359.

Malinowski, P. et al., "Multicolor 1250 ppi OLED Arrays Patterened by Photolithography," SID Digest '16: SID International Symposium Digest of Technical Papers, May 22, 2016, vol. 47, No. 1, pp. 1009-1012.

Papadopoulos, N. et al., "AMOLED Displays with In-Pixel Photodetector," Liquid Crystals and Display Technology, Jul. 9, 2020, pp. 1-19.

Ke, T. et al., "Technology Developments in High-Resolution FMM-free OLED and BEOL IGZO TFTs for Power-Efficient Microdisplays," SID Digest '21: SID International Symposium Digest of Technical Papers, May 1, 2021, vol. 52, No. 1, pp. 127-130.

Malinowski, P. et al., "Integration of Additional Functionalities into the Frontplane of AMOLED Displays," SID Digest '20: SID International Symposium Digest of Technical Papers, Aug. 1, 2020, vol. 51, No. 1, pp. 646-649.

Malinowski, P. et al., "Organic Photolithography for Displays with Integrated Fingerprint Scanner," SID Digest '19: SID International Symposium Digest of Technical Papers, May 29, 2019, vol. 50, No. 1, pp. 1007-1010.

Ke, T. et al., "Island and Hole Fabrication on OLED Stack for High-Resolution Sensor in Display Application," IDW '20: Proceedings of the 27th International Display Workshops, Dec. 9, 2020, vol. 27, pp. 902-905.

Gather, M. et al., "Solution-Processed Full-Color Polymer-OLED Displays Fabricated by Direct Photolithography," SID Digest '06: SID International Symposium Digest of Technical Papers, Jun. 1, 2006, vol. 37, No. 1, pp. 909-911.

Malinowski, P. et al., "Photolithography as Enabler of AMOLED Displays Beyond 1000 ppi," SID Digest '17: SID International Symposium Digest of Technical Papers, May 1, 2017, vol. 48, No. 1, pp. 623-626.

Roth.C, "Polymers under nanoconfinement: where are we now in understanding local property changes?," Chem. Soc. Rev. (Chemical Society Reviews), Jun. 4, 2021, vol. 50, No. 14, pp. 8050-8066.

* cited by examiner

Sample 1 <Structure> Glass\NBPhen (10 nm)

Sample 2 <Structure> Glass\2mpPCBPDBq (10 nm)

Sample 3 <Structure> Glass\8BP-4mDBtPBfpm (10 nm)

Sample 4 <Structure> Glass\6,6'(P-Bqn)2BPy (10 nm)

Sample 5 <Structure> Glass\2mpPCBPDBq (10 nm)\NBPhen (10 nm)

Sample 6 <Structure> 8BP-4mDBtPBfpm (10 nm)\6,6'(P-Bqn)2BPy (10 nm)

Sample 7 <Structure> 8BP-4mDBtPBfpm (10 nm)\NBPhen (10 nm)

LIGHT-EMITTING DEVICE AND LIGHT-EMITTING APPARATUS

BACKGROUND OF THE INVENTION

1. Field of the Invention

One embodiment of the present invention relates to a light-emitting device, a light-emitting apparatus, a light-emitting and light-receiving apparatus, an electronic appliance, a lighting device, and an electronic device. Note that one embodiment of the present invention is not limited to the above technical field. The technical field of one embodiment of the present invention disclosed in this specification and the like relates to an object, a method, or a manufacturing method. One embodiment of the present invention relates to a process, a machine, manufacture, or a composition of matter. Specifically, examples of the technical field of one embodiment of the present invention disclosed in this specification include a semiconductor device, a display device, a light-emitting apparatus, a lighting device, a memory device, an imaging device, a driving method thereof, and a manufacturing method thereof.

2. Description of the Related Art

Light-emitting devices (organic EL devices) including organic compounds and utilizing electroluminescence (EL) have been put to practical use. In the basic structure of such light-emitting devices, an organic compound layer containing a light-emitting material (an EL layer) is interposed between a pair of electrodes. Carriers are injected by application of voltage to the device, and recombination energy of the carriers is used, whereby light emission can be obtained from the light-emitting material.

Such light-emitting devices are of self-luminous type and thus have advantages over liquid crystal devices, such as high visibility and no need for backlight when used in pixels of a display, and are suitable as flat panel display devices. Displays including such light-emitting devices are also highly advantageous in that they can be thin and lightweight. Moreover, such light-emitting devices also have a feature that response speed is extremely fast.

Since light-emitting layers of such light-emitting devices can be successively formed two-dimensionally, planar light emission can be achieved. This feature is difficult to realize with point light sources typified by incandescent lamps and LEDs or linear light sources typified by fluorescent lamps; thus, the light-emitting devices also have great potential as planar light sources, which can be used for lighting devices and the like.

Displays or lighting devices including light-emitting devices can be used suitably for a variety of electronic appliances as described above, and research and development of light-emitting devices has progressed for more favorable characteristics.

A variety of methods for manufacturing light-emitting devices are known. As a method for manufacturing a high-resolution light-emitting device, a method of forming a light-emitting layer without using a fine metal mask is known. An example of the method is a method for manufacturing an organic EL display described in Patent Document 1. The method includes a step of forming a first light-emitting layer as a continuous film crossing a display region including an electrode array by deposition of a first luminescent organic material containing a mixture of a host material and a dopant material over the electrode array that is formed over an insulating substrate and includes a first pixel electrode and a second pixel electrode; a step of irradiating part of the first light-emitting layer positioned over the second pixel electrode with ultraviolet light while part of the first light-emitting layer positioned over the first pixel electrode is not irradiated with ultraviolet light; a step of forming a second light-emitting layer as a continuous film crossing the display region by deposition of a second luminescent organic material, which contains a mixture of a host material and a dopant material but differs from the first luminescent organic material, over the first light-emitting layer; and a step of forming a counter electrode over the second light-emitting layer.

Non-Patent Document 1 discloses a fabrication method of an organic optoelectronic device using standard UV photolithography, as one of an organic EL device (Non-Patent Document 1).

REFERENCES

Patent Document

[Patent Document 1] Japanese Published Patent Application No. 2012-160473

Non-Patent Document

[Non-Patent Document 1] B. Lamprecht et al., "Organic optoelectronic device fabrication using standard UV photolithography" phys. stat. sol. (RRL) 2, No. 1, pp. 16-18 (2008)

SUMMARY OF THE INVENTION

An object of one embodiment of the present invention is to provide a light-emitting device with high heat resistance. Another object of one embodiment of the present invention is to provide a light-emitting device with high resistance to heat in a fabrication process. Another object of one embodiment of the present invention is to provide a highly reliable light-emitting device. Another object of one embodiment of the present invention is to provide a light-emitting device, a light-emitting apparatus, an electronic appliance, a display device, and an electronic device each having low power consumption. Another object of one embodiment of the present invention is to provide a light-emitting device, a light-emitting apparatus, an electronic appliance, a display apparatus, and an electronic device each having low power consumption and high reliability.

Note that the description of these objects does not preclude the existence of other objects. One embodiment of the present invention does not necessarily achieve all the objects listed above. Other objects will be apparent from and can be derived from the description of the specification, the drawings, the claims, and the like.

One embodiment of the present invention is a light-emitting device including an EL layer between an anode and a cathode. The EL layer includes at least a light-emitting layer and an electron-transport layer. The electron-transport layer includes a first electron-transport layer in contact with the light-emitting layer and a second electron-transport layer in contact with the first electron-transport layer. The first electron-transport layer includes a first heteroaromatic compound including at least one heteroaromatic ring. The second electron-transport layer includes a second heteroaromatic compound that includes at least one heteroaromatic ring and is different from the first heteroaromatic compound.

The first heteroaromatic compound has a difference less than or equal to 20° C. between a crystallization temperature (Tpc) of a powder state and a crystallization temperature (Ttc) of a thin film state. The second heteroaromatic compound has a difference less than or equal to 100° C. between a crystallization temperature (Tpc) of a powder state and a crystallization temperature (Ttc) of a thin film state.

The above-described crystallization temperature (Tpc) of a powder state refers to the crystallization temperature obtained by thermal analysis (differential scanning calorimetry) of the powder (solid) of an organic compound.

In this specification, the above-described crystallization temperature (Ttc) of a thin film state is defined as the temperature at which change in film quality is observed in a thin film formed by evaporation of the powder (solid) of the organic compound. The change in film quality turns the color of the whole or part of the transparent film to white (or any other color included in a material), resulting in lower transparency. This state is observed with a microscope or the like to determine the temperature at which the film quality changes.

In the above structure, the heteroaromatic ring preferably includes any one of a pyridine ring, a diazine ring, a triazine ring, and a polyazole ring.

In the above structure, the heteroaromatic ring preferably includes a fused heteroaromatic ring having a fused ring structure.

In the above structure, the fused heteroaromatic ring is preferably any one of a quinoline ring, a benzoquinoline ring, a quinoxaline ring, a dibenzoquinoxaline ring, a quinazoline ring, a benzoquinazoline ring, a dibenzoquinazoline ring, a phenanthroline ring, a furodiazine ring, and a benzimidazole ring.

In the above structure, the heteroaromatic ring is preferably any one of a pyrimidine ring, a pyrazine ring, a pyridazine ring, a triazine ring, a pyridine ring, a phenanthroline ring, a quinoxaline ring, a dibenzoquinoxaline ring, a quinazoline ring, a benzoquinazoline ring, a dibenzoquinazoline ring, a benzimidazole ring, a benzofropyrimidine ring, and a benzofropyrazine ring.

In addition to the aforementioned light-emitting device, the present invention includes a light-emitting device including a layer (e.g., a cap layer) that is in contact with an electrode and contains an organic compound.

Another embodiment of the present invention is a light-emitting apparatus including any of the above-described light-emitting devices, and a transistor or a substrate.

Another embodiment of the present invention is a light-emitting apparatus including a first light-emitting device and a second light-emitting device that are adjacent to each other. The first light-emitting device includes a second electrode over a first electrode with a first EL layer between the first electrode and the second electrode. The first EL layer includes at least a first light-emitting layer, a first electron-transport layer, a second electron-transport layer, and a first electron-injection layer. The first electron-transport layer and the second electron-transport layer are over the first light-emitting layer. A first insulating layer is in contact with a side surface of the first light-emitting layer, a side surface of the first electron-transport layer, and a side surface of the second electron-transport layer. The first electron-injection layer is over the second electron-transport layer. The first insulating layer is positioned between the first electron-injection layer and the side surface of the first light-emitting layer, the side surface of the first electron-transport layer, and the side surface of the second electron-transport layer. The second light-emitting device includes the second electrode over a third electrode with a second EL layer between the second electrode and the third electrode. The second EL layer includes at least a second light-emitting layer, a third electron-transport layer, a fourth electron-transport layer, and a second electron-injection layer. The third electron-transport layer and the fourth electron-transport layer are over the second light-emitting layer. A second insulating layer is in contact with a side surface of the second light-emitting layer, a side surface of the third electron-transport layer, and a side surface of the fourth electron-transport layer. The first electron-injection layer is over the fourth electron-transport layer. The second insulating layer is positioned between the first electron-injection layer and the side surface of the second light-emitting layer, the side surface of the third electron-transport layer, and the side surface of the fourth electron-transport layer. The first electron-transport layer and the third electron-transport layer each include a first heteroaromatic compound including at least one heteroaromatic ring. The second electron-transport layer and the fourth electron-transport layer each include a second heteroaromatic compound that includes at least one heteroaromatic ring and is different from the first heteroaromatic compound. The first heteroaromatic compound has a difference less than or equal to 20° C. between a crystallization temperature (Tpc) of a powder state and a crystallization temperature (Ttc) of a thin film state. The second heteroaromatic compound has a difference less than or equal to 100° C. between a crystallization temperature (Tpc) of a powder state and a crystallization temperature (Ttc) of a thin film state.

In the above structure, the heteroaromatic ring preferably includes any one of a pyridine skeleton, a diazine skeleton, a triazine skeleton, and a polyazole skeleton.

In the above structure, the heteroaromatic ring preferably includes a fused heteroaromatic ring having a fused ring structure.

In the above structure, the fused heteroaromatic ring is preferably any one of a quinoline ring, a benzoquinoline ring, a quinoxaline ring, a dibenzoquinoxaline ring, a quinazoline ring, a benzoquinazoline ring, a dibenzoquinazoline ring, a phenanthroline ring, a furodiazine ring, and a benzimidazole ring.

Another embodiment of the present invention is an electronic appliance including the light-emitting apparatuses having any of the above structures and a sensor unit, an input unit, or a communication unit.

Another embodiment of the present invention is a lighting device including the light-emitting apparatuses having any of the above structures and a housing.

The scope of one embodiment of the present invention includes a light-emitting apparatus or a light-emitting and light-receiving apparatus including a light-emitting device, and a lighting device including the light-emitting apparatus or the light-emitting and light-receiving apparatus. Accordingly, the light-emitting apparatus or the light-emitting and light-receiving apparatus in this specification refers to an image display device and a light source (including a lighting device). In addition, the light-emitting apparatus or the light-emitting and light-receiving apparatus includes the following in its category: a module in which a connector such as a flexible printed circuit (FPC) or a tape carrier package (TCP) is attached to a light-emitting apparatus; a module in which a printed wiring board is provided at the end of a TCP; and a module in which an integrated circuit (IC) is directly mounted on a light-emitting device by a chip on glass (COG) method.

In this specification, the terms "source" and "drain" of a transistor interchange with each other depending on the polarity of the transistor or the levels of potentials applied to the terminals. In general, in an n-channel transistor, a terminal to which a lower potential is applied is called a source, and a terminal to which a higher potential is applied is called a drain. In a p-channel transistor, a terminal to which a lower potential is applied is called a drain, and a terminal to which a higher potential is applied is called a source. In this specification, the connection relation of a transistor is sometimes described assuming for convenience that the source and the drain are fixed; in reality, the names of the source and the drain interchange with each other depending on the relation of the potentials.

In this specification, a source of a transistor means a source region that is part of a semiconductor film functioning as an active layer or a source electrode connected to the semiconductor film. Similarly, a drain of a transistor means a drain region that is part of the semiconductor film or a drain electrode connected to the semiconductor film. A "gate" means a gate electrode.

In this specification, a state in which transistors are connected to each other in series means, for example, a state in which only one of a source and a drain of a first transistor is connected to only one of a source and a drain of a second transistor. In addition, a state in which transistors are connected in parallel means a state in which one of a source and a drain of a first transistor is connected to one of a source and a drain of a second transistor and the other of the source and the drain of the first transistor is connected to the other of the source and the drain of the second transistor.

In this specification, connection means electrical connection and corresponds to a state where current, voltage, or a potential can be supplied or transmitted. Accordingly, a state of being connected means not only a state of being directly connected but also a state of being indirectly connected through a circuit element such as a wiring, a resistor, a diode, or a transistor that allows a current, a voltage, or a potential to be supplied or transmitted.

In this specification, even when independent components are connected to each other in a circuit diagram, there is actually a case where one conductive film has functions of a plurality of components, such as a case where part of a wiring serves as an electrode. Connection in this specification also includes such a case where one conductive film has functions of a plurality of components, in its category.

An embodiment of the present invention can provide a light-emitting device with high heat resistance. Another embodiment of the present invention can provide a light-emitting device with high resistance to heat in a fabrication process. Another embodiment of the present invention can provide a highly reliable light-emitting device. Another embodiment of the present invention can provide a light-emitting device, a light-emitting apparatus, an electronic appliance, a display device, and an electronic device each having low power consumption. Another embodiment of the present invention can provide a light-emitting device, a light-emitting apparatus, an electronic appliance, a display apparatus, an electronic device, and a lighting device each having low power consumption and high reliability.

Note that the description of these effects does not preclude the existence of other effects. One embodiment of the present invention does not necessarily have all the effects listed above. Other effects will be apparent from and can be derived from the description of the specification, the drawings, the claims, and the like.

DETAILED DESCRIPTION OF THE INVENTION

Embodiments of the present invention will be described in detail below with reference to the drawings. Note that the present invention is not limited to the following description, and it will be readily appreciated by those skilled in the art that modes and details of the present invention can be modified in various ways without departing from the spirit and scope of the present invention. Therefore, the present invention should not be construed as being limited to the description in the following embodiments.

Embodiment 1

In this embodiment, a light-emitting device of one embodiment of the present invention is described. With a device structure described in this embodiment, the light-emitting device can have properties that are hardly affected by a step including thermal treatment in the fabrication process; a so-called highly heat-resistant light-emitting device can be provided.

Figure 1A:
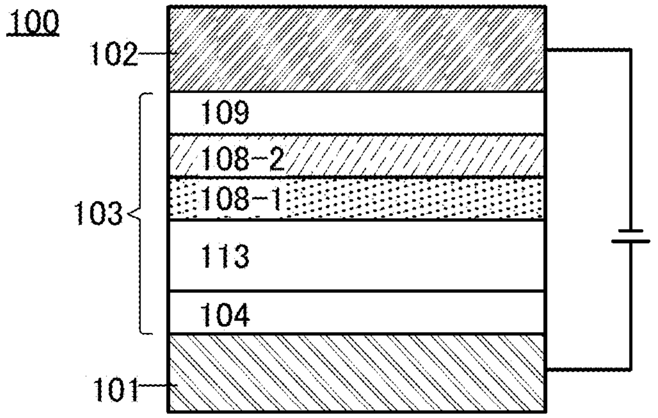
FIGS. 1A to 1C illustrate structures of light-emitting devices of an embodiment.

FIG. 1A illustrates a structure of a light-emitting device 100 of one embodiment of the present invention. As illustrated in FIG. 1A, the light-emitting device 100 includes a first electrode 101, a second electrode 102, and an EL layer 103 between the first electrode 101 and the second electrode 102. In the EL layer 103, a hole-injection/transport layer 104, a light-emitting layer 113, a first electron-transport layer 108-1, a second electron-transport layer 108-2, and an electron-injection layer 109 are sequentially stacked. Thus, the electron-transport layer of the light-emitting device 100 has a structure in which the first electron-transport layer 108-1 and the second electron-transport layer 108-2 are stacked.

The first electron-transport layer 108-1 includes a heteroaromatic compound including at least one heteroaromatic ring. Note that the heteroaromatic compound is included in an organic compound. For the heteroaromatic compound used for the first electron-transport layer 108-1, the difference between the crystallization temperature (Tpc) of the powder state and the crystallization temperature (Ttc) of the thin film state is preferably less than or equal to 20° C.

The second electron-transport layer 108-2 includes at least one heteroaromatic ring and a heteroaromatic compound that is different from the heteroaromatic compound used for the first electron-transport layer 108-1. For the heteroaromatic compound used for the second electron-transport layer 108-2, the difference between the crystallization temperature (Tpc) of the powder state and the crystallization temperature (Ttc) of the thin film state is preferably less than or equal to 100° C.

The heteroaromatic ring includes any one of a pyridine ring, a diazine ring, a triazine ring, a polyazole ring, and the like. Note that examples of the above-described diazine ring include a pyrimidine ring, a pyrazine ring, and a pyridazine ring. The heteroaromatic ring includes a fused heteroaromatic ring having a fused ring structure.

Examples of the fused heteroaromatic ring include a quinoline ring, a benzoquinoline ring, a quinoxaline ring, a dibenzoquinoxaline ring, a quinazoline ring, a benzoquinazoline ring, a dibenzoquinazoline ring, a phenanthroline ring, a benzofurodiazine ring (for example, a benzofuropyrimidine ring or a benzofuropyrazine ring), and a benzimidazole ring. Note that a quinoline ring, a benzoquinoline ring, and a phenanthroline ring each include a structure of a pyridine ring, for example. In addition, a quinoxaline ring, a dibenzoquinoxaline ring, and a benzofuropyrazine ring each include a structure of a pyrazine ring. Furthermore, a quinazoline ring, a benzoquinazoline ring, a dibenzoquinazoline ring, and a benzofuropyrimidine ring each include a structure of a pyrimidine ring.

As specific examples of the above heteroaromatic compound including a heteroaromatic ring or the above heteroaromatic compound including a fused heteroaromatic ring, the materials having the difference between the crystallization temperature (Tpc) of the powder state and the crystallization temperature (Ttc) of the thin film state in the above ranges, among the materials described in Embodiment 2, can be used in appropriate combination for the first electron-transport layer 108-1 and the second electron-transport layer 108-2.

As long as the above temperature conditions are satisfied, one or more kinds of heteroaromatic compounds represented by Structural Formulae (101) to (116) can be used alone or in combination as the heteroaromatic compound for the first electron-transport layer 108-1 or the second electron-transport layer 108-2.

[Chemical Formula 1]

(101)

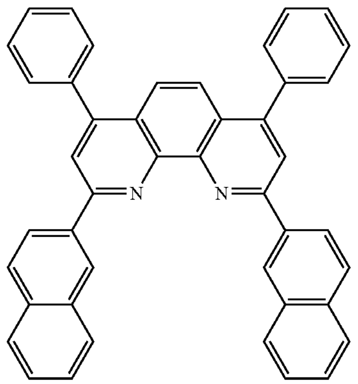

(102)

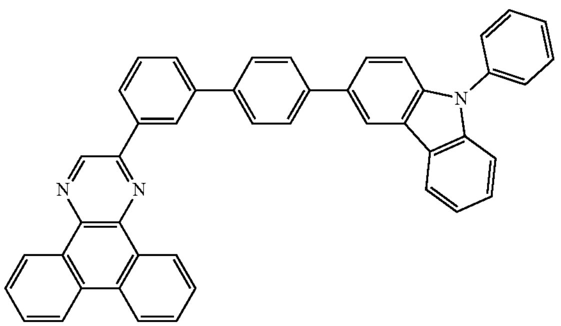

(103)

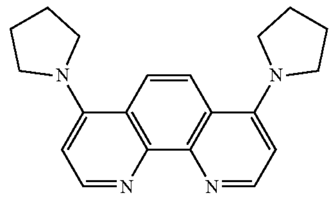

-continued
(104)
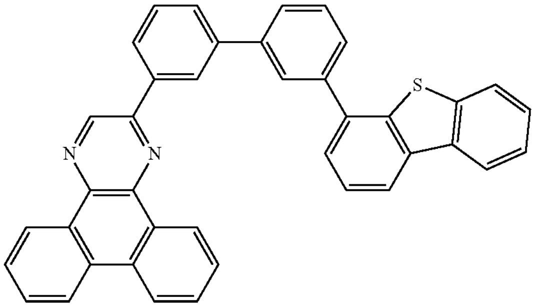
(106)
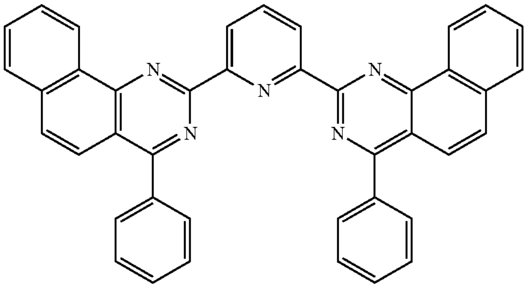
(105)
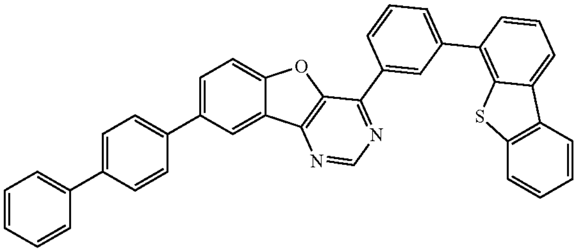
(107)
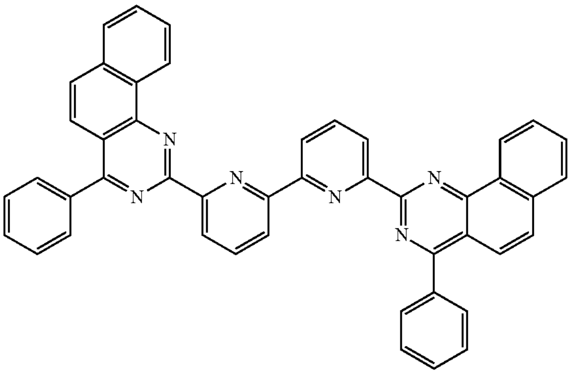
-continued
(108)
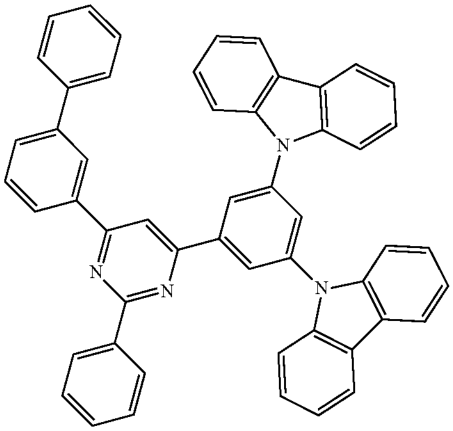
[Chemical Formula 2]
(109)
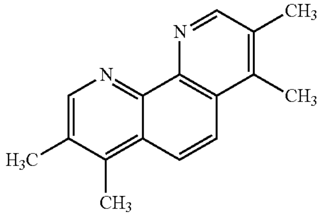
(110)
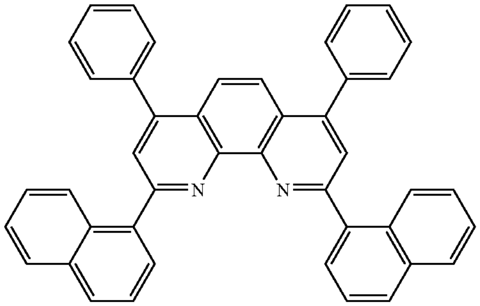
(111)
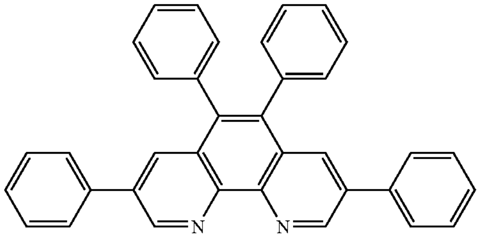
(112)
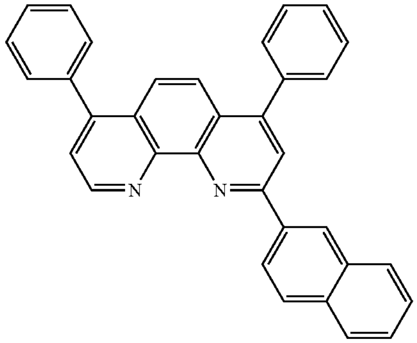

-continued (113)

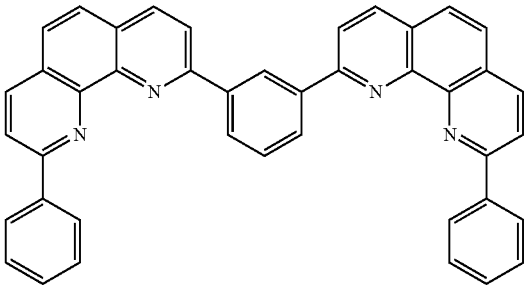

(114)

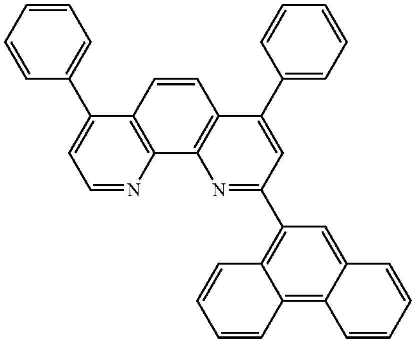

(115)

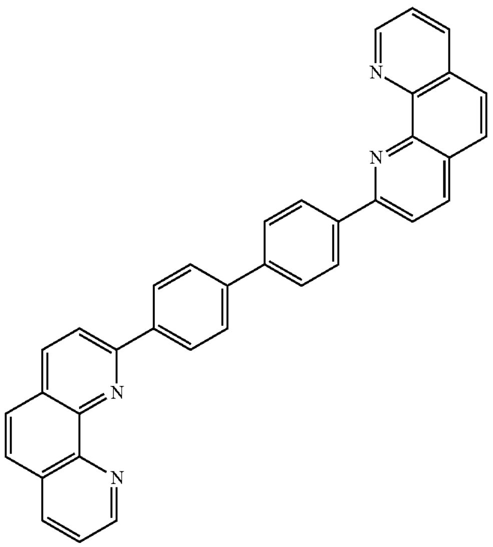

-continued (116)

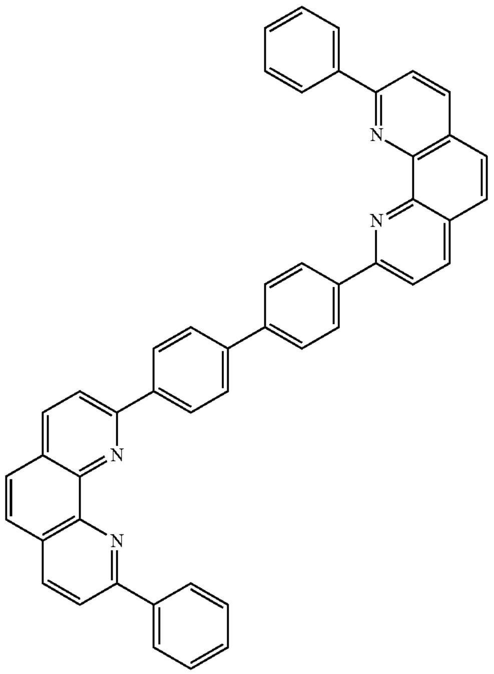

Figure 1B:
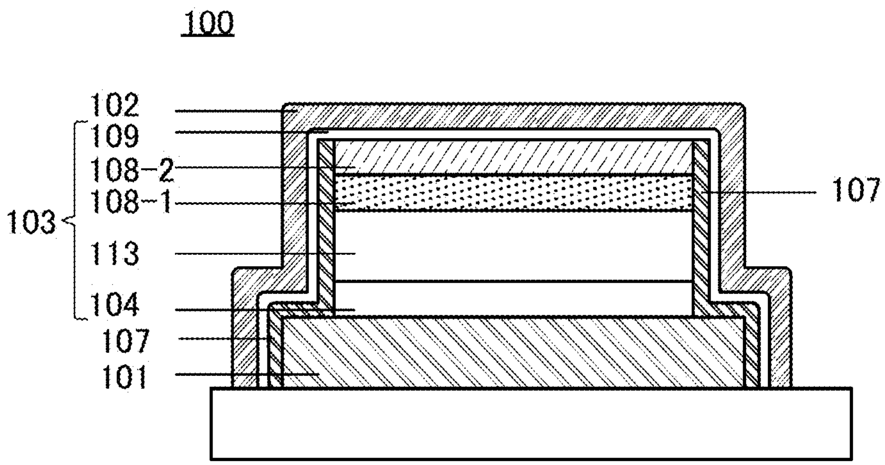
Figure 1C:
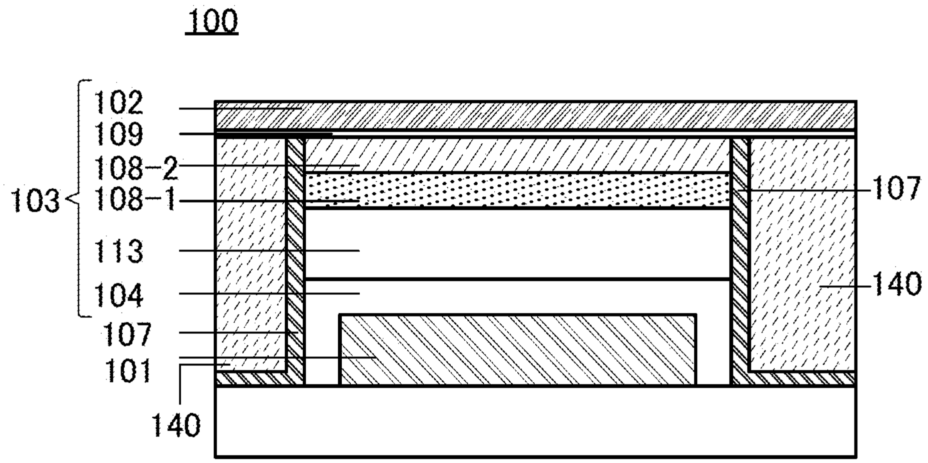

FIGS. 1B and 1C illustrate specific examples of the structure of the light-emitting device 100 in FIG. 1A. In FIG. 1B, the hole-injection/transport layer 104, the light-emitting layer 113, the first electron-transport layer 108-1, the second electron-transport layer 108-2, and the electron-injection layer 109 are sequentially stacked over the first electrode 101. As shown in the cross-sectional view in FIG. 1B, end portions (or side surfaces) of the hole-injection/transport layer 104, the light-emitting layer 113, the first electron-transport layer 108-1, and the second electron-transport layer 108-2 are on the inner side than an end portion (or a side surface) of the first electrode 101. In addition, the end portions (or side surfaces) of the hole-injection/transport layer 104, the light-emitting layer 113, the first electron-transport layer 108-1, and the second electron-transport layer 108-2, part of a top surface of the first electrode 101, and the end portion (or side surface) of the first electrode 101 are in contact with an insulating layer 107.

The insulating layer 107 can protect the end portions (or side surfaces) of the hole-injection/transport layer 104, the light-emitting layer 113, the first electron-transport layer 108-1, and the second electron-transport layer 108-2. This can reduce damage to the layers through the process and prevent the electrical connection caused by contact with another layer.

Although the electron-injection layer 109 is part of the EL layer 103, the shape of the electron-injection layer 109 differs from those of the other layers (the hole-injection/transport layer 104, the light-emitting layer 113, the first electron-transport layer 108-1, and the second electron-transport layer 108-2) of the EL layer 103, as illustrated in FIG. 1B. However, the shape of the electron-injection layer 109 may be the same as that of the second electrode 102. The electron-injection layer 109 and the second electrode 102 can be shared by a plurality of light-emitting devices; hence, the fabrication process of the light-emitting device 100 can be simplified and the throughput can be improved.

The light-emitting device may have a structure illustrated in FIG. 1C. In this structure, over the first electrode 101, the hole-injection/transport layer 104, the light-emitting layer 113, the first electron-transport layer 108-1, the second electron-transport layer 108-2, and the electron-injection layer 109 are sequentially stacked to cover the first electrode 101. As can be seen from the cross sectional view in FIG. 1C, the end portions of the hole-injection/transport layer 104, the light-emitting layer 113, the first electron-transport layer 108-1, and the second electron-transport layer 108-2 are on the outer side than the end portion (or side surface) of the first electrode 101. In addition, the end portions of the hole-injection/transport layer 104, the light-emitting layer 113, the first electron-transport layer 108-1, and the second electron-transport layer 108-2 are in contact with the insulating layer 107.

The insulating layer 107 is in contact with the end portions (or side surfaces) of the hole-injection/transport layer 104, the light-emitting layer 113, the first electron-transport layer 108-1, and the second electron-transport layer 108-2. The insulating layer 107 is positioned between a second insulating layer 140 and the end portions (or side surfaces) of the hole-injection/transport layer 104, the light-emitting layer 113, the first electron-transport layer 108-1, and the second electron-transport layer 108-2. The electron-injection layer 109 is provided over the second insulating layer 140, the insulating layer 107, and the second electron-transport layer 108-2. The second insulating layer 140 can be formed using an organic compound or an inorganic compound.

When the second insulating layer 140 is formed using an organic compound, an acrylic resin, a polyimide resin, an epoxy resin, a polyamide resin, a polyimide-amide resin, a siloxane resin, a benzocyclobutene-based resin, a phenol resin, precursors of these resins, or the like can be used, for example. A photosensitive resin may be used. Examples of the photosensitive resin include positive-type materials and negative-type materials.

When formed using a photosensitive resin, the second insulating layer 140 can be formed through only light-exposure and development steps in the fabrication process, reducing the influence of dry etching, wet etching, or the like on other layers. A negative photosensitive resin is preferably used, in which case a photomask (a light-exposure mask) used in this step can sometimes be used also in a different step.

With the device structures illustrated in FIGS. 1B and 1C, when some layers of the EL layer 103 are patterned to have a desired shape during the fabrication process, processing surfaces thereof might be heated or exposed to the air, causing problems such as crystallization of the light-emitting layer 113 or the electron-transport layer, which decreases the reliability and luminance of the light-emitting device. However, in the light-emitting device 100 described in this embodiment, a surface of the highly heat-resistant electron-transport layers (the surface obtained after the second electron-transport layer 108-2 is stacked over the first electron-transport layer 108-1) is the surface to be processed in the fabrication process, so that crystallization of the electron-transport layer having the surface to be processed can be inhibited. Note that in the EL layer 103 in this case, only the shape of the electron-injection layer 109 is different from those of the other layers (the hole-injection/transport layer 104, the light-emitting layer 113, the first electron-transport layer 108-1, and the second electron-transport layer 108-2) because the electron-injection layer 109 is formed after the formation of the electron-transport layers.

Although the light-emitting device 100 with the shape illustrated in each of FIGS. 1B and 1C is an example of the device structure that can be patterned in the above-described fabrication method, the present invention is not limited to such a method as long as the first electron-transport layer 108-1 and the second electron-transport layer 108-2 are included. With the device structure of one embodiment of the present invention, reduction in efficiency and reliability can be inhibited in the light-emitting device.

The insulating layer 107 illustrated in each of FIGS. 1B and 1C is not necessarily provided when not needed. For example, when electrical continuity between the electron-injection layer 109 and the hole-injection/transport layer 104 is sufficiently low, the light-emitting device 100 does not necessarily include the insulating layer 107.

Materials that can be used for the first electrode 101, the second electrode 102, the hole-injection/transport layer 104, the light-emitting layer 113, the electron-injection layer 109, and the insulating layer 107 will be described later in an embodiment below.

The stacked electron-transport layers (108-1 and 108-2) of the EL layer in the light-emitting device described in this embodiment can improve the heat resistance of the light-emitting device. In other words, the stacked electron-transport layers (108-1 and 108-2) can effectively reduce a morphological change caused by forming a thin film.

Note that in the case where the heteroaromatic compound included in the above-described stacked electron-transport layers (108-1 and 108-2) includes a fused heteroaromatic ring as a heteroaromatic ring, the thermophysical properties such as a glass transition temperature (Tg) and a crystallization temperature (Tc) are improved as compared with the layers including more heteroaromatic compounds not including the fused heteroaromatic ring.

When a thin film (single film) is formed by only one kind of heteroaromatic compound including a fused heteroaromatic ring, even if a stable glassy state is obtained apparently, the state is sometimes difficult to keep due to a strong interaction of molecules. In other words, in a thin film (single film) formed with only one kind of heteroaromatic compound, the glassy state should be maintained at Tg or lower temperatures; however, when being subjected to the atmosphere or stimulated at Tg or lower temperatures, crystallization might be observed to occur, which could not normally occur. When the glassy state of a thin film (single film) cannot be maintained at Tg or lower temperatures in this manner, in fabrication of a light-emitting device including a step where processing in the atmosphere is needed to form an organic EL layer, the organic EL layer may be crystallized in the middle of processing and thus the properties of the light-emitting device may be adversely affected.

However, since the light-emitting device of one embodiment of the present invention includes the stacked electron-transport layers (108-1 and 108-2), crystallization of the layers can be prevented. As described above, crystallization of a film at a temperature of Tg or lower can be prevented by the interaction between the stacked electron-transport layers (108-1 and 108-2) in the light-emitting device of one embodiment of the present invention. This can be indicated by the results described in Examples 1 and 2.

In the above light-emitting device, the interaction between stacked electron-transport materials in the stacked electron-transport layers has the effect of inhibiting the thermal crystallization in the case where the following conditions are satisfied. Specifically, preferably, the first electron-transport layer 108-1 in contact with the light-emitting layer is formed using the heteroaromatic compound having a difference less than or equal to 20° C. between the crystallization temperature (Tpc) of the powder state and the crystallization temperature (Ttc) of the thin film state and the second electron-transport layer 108-2 in contact with the first electron-transport layer 108-1 is formed using the heteroaromatic compound having a difference less than or equal to 100° C. between the crystallization temperature (Tpc) of the powder state and the crystallization temperature (Ttc) of the thin film state. Such a device structure can inhibit the crystallization of the materials used for the first electron-transport layer 108-1 and the second electron-transport layer 108-2 even when the processing involving heating over the surface of the second electron-transport layer 108-2 or heating in the air is performed. Thus, even a step such as heat treatment or heat treatment in the air is included in the organic EL layer formation in the light-emitting device fabrication is unlikely to adversely affect properties of the light-emitting device having the light-emitting device structure of one embodiment of the present invention, and accordingly the fabrication has the advantage of high process flexibility.

The structures described in this embodiment can be used in combination with any of the structures described in the other embodiments as appropriate.

Embodiment 2

In this embodiment, other structures of the light-emitting devices described in Embodiment 1 are described with reference to FIGS. 2A to 2E.

<<Basic Structure of Light-Emitting Device>>

Figure 2A:
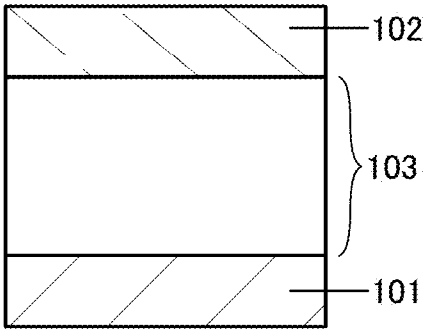
FIGS. 2A to 2E illustrate structures of light-emitting devices of an embodiment.

A basic structure of a light-emitting device is described. FIG. 2A illustrates a light-emitting device including, between a pair of electrodes, an EL layer including a light-emitting layer. Specifically, an EL layer 103 is positioned between a first electrode 101 and a second electrode 102.

Figure 2B:
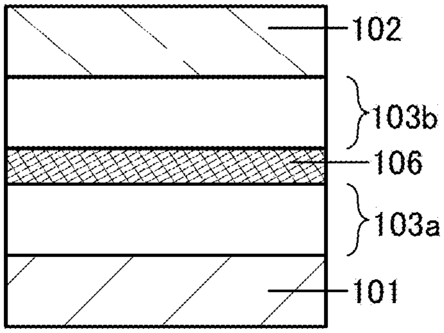

FIG. 2B illustrates a light-emitting device that has a stacked-layer structure (tandem structure) in which a plurality of EL layers (two EL layers 103*a* and 103*b* in FIG. 2B) are provided between a pair of electrodes and a charge-generation layer 106 is provided between the EL layers. A light-emitting device having a tandem structure enables fabrication of a light-emitting apparatus that has high efficiency without changing the amount of current.

The charge-generation layer 106 has a function of injecting electrons into one of the EL layers 103*a* and 103*b* and injecting holes into the other of the EL layers 103*a* and 103*b* when a potential difference is caused between the first electrode 101 and the second electrode 102. Thus, when voltage is applied in FIG. 2B such that the potential of the first electrode 101 is higher than that of the second electrode 102, the charge-generation layer 106 injects electrons into the EL layer 103*a* and injects holes into the EL layer 103*b*.

Note that in terms of light extraction efficiency, the charge-generation layer 106 preferably has a property of transmitting visible light (specifically, the charge-generation layer 106 preferably has a visible light transmittance of 40% or more). The charge-generation layer 106 functions even if it has lower conductivity than the first electrode 101 or the second electrode 102.

Figure 2C:
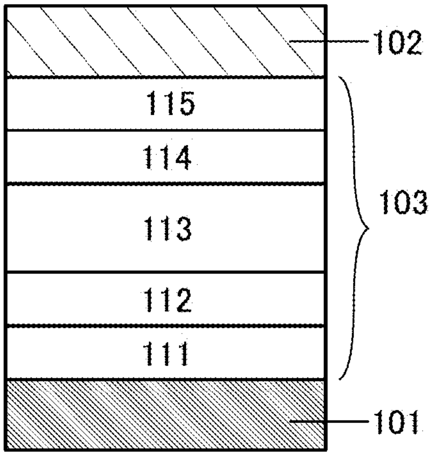

FIG. 2C illustrates a stacked-layer structure of the EL layer 103 in the light-emitting device of one embodiment of the present invention. In this case, the first electrode 101 is regarded as functioning as an anode and the second electrode 102 is regarded as functioning as a cathode. The EL layer 103 has a structure in which a hole-injection layer 111, a hole-transport layer 112, the light-emitting layer 113, an electron-transport layer 114, and an electron-injection layer 115 are stacked in this order over the first electrode 101. Note that the light-emitting layer 113 may have a stacked-layer structure of a plurality of light-emitting layers that emit light of different colors. For example, a light-emitting layer containing a light-emitting substance that emits red light, a light-emitting layer containing a light-emitting substance that emits green light, and a light-emitting layer containing a light-emitting substance that emits blue light may be stacked with or without a layer containing a carrier-transport material therebetween. Alternatively, a light-emitting layer containing a light-emitting substance that emits yellow light and a light-emitting layer containing a light-emitting substance that emits blue light may be used in combination. Note that the stacked-layer structure of the light-emitting layer 113 is not limited to the above. For example, the light-emitting layer 113 may have a stacked-layer structure of a plurality of light-emitting layers that emit light of the same color. For example, a first light-emitting layer containing a light-emitting substance that emits blue light and a second light-emitting layer containing a light-emitting substance that emits blue light may be stacked with or without a layer containing a carrier-transport material therebetween. The structure in which a plurality of light-emitting layers that emit light of the same color are stacked can achieve higher reliability than a single-layer structure in some cases. In the case where a plurality of EL layers are provided as in the tandem structure illustrated in FIG. 2B, the layers in each EL layer are sequentially stacked from the anode side as described above. When the first electrode 101 is the cathode and the second electrode 102 is the anode, the stacking order of the layers in the EL layer 103 is reversed. Specifically, the layer 111 over the first electrode 101 serving as the cathode is an electron-injection layer; the layer 112 is an electron-transport layer; the layer 113 is a light-emitting layer; the layer 114 is a hole-transport layer; and the layer 115 is a hole-injection layer.

The light-emitting layer 113 included in the EL layers (103, 103*a*, and 103*b*) contains an appropriate combination of a light-emitting substance and a plurality of substances, so that fluorescent light of a desired color or phosphorescent light of a desired color can be obtained. The light-emitting layer 113 may have a stacked-layer structure having different emission colors. In that case, light-emitting substances and other substances are different between the stacked light-emitting layers. Alternatively, the plurality of EL layers (103*a* and 103*b*) in FIG. 2B may exhibit their respective emission colors. Also in that case, the light-emitting substances and other substances are different between the stacked light-emitting layers.

The light-emitting device of one embodiment of the present invention can have a micro optical resonator (microcavity) structure when, for example, the first electrode 101 is a reflective electrode and the second electrode 102 is a transflective electrode in FIG. 2C. Thus, light from the light-emitting layer 113 in the EL layer 103 can be resonated between the electrodes and light emitted through the second electrode 102 can be intensified.

Note that when the first electrode 101 of the light-emitting device is a reflective electrode having a stacked-layer structure of a reflective conductive material and a light-transmitting conductive material (transparent conductive film), optical adjustment can be performed by adjusting the thickness of the transparent conductive film. Specifically, when the wavelength of light obtained from the light-emitting layer 113 is λ, the optical path length between the first electrode 101 and the second electrode 102 (the product of the thickness and the refractive index) is preferably adjusted to be mλ/2 (m is a natural number) or close to mλ/2.

To amplify desired light (wavelength: λ) obtained from the light-emitting layer 113, it is preferable to adjust each of the optical path length from the first electrode 101 to a region where the desired light is obtained in the light-emitting layer 113 (light-emitting region) and the optical path length from the second electrode 102 to the region where the desired light is obtained in the light-emitting layer 113 (light-emitting region) to be (2m'+1)λ/4 (m' is a natural number) or close to (2m'+1)λ/4. Here, the light-emitting region means a region where holes and electrons are recombined in the light-emitting layer 113.

By such optical adjustment, the spectrum of specific monochromatic light obtained from the light-emitting layer 113 can be narrowed and light emission with high color purity can be obtained.

In the above case, the optical path length between the first electrode 101 and the second electrode 102 is, to be exact, the total thickness from a reflective region in the first electrode 101 to a reflective region in the second electrode 102. However, it is difficult to precisely determine the reflective regions in the first electrode 101 and the second electrode 102; thus, it is assumed that the above effect can be sufficiently obtained wherever the reflective regions may be set in the first electrode 101 and the second electrode 102. Furthermore, the optical path length between the first electrode 101 and the light-emitting layer that emits the desired light is, to be exact, the optical path length between the reflective region in the first electrode 101 and the light-emitting region in the light-emitting layer that emits the desired light. However, it is difficult to precisely determine the reflective region in the first electrode 101 and the light-emitting region in the light-emitting layer that emits the desired light; thus, it is assumed that the above effect can be sufficiently obtained wherever the reflective region and the light-emitting region may be set in the first electrode 101 and the light-emitting layer that emits the desired light, respectively.

Figure 2D:
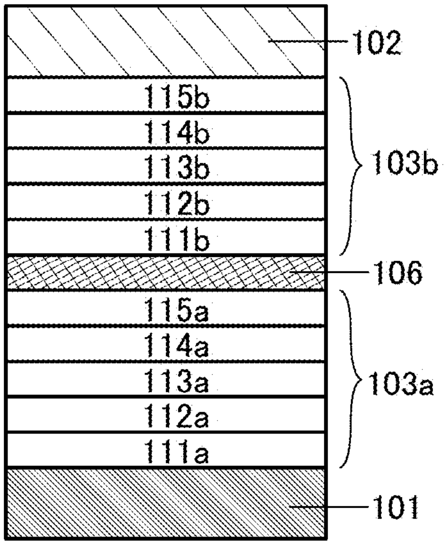

The light-emitting device illustrated in FIG. 2D is a light-emitting device having a tandem structure. Owing to a microcavity structure of the light-emitting device, light (monochromatic light) with different wavelengths from the EL layers (103*a* and 103*b*) can be extracted. Thus, it is unnecessary to separately form EL layers for obtaining a plurality of emission colors (e.g., R, G, and B). Therefore, high definition can be easily achieved. A combination with coloring layers (color filters) is also possible. Furthermore, the emission intensity of light with a specific wavelength in the front direction can be increased, whereby power consumption can be reduced.

Figure 2E:
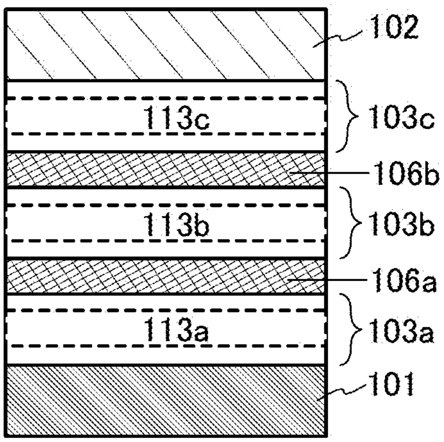

The light-emitting device illustrated in FIG. 2E is an example of the light-emitting device having the tandem structure illustrated in FIG. 2B, and includes three EL layers (103*a*, 103*b*, and 103*c*) stacked with charge-generation layers (106*a* and 106*b*) positioned therebetween, as illustrated in FIG. 2E. The three EL layers (103*a*, 103*b*, and 103*c*) include respective light-emitting layers (113*a*, 113*b*, and 113*c*), and the emission colors of the light-emitting layers can be selected freely. For example, the light-emitting layer 113*a* can emit blue light, the light-emitting layer 113*b* can emit red light, green light, or yellow light, and the light-emitting layer 113*c* can emit blue light, or the light-emitting layer 113*a* can emit red light, the light-emitting layer 113*b* can emit blue light, green light, or yellow light, and the light-emitting layer 113*c* can emit red light.

In the light-emitting device of one embodiment of the present invention, at least one of the first electrode 101 and the second electrode 102 is a light-transmitting electrode (e.g., a transparent electrode or a transflective electrode). In the case where the light-transmitting electrode is a transparent electrode, the transparent electrode has a visible light transmittance higher than or equal to 40%. In the case where the light-transmitting electrode is a transflective electrode, the transflective electrode has a visible light reflectance higher than or equal to 20% and lower than or equal to 80%, preferably higher than or equal to 40% and lower than or equal to 70%. These electrodes preferably have a resistivity of $1\times10^{-2}$ Ωcm or less.

When one of the first electrode 101 and the second electrode 102 is a reflective electrode in the light-emitting device of one embodiment of the present invention, the visible light reflectance of the reflective electrode is higher than or equal to 40% and lower than or equal to 100%, preferably higher than or equal to 70% and lower than or equal to 100%. This electrode preferably has a resistivity of $1\times10^{-2}$ Ωcm or less.

<<Specific Structure of Light-Emitting Device>>

Next, a specific structure of the light-emitting device of one embodiment of the present invention will be described. Here, the description is made using FIG. 2D illustrating the tandem structure. Note that the structure of the EL layer applies also to the structure of the light-emitting devices having a single structure in FIG. 2A and FIG. 2C. When the light-emitting device in FIG. 2D has a microcavity structure, the first electrode 101 is formed as a reflective electrode and the second electrode 102 is formed as a transflective electrode. Thus, a single-layer structure or a stacked-layer structure can be formed using one or more kinds of desired electrode materials. Note that the second electrode 102 is formed after formation of the EL layer 103*b*, with the use of a material selected as appropriate.

<First Electrode and Second Electrode>

As materials for the first electrode 101 and the second electrode 102, any of the following materials can be used in an appropriate combination as long as the above functions of the electrodes can be fulfilled. For example, a metal, an alloy, an electrically conductive compound, a mixture of these, and the like can be used as appropriate. Specifically, an In—Sn oxide (also referred to as ITO), an In—Si—Sn oxide (also referred to as ITSO), an In—Zn oxide, or an In—W—Zn oxide can be used. In addition, it is possible to use a metal such as aluminum (Al), titanium (Ti), chromium (Cr), manganese (Mn), iron (Fe), cobalt (Co), nickel (Ni), copper (Cu), gallium (Ga), zinc (Zn), indium (In), tin (Sn), molybdenum (Mo), tantalum (Ta), tungsten (W), palladium (Pd), gold (Au), platinum (Pt), silver (Ag), yttrium (Y), or neodymium (Nd) or an alloy containing an appropriate combination of any of these metals. It is also possible to use a Group 1 element or a Group 2 element in the periodic table that is not described above (e.g., lithium (Li), cesium (Cs), calcium (Ca), or strontium (Sr)), a rare earth metal such as europium (Eu) or ytterbium (Yb), an alloy containing an appropriate combination of any of these elements, graphene, or the like.

In the light-emitting device in FIG. 2D, when the first electrode 101 is the anode, a hole-injection layer 111*a* and a hole-transport layer 112*a* of the EL layer 103*a* are sequentially stacked over the first electrode 101 by a vacuum evaporation method. After the EL layer 103*a* and the charge-generation layer 106 are formed, a hole-injection layer 111*b* and a hole-transport layer 112*b* of the EL layer 103*b* are sequentially stacked over the charge-generation layer 106 in a similar manner.

<Hole-Injection Layer>

The hole-injection layers (111, 111*a*, and 111*b*) inject holes from the first electrode 101 serving as the anode and the charge-generation layers (106, 106*a*, and 106*b*) to the EL layers (103, 103*a*, and 103*b*) and contain an organic acceptor material or a material having a high hole-injection property.

The organic acceptor material allows holes to be generated in another organic compound whose HOMO level is close to the LUMO level of the organic acceptor material when charge separation is caused between the organic acceptor material and the organic compound. Thus, as the organic acceptor material, a compound having an electron-withdrawing group (e.g., a halogen group or a cyano group), such as a quinodimethane derivative, a chloranil derivative, and a hexaazatriphenylene derivative, can be used. Examples of the organic acceptor material include 7,7,8,8-tetracyano-2,3,5,6-tetrafluoroquinodimethane (abbreviation: $F_4$-TCNQ), 3,6-difluoro-2,5,7,7,8,8-hexacyanoquinodimethane, chloranil, 2,3,6,7,10,11-hexacyano-1,4,5,8,9,12-hexaazatriphenylene (abbreviation: HAT-CN), 1,3,4,5,7,8-hexafluorotetracyano-naphthoquinodimethane (abbreviation: F6-TCNNQ), and 2-(7-dicyanomethylene-1,3,4,5,6,8,9,10-octafluoro-7H-pyren-2-ylidene)malononitrile. Note that among organic acceptor materials, a compound in which electron-withdrawing groups are bonded to fused aromatic rings each having a plurality of heteroatoms, such as HAT-CN, is particularly preferred because it has a high acceptor property and stable film quality against heat. Besides, a [3]radialene derivative having an electron-withdrawing group (particularly a cyano group or a halogen group such as a fluoro group), which has a very high electron-accepting property, is preferred; specific examples include α,α,α"-1,2,3-cyclopropanetriylidenetris[4-cyano-2,3,5,6-tetrafluorobenzeneacetonitrile], α,α,α"-1,2,3-cyclopropanetriylidenetris[2,6-dichloro-3,5-difluoro-4-(trifluoromethyl)benzeneacetonitrile], and α,α,α"-1,2,3-cyclopropanetriylidenetris[2,3,4,5,6-pentafluorobenzeneacetonitrile].

As the material having a high hole-injection property, an oxide of a metal belonging to Group 4 to Group 8 in the periodic table (e.g., a transition metal oxide such as molybdenum oxide, vanadium oxide, ruthenium oxide, tungsten oxide, or manganese oxide) can be used. Specific examples include molybdenum oxide, vanadium oxide, niobium oxide, tantalum oxide, chromium oxide, tungsten oxide, manganese oxide, and rhenium oxide. Among these oxides, molybdenum oxide is preferable because it is stable in the air, has a low hygroscopic property, and is easily handled. Other examples are phthalocyanine (abbreviation: $H_2Pc$), a phthalocyanine-based compound such as copper phthalocyanine (abbreviation: CuPc), and the like.

Other examples are aromatic amine compounds, which are low-molecular compounds, such as 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), 4,4'-bis[N-(4-diphenylaminophenyl)-N-phenylamino]biphenyl (abbreviation: DPAB), N,N'-bis{4-[bis(3-methylphenyl)amino]phenyl}-N,N'-diphenyl-(1,1'-biphenyl)-4,4'-diamine (abbreviation: DNTPD), 1,3,5-tris[N-(4-diphenylaminophenyl)-N-phenylamino]benzene (abbreviation: DPA3B), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), and 3-[N-(1-naphthyl)-N-(9-phenylcarbazol-3-yl)amino]-9-phenylcarbazole (abbreviation: PCzPCN1).

Other examples are high-molecular compounds (e.g., oligomers, dendrimers, and polymers) such as poly(N-vinylcarbazole) (abbreviation: PVK), poly(4-vinyltriphenylamine) (abbreviation: PVTPA), poly[N-(4-{N-[4-(4-diphenylamino)phenyl]phenyl-N'-phenylamino}phenyl)methacrylamide] (abbreviation: PTPDMA), and poly[N,N'-bis(4-butylphenyl)-N,N'-bis(phenyl)benzidine] (abbreviation: Poly-TPD). Alternatively, it is possible to use a high-molecular compound to which acid is added, such as poly(3,4-ethylenedioxythiophene)/poly(styrenesulfonic acid) (abbreviation: PEDOT/PSS) or polyaniline/poly(styrenesulfonic acid) (abbreviation: PAni/PSS), for example.

As the material having a high hole-injection property, a mixed material containing a hole-transport material and the above-described organic acceptor material (electron-accepting material) can be used. In that case, the organic acceptor material extracts electrons from the hole-transport material, so that holes are generated in the hole-injection layer 111 and the holes are injected into the light-emitting layer 113 through the hole-transport layer 112. Note that the hole-injection layer 111 may be formed to have a single-layer structure using a mixed material containing a hole-transport material and an organic acceptor material (electron-accepting material), or a stacked-layer structure of a layer containing a hole-transport material and a layer containing an organic acceptor material (electron-accepting material).

The hole-transport material preferably has a hole mobility higher than or equal to $1\times10^{-6}$ $cm^2/Vs$ in the case where the square root of the electric field strength [V/cm] is 600. Note that other substances can also be used as long as the substances have hole-transport properties higher than electron-transport properties.

As the hole-transport material, materials having a high hole-transport property, such as a compound having a π-electron rich heteroaromatic ring (e.g., a carbazole derivative, a furan derivative, and a thiophene derivative) and an aromatic amine (an organic compound having an aromatic amine skeleton), are preferable.

Examples of the carbazole derivative (an organic compound having a carbazole ring) include a bicarbazole derivative (e.g., a 3,3'-bicarbazole derivative) and an aromatic amine having a carbazolyl group.

Specific examples of the bicarbazole derivative (e.g., a 3,3'-bicarbazole derivative) include 3,3'-bis(9-phenyl-9H-carbazole) (abbreviation: PCCP), 9,9'-bis(biphenyl-4-yl)-3,3'-bi-9H-carbazole (abbreviation: BisBPCz), 9,9'-bis(1,1'-biphenyl-3-yl)-3,3'-bi-9H-carbazole (abbreviation: BismBPCz), 9-(1,1'-biphenyl-3-yl)-9'-(1,1'-biphenyl-4-yl)-9H,9'H-3,3'-bicarbazole (abbreviation: mBPCCBP), and 9-(2-naphthyl)-9'-phenyl-9H,9'H-3,3'-bicarbazole (abbreviation: βNCCP).

Specific examples of the aromatic amine having a carbazolyl group include 4-phenyl-4'-(9-phenyl-9H-carbazol-3-yl)triphenylamine (abbreviation: PCBA1BP), N-(4-biphenyl)-N-(9,9-dimethyl-9H-fluoren-2-yl)-9-phenyl-9H-carbazol-3-amine (abbreviation: PCBiF), N-(1,1'-biphenyl-4-yl)-N-[4-(9-phenyl-9H-carbazol-3-yl)phenyl]-9,9-dimethyl-9H-fluoren-2-amine (abbreviation: PCBBiF), 4,4'-diphenyl-4"-(9-phenyl-9H-carbazol-3-yl)triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4"-(9-phenyl-9H-carbazol-3-yl)triphenylamine (abbreviation: PCBNBB), 4-phenyldiphenyl-(9-phenyl-9H-carbazol-3-yl)amine (abbreviation: PCA1BP), N,N'-bis(9-phenylcarbazol-3-yl)-N,N'-diphenylbenzene-1,3-diamine (abbreviation: PCA2B), N,N,N'-triphenyl-N,N,N'-tris(9-phenylcarbazol-3-yl)benzene-1,3,5-tri amine (abbreviation: PCA3B), 9,9-dimethyl-N-phenyl-N-[4-(9-phenyl-9H-carbazol-3-yl)phenyl]fluoren-2-amine (abbreviation: PCBAF), N-phenyl-N-[4-(9-phenyl-9H-carbazol-3-yl)phenyl]spiro-9,9'-bifluoren-2-amine (abbreviation: PCBASF), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), 3-[N-(1-naphthyl)-N-(9-phenylcarbazol-3-yl)amino]-9-phenylcarbazole (abbreviation: PCzPCN1), 3-[N-(4-diphenylaminophenyl)-N-phenylamino]-9-phenylcarbazole (abbreviation: PCzDPA1), 3,6-bis[N-(4-diphenylaminophenyl)-N-phenylamino]-9-phenylcarbazole (abbreviation: PCzDPA2), 3,6-bis[N-(4-diphenylaminophenyl)-N-(1-naphthyl)amino]-9-phenylcarbazole (abbreviation: PCzTPN2), 2-[N-(9-phenylcarbazol-3-yl)-N-phenylamino]spiro-9,9'-bifluorene (abbreviation: PCASF), N-[4-(9H-carbazol-9-yl)phenyl]-N-(4-phenyl)phenylaniline (abbreviation: YGA1BP), N,N'-bis[4-(carbazol-9-yl)phenyl]-N,N'-diphenyl-9,9-dimethylfluorene-2,7-diamine (abbreviation: YGA2F), and 4,4',4''-tris(carbazol-9-yl)triphenylamine (abbreviation: TCTA).

Other examples of the carbazole derivative include 3-[4-(9-phenanthryl)-phenyl]-9-phenyl-9H-carbazole (abbreviation: PCPPn), 3-[4-(1-naphthyl)-phenyl]-9-phenyl-9H-carbazole (abbreviation: PCPN), 1,3-bis(N-carbazolyl)benzene (abbreviation: mCP), 4,4'-di(N-carbazolyl)biphenyl (abbreviation: CBP), 3,6-bis(3,5-diphenylphenyl)-9-phenylcarbazole (abbreviation: CzTP), 1,3,5-tris[4-(N-carbazolyl)phenyl]benzene (abbreviation: TCPB), and 9-[4-(10-phenyl-9-anthracenyl)phenyl]-9H-carbazole (abbreviation: CzPA).

Specific examples of the furan derivative (an organic compound having a furan ring) include 4,4',4''-(benzene-1,3,5-triyl)tri(dibenzofuran) (abbreviation: DBF3P-II) and 4-{3-[3-(9-phenyl-9H-fluoren-9-yl)phenyl]phenyl}dibenzofuran (abbreviation: mmDBFFLBi-II).

Specific examples of the thiophene derivative (an organic compound having a thiophene ring) include organic compounds having a thiophene ring, such as 4,4',4''-(benzene-1,3,5-triyl)tri(dibenzothiophene) (abbreviation: DBT3P-II), 2,8-diphenyl-4-[4-(9-phenyl-9H-fluoren-9-yl)phenyl]dibenzothiophene (abbreviation: DBTFLP-III), and 4-[4-(9-phenyl-9H-fluoren-9-yl)phenyl]-6-phenyldibenzothiophene (abbreviation: DBTFLP-IV).

Specific examples of the aromatic amine include 4,4'-bis[N-(1-naphthyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), 4,4'-bis[N-(spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), N-(9,9-dimethyl-9H-fluoren-2-yl)-N-{9,9-dimethyl-2-[N'-phenyl-N-(9,9-dimethyl-9H-fluoren-2-yl)amino]-9H-fluoren-7-yl}phenylamine (abbreviation: DFLADFL), N-(9,9-dimethyl-2-diphenylamino-9H-fluoren-7-yl)diphenylamine (abbreviation: DPNF), 2-[N-(4-diphenylaminophenyl)-N-phenylamino]spiro-9,9'-bifluorene (abbreviation: DPASF), 2,7-bis[N-(4-diphenylaminophenyl)-N-phenylamino]spiro-9,9'-bifluorene (abbreviation: DPA2SF), 4,4',4''-tris[N-(1-naphthyl)-N-phenylamino]triphenylamine (abbreviation: 1'-TNATA), 4,4',4''-tris(N,N-diphenylamino)triphenylamine (abbreviation: TDATA), 4,4',4''-tris[N-(3-methylphenyl)-N-phenylamino]triphenylamine (abbreviation: m-MTDATA), N,N'-di(p-tolyl)-N,N'-diphenyl-p-phenylenediamine (abbreviation: DTDPPA), 4,4'-bis[N-(4-diphenylaminophenyl)-N-phenylamino]biphenyl (abbreviation: DPAB), DNTPD, 1,3,5-tris[N-(4-diphenylaminophenyl)-N-phenylamino]benzene (abbreviation: DPA3B), N-(4-biphenyl)-6,N-diphenylbenzo[b]naphtho[1,2-d]furan-8-amine (abbreviation: BnfABP), N,N-bis(4-biphenyl)-6-phenylbenzo[b]naphtho[1,2-d]furan-8-amine (abbreviation: BBABnf), 4,4'-bis(6-phenylbenzo[b]naphtho[1,2-d]furan-8-yl)-4''-phenyltriphenylamine (abbreviation: BnfBB1BP), N,N-bis(4-biphenyl)benzo[b]naphtho[1,2-d]furan-6-amine (abbreviation: BBABnf(6)), N,N-bis(4-biphenyl)benzo[b]naphtho[1,2-d]furan-8-amine (abbreviation: BBABnf(8)), N,N-bis(4-biphenyl)benzo[b]naphtho[2,3-d]furan-4-amine (abbreviation: BBABnf(II)(4)), N,N-bis[4-(dibenzofuran-4-yl)phenyl]-4-amino-p-terphenyl (abbreviation: DBfBB1TP), N-[4-(dibenzothiophen-4-yl)phenyl]-N-phenyl-4-biphenylamine (abbreviation: ThBA1BP), 4-(2-naphthyl)-4',4''-diphenyltriphenylamine (abbreviation: BBAβNB), 4-[4-(2-naphthyl)phenyl]-4',4''-diphenyltriphenylamine (abbreviation: BBAβNBi), 4,4'-diphenyl-4''-(6;1'-binaphthyl-2-yl)triphenylamine (abbreviation: BBAαNβNB), 4,4'-diphenyl-4''-(7;1'-binaphthyl-2-yl)triphenylamine (abbreviation: BBAαNβNB-03), 4,4'-diphenyl-4''-(7-phenyl)naphthyl-2-yl)triphenylamine (abbreviation: BBAPβNB-03), 4,4'-diphenyl-4''-(6;2'-binaphthyl-2-yl)triphenylamine (abbreviation: BBA(βN2)B), 4,4'-diphenyl-4''-(7;2'-binaphthyl-2-yl)triphenylamine (abbreviation: BBA(βN2)B-03), 4,4'-diphenyl-4''-(4;2'-binaphthyl-1-yl)triphenylamine (abbreviation: BBAβNαNB), 4,4'-diphenyl-4''-(5;2'-binaphthyl-1-yl)triphenylamine (abbreviation: BBAβNαNB-02), 4-(4-biphenylyl)-4'-(2-naphthyl)-4''-phenyltriphenylamine (abbreviation: TPBiAβNB), 4-(3-biphenylyl)-4'-[4-(2-naphthyl)phenyl]-4''-phenyltriphenylamine (abbreviation: mTPBiAβNBi), 4-(4-biphenylyl)-4'-[4-(2-naphthyl)phenyl]-4''-phenyltriphenylamine (abbreviation: TPBiAβNBi), 4-phenyl-4'-(1-naphthyl)-triphenylamine (abbreviation: αNBA1BP), 4,4'-bis(1-naphthyl)triphenylamine (abbreviation: αNBB1BP), 4,4'-diphenyl-4''[4'-(carbazol-9-yl)biphenyl-4-yl]triphenylamine (abbreviation: YGTBi1BP), 4'-[4-(3-phenyl-9H-carbazol-9-yl)phenyl]tris(1,1'-biphenyl-4-yl)amine (abbreviation: YGTBi1BP-02), 4-[4'-(carbazol-9-yl)biphenyl-4-yl]-4'-(2-naphthyl)-4''-phenyltriphenylamine (abbreviation: YGTBiβNB), N-[4-(9-phenyl-9H-carbazol-3-yl)phenyl]-N-[4-(1-naphthyl)phenyl]-9,9'-spirobi[9H-fluoren]-2-amine (abbreviation: PCBNBSF), N,N-bis([1,1'-biphenyl]-4-yl)-9,9'-spirobi[9H-fluoren]-2-amine (abbreviation: BBASF), N,N-bis([1,1'-biphenyl]-4-yl)-9,9'-spirobi[9H-fluoren]-4-amine (abbreviation: BBASF(4)), N-(1,1'-biphenyl-2-yl)-N-(9,9-dimethyl-9H-fluoren-2-yl)-9,9'-spirobi[9H-fluoren]-4-amine (abbreviation: oFBiSF), N-(4-biphenyl)-N-(9,9-dimethyl-9H-fluoren-2-yl)dibenzofuran-4-amine (abbreviation: FrBiF), N-[4-(1-naphthyl)phenyl]-N-[3-(6-phenyldibenzofuran-4-yl)phenyl]-1-naphthylamine (abbreviation: mPDBfBNBN), 4-phenyl-4'-[4-(9-phenylfluoren-9-yl)phenyl]triphenylamine (abbreviation: BPAFLBi), N,N-bis(9,9-dimethyl-9H-fluoren-2-yl)-9,9'-spirobi-9H-fluoren-4-amine, N,N-bis(9,9-dimethyl-9H-fluoren-2-yl)-9,9'-spirobi-9H-fluoren-3-amine, N,N-bis(9,9-dimethyl-9H-fluoren-2-yl)-9,9'-spirobi-9H-fluoren-2-amine, and N,N-bis(9,9-dimethyl-9H-fluoren-2-yl)-9,9'-spirobi-9H-fluoren-1-amine.

Other examples of the hole-transport material include high-molecular compounds (e.g., oligomers, dendrimers, and polymers) such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), and poly[N,N'-bis(4-butylphenyl)-N,N'-bis(phenyl)benzidine] (abbreviation: Poly-TPD). Alternatively, it is possible to use a high-molecular compound to which acid is added, such as poly(3,4-ethylenedioxythiophene)/poly(styrenesulfonic acid) (abbreviation: PEDOT/P S S) or polyaniline/poly(styrenesulfonic acid) (abbreviation: PAni/PSS), for example.

Note that the hole-transport material is not limited to the above examples, and any of a variety of known materials may be used alone or in combination as the hole-transport material.

The hole-injection layers (111, 111*a*, and 111*b*) can be formed by any of known film formation methods such as a vacuum evaporation method.

<Hole-Transport Layer>

The hole-transport layers (112, 112*a*, and 112*b*) transport the holes, which are injected from the first electrodes 101 by the hole-injection layers (111, 111*a*, and 111*b*), to the light-emitting layers (113, 113*a*, and 113*b*). Note that the hole-transport layers (112, 112*a*, and 112*b*) each contain a hole-transport material. Thus, the hole-transport layers (112, 112*a*, and 112*b*) can be formed using hole-transport materials that can be used for the hole-injection layers (111, 111*a*, and 111*b*).

Note that in the light-emitting device of one embodiment of the present invention, the organic compound used for the hole-transport layers (112, 112*a*, and 112*b*) can also be used for the light-emitting layers (113, 113*a*, and 113*b*). The use of the same organic compound for the hole-transport layers (112, 112*a*, and 112*b*) and the light-emitting layers (113, 113*a*, and 113*b*) is preferable, in which case holes can be efficiently transported from the hole-transport layers (112, 112*a*, and 112*b*) to the light-emitting layers (113, 113*a*, and 113*b*).

<Light-Emitting Layer>

The light-emitting layers (113, 113*a*, and 113*b*) contain a light-emitting substance. Note that as a light-emitting substance that can be used in the light-emitting layers (113, 113*a*, and 113*b*), a substance whose emission color is blue, violet, bluish violet, green, yellowish green, yellow, orange, red, or the like can be used as appropriate. When a plurality of light-emitting layers are provided, the use of different light-emitting substances for the light-emitting layers enables a structure that exhibits different emission colors (e.g., white light emission obtained by a combination of complementary emission colors). Furthermore, one light-emitting layer may have a stacked-layer structure including different light-emitting substances.

The light-emitting layers (113, 113*a*, and 113*b*) may each contain one or more kinds of organic compounds (e.g., a host material) in addition to a light-emitting substance (a guest material).

In the case where a plurality of host materials are used in the light-emitting layers (113, 113*a*, and 113*b*), a second host material that is additionally used is preferably a substance having a larger energy gap than those of a known guest material and a first host material. Preferably, the lowest singlet excitation energy level (S1 level) of the second host material is higher than that of the first host material, and the lowest triplet excitation energy level (T1 level) of the second host material is higher than that of the guest material. Preferably, the lowest triplet excitation energy level (T1 level) of the second host material is higher than that of the first host material. With such a structure, an exciplex can be formed by the two kinds of host materials. To form an exciplex efficiently, it is particularly preferable to combine a compound that easily accepts holes (hole-transport material) and a compound that easily accepts electrons (electron-transport material). With the above structure, high efficiency, low voltage, and a long lifetime can be achieved at the same time.

As an organic compound used as the host material (including the first host material and the second host material), organic compounds such as the hole-transport materials usable for the hole-transport layers (112, 112*a*, and 112*b*) described above and electron-transport materials usable for electron-transport layers (114, 114*a*, and 114*b*) described later can be used as long as they satisfy requirements for the host material used in the light-emitting layer. Another example is an exciplex formed by two or more kinds of organic compounds (the first host material and the second host material). An exciplex whose excited state is formed by two or more kinds of organic compounds has an extremely small difference between the S1 level and the T1 level and functions as a TADF material capable of converting triplet excitation energy into singlet excitation energy. In an example of a preferred combination of two or more kinds of organic compounds forming an exciplex, one compound of the two or more kinds of organic compounds has a π-electron deficient heteroaromatic ring and the other compound has a π-electron rich heteroaromatic ring. A phosphorescent substance such as an iridium-, rhodium-, or platinum-based organometallic complex or a metal complex may be used as one compound of the combination for forming an exciplex.

There is no particular limitation on the light-emitting substances that can be used for the light-emitting layers (113, 113*a*, and 113*b*), and a light-emitting substance that converts singlet excitation energy into light in the visible light range or a light-emitting substance that converts triplet excitation energy into light in the visible light range can be used.

<<Light-Emitting Substance that Converts Singlet Excitation Energy into Light>>

The following substances that emit fluorescent light (fluorescent substances) can be given as examples of the light-emitting substance that converts singlet excitation energy into light and can be used in the light-emitting layers (113, 113*a*, and 113*b*): a pyrene derivative, an anthracene derivative, a triphenylene derivative, a fluorene derivative, a carbazole derivative, a dibenzothiophene derivative, a dibenzofuran derivative, a dibenzoquinoxaline derivative, a quinoxaline derivative, a pyridine derivative, a pyrimidine derivative, a phenanthrene derivative, and a naphthalene derivative. A pyrene derivative is particularly preferable because it has a high emission quantum yield. Specific examples of pyrene derivatives include N,N'-bis(3-methylphenyl)-N,N'-bis[3-(9-phenyl-9H-fluoren-9-yl)phenyl]pyrene-1,6-diamine (abbreviation: 1, 6mMemFLPAPrn), N,N'-diphenyl-N,N'-bis[4-(9-phenyl-9H-fluoren-9-yl)phenyl]pyrene-1,6-diamine (abbreviation: 1,6FLPAPrn), N,N'-bis(dibenzofuran-2-yl)-N,N'-diphenylpyrene-1,6-diamine (abbreviation: 1,6FrAPrn), N,N'-bis(dibenzothiophen-2-yl)-N,N'-diphenylpyrene-1,6-diamine (abbreviation: 1,6ThAPrn), N,N'-(pyrene-1,6-diyl)bis[(N-phenylbenzo[b]naphtho[1,2-d]furan)-6-amine] (abbreviation: 1,6BnfAPrn), N,N'-(pyrene-1,6-diyl)bis[(N-phenylbenzo[b]naphtho[1,2-d]furan)-8-amine] (abbreviation: 1,6BnfAPrn-02), and -(pyrene-1,6-diyl)bis[(6,N-diphenylbenzo[b]naphtho[1,2-d]furan)-8-amine] (abbreviation: 1,6BnfAPrn-03).

In addition, it is possible to use, for example, 5,6-bis[4-(10-phenyl-9-anthryl)phenyl]-2,2'-bipyridine (abbreviation: PAP2BPy), 5,6-bis[4'-(10-phenyl-9-anthryl)biphenyl-4-yl]-2,2'-bipyridine (abbreviation: PAPP2BPy), N,N'-bis[4-(9H- carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(9H-carbazol-9-yl)-4'-(9,10-diphenyl-2-anthryl)triphenylamine (abbreviation: 2YGAPPA), N,9-diphenyl-N-[4-(10-phenyl-9-anthryl)phenyl]-9H-carbazol-3-amine (abbreviation: PCAPA), 4-(10-phenyl-9-anthryl)-4'-(9-phenyl-9H-carbazol-3-yl)triphenylamine (abbreviation: PCBAPA), 4-[4-(10-phenyl-9-anthryl)phenyl]-4'-(9-phenyl-9H-carbazol-3-yl)triphenylamine (abbreviation: PCBAPBA), perylene, 2,5,8,11-tetra-tert-butylperylene (abbreviation: TBP), N,N'-(2-tert-butylanthracene-9,10-diyldi-4,1-phenylene)bis[N,N',N'-triphenyl-1,4-phenylenediamine] (abbreviation: DPABPA), N,9-diphenyl-N-[4-(9,10-diphenyl-2-anthryl)phenyl]-9H-carbazol-3-amine (abbreviation: 2PCAPPA), and N-[4-(9,10-diphenyl-2-anthryl)phenyl]-N,N',N'-triphenyl-1,4-phenylenediamine (abbreviation: 2DPAPPA).

It is also possible to use, for example, N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N''-triphenyl-1,4-phenylenediamine (abbreviation: 2DPABPhA), 9,10-bis(1,1'-biphenyl-2-yl)-N-[4-(9H-carbazol-9-yl)phenyl]-N-phenylanthracen-2-amine (abbreviation: 2YGABPhA), N,N,9-triphenylanthracen-9-amine (abbreviation: DPhAPhA), coumarin 545T, N,N'-diphenylquinacridone (abbreviation: DPQd), rubrene, 5,12-bis(1,1'-biphenyl-4-yl)-6,11-diphenyltetracene (abbreviation: BPT), 2-(2-{2-[4-(dimethylamino)phenyl]ethenyl}-6-methyl-4H-pyran-4-ylidene)propanedinitrile (abbreviation: DCM1), 2-{2-methyl-6-[2-(2,3,6,7-tetrahydro-1H,5H-benzo[ij]quinolizin-9-yl)ethenyl]-4H-pyran-4-ylidene}propanedinitrile (abbreviation: DCM2), N,N,N',-'-tetrakis(4-methylphenyl)tetracene-5,11-diamine (abbreviation: p-mPhTD), 7,14-diphenyl-N,N,N',N'-tetrakis(4-methylphenyl)acenaphtho[1,2-a]fluoranthene-3,10-diamine (abbreviation: p-mPhAFD), 2-{2-isopropyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTI), 2-{2-tert-butyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTB), 2-(2,6-bis{2-[4-(dimethylamino)phenyl]ethenyl}-4H-pyran-4-ylidene)propanedinitrile (abbreviation: BisDCM), 2-{2,6-bis[2-(8-methoxy-1,1,7,7-tetramethyl-2,3,6,7-tetrahydro-1H,5H-benzo[ij]quinolizin-9-yl)ethenyl]-4H-pyran-4-ylidene}propanedinitrile (abbreviation: BisDCJTM), 1,6BnfAPrn-03, 3,10-bis[N-(9-phenyl-9H-carbazol-2-yl)-N-phenylamino]naphtho[2,3-b;6,7-b']bisbenzofuran (abbreviation: 3,10PCA2Nbf(IV)-02), and 3,10-bis[N-(dibenzofuran-3-yl)-N-phenylamino]naphtho[2,3-b;6,7-b']bisbenzofuran (abbreviation: 3,10FrA2Nbf(IV)-02). In particular, pyrenediamine compounds such as 1,6FLPAPrn, 1,6mMemFLPAPrn, and 1,6BnfAPrn-03 can be used, for example.

<<Light-Emitting Substance that Converts Triplet Excitation Energy into Light>>

Examples of the light-emitting substance that converts triplet excitation energy into light and can be used in the light-emitting layer 113 include substances that exhibit phosphorescent light (phosphorescent materials) and thermally activated delayed fluorescent (TADF) materials that exhibit thermally activated delayed fluorescence.

A phosphorescent substance is a compound that emits phosphorescent light but does not emit fluorescent light at a temperature higher than or equal to a low temperature (e.g., 77 K) and lower than or equal to room temperature (i.e., higher than or equal to 77 K and lower than or equal to 313 K). The phosphorescent substance preferably contains a metal element with large spin-orbit interaction, and can be an organometallic complex, a metal complex (platinum complex), or a rare earth metal complex, for example. Specifically, the phosphorescent substance preferably contains a transition metal element. It is preferable that the phosphorescent substance contain a platinum group element (ruthenium (Ru), rhodium (Rh), palladium (Pd), osmium (Os), iridium (Ir), or platinum (Pt)), especially iridium, in which case the probability of direct transition between the singlet ground state and the triplet excited state can be increased.

<<Phosphorescent Substance (from 450 nm to 570 nm, Blue or Green)>>

As examples of a phosphorescent substance which emits blue or green light and whose emission spectrum has a peak wavelength of greater than or equal to 450 nm and less than or equal to 570 nm, the following substances can be given.

Examples include organometallic complexes having a 4H-triazole ring, such as tris {2-[5-(2-methylphenyl)-4-(2,6-dimethylphenyl)-4H-1,2,4-triazol-3-yl-$N^2$]phenyl-κC}iridium(III) (abbreviation: $[Ir(mpptz\text{-}dmp)_3]$), tris(5-methyl-3,4-diphenyl-4H-1,2,4-triazolato)iridium(III) (abbreviation: $[Ir(Mptz)_3]$), tris[4-(3-biphenyl)-5-sopropyl-3-phenyl-4H-1,2,4-triazolato]iridium(III) (abbreviation: $[Ir(iPrptz\text{-}3b)_3]$), and tris[3-(5-biphenyl)-54 sopropyl-4-phenyl-4H-1,2,4-triazolato]iridium(III) (abbreviation: $[Ir(iPr5btz)_3]$); organometallic complexes having a 1H-triazole ring, such as tris[3-methyl-1-(2-methylphenyl)-5-phenyl-1H-1,2,4-triazolato]iridium(III) (abbreviation: $[Ir(Mptz1\text{-}mp)_3]$) and tris(1-methyl-5-phenyl-3-propyl-1H-1,2,4-triazolato)iridium(III) (abbreviation: $[Ir(Prptz1\text{-}Me)_3]$); organometallic complexes having an imidazole ring, such as fac-tris[1-(2,6-diisopropylphenyl)-2-phenyl-1H-imidazole]iridium(III) (abbreviation: $[Ir(iPrpmi)_3]$) and tris[3-(2,6-dimethylphenyl)-7-methylimidazo[1,2-f]phenanthridinato]iridium(III) (abbreviation: $[Ir(dmpimpt\text{-}Me)_3]$); and organometallic complexes in which a phenylpyridine derivative having an electron-withdrawing group is a ligand, such as bis[2-(4',6'-difluorophenyl)pyridinato-N,$C^2$]iridium(III) tetrakis(1-pyrazolyl)borate (abbreviation: FIr6), bis[2-(4',6'-difluorophenyl)pyridinato-N,$C^2$]iridium(III) picolinate (abbreviation: FIrpic), bis{2-[3',5'-bis(trifluoromethyl)phenyl]pyridinato-N,$C^2$}iridium(III) picolinate (abbreviation: $[Ir(CF_3ppy)_2(pic)]$), and bis[2-(4',6'-difluorophenyl)pyridinato-N,$C^2$]iridium(III) acetylacetonate (abbreviation: FIr(acac)).

<<Phosphorescent Substance (from 495 nm to 590 nm, Green or Yellow)>>

As examples of a phosphorescent substance which emits green or yellow light and whose emission spectrum has a peak wavelength of greater than or equal to 495 nm and less than or equal to 590 nm, the following substances can be given.

Examples of the phosphorescent substance include organometallic iridium complexes having a pyrimidine ring, such as tris(4-methyl-6-phenylpyrimidinato)iridium(III) (abbreviation: $[Ir(mppm)_3]$), tris(4-t-butyl-6-phenylpyrimidinato)iridium(III) (abbreviation: $[Ir(tBuppm)_3]$), (acetylacetonato)bis(6-methyl-4-phenylpyrimidinato)iridium(III) (abbreviation: $[Ir(mppm)_2(acac)]$), (acetylacetonato)bis(6-tert-butyl-4-phenylpyrimidinato)iridium(III) (abbreviation:

[Ir(tBuppm)$_2$(acac)]), (acetylacetonato)bis[6-(2-norbornyl)-4-phenylpyrimidinato]iridium(III) (abbreviation: [Ir(nbppm)$_2$(acac)]), (acetylacetonato)bis[5-methyl-6-(2-methylphenyl)-4-phenylpyrimidinato]iridium(III) (abbreviation: [Ir(mpmppm)$_2$(acac)]), (acetylacetonato) bis{4,6-dimethyl-2-[6-(2,6-dimethylphenyl)-4-pyrimidinyl-κN$^3$]phenyl-κC}iridium(III) (abbreviation: [Ir(dmppm-dmp)$_2$(acac)]), and (acetylacetonato)bis(4,6-diphenylpyrimidinato)iridium(III) (abbreviation: [Ir(dppm)$_2$(acac)]); organometallic iridium complexes having a pyrazine ring, such as (acetylacetonato)bis(3,5-dimethyl-2-phenylpyrazinato)iridium(III) (abbreviation: [Ir(mppr-Me)$_2$(acac)]) and (acetylacetonato)bis(5 sopropyl-3-methyl-2-phenylpyrazinato)iridium(III) (abbreviation: [Ir(mppr-iPr)$_2$(acac)]); organometallic iridium complexes having a pyridine ring, such as tris(2-phenylpyridinato-N,C$^{2'}$)iridium(III) (abbreviation: [Ir(ppy)$_3$]), bis(2-phenylpyridinato-N,C$^{2'}$)iridium(III) acetylacetonate (abbreviation: [Ir(ppy)$_2$(acac)]), bis(benzo[h]quinolinato)iridium(III) acetylacetonate (abbreviation: [Ir(bzq)$_2$(acac)]), tris(benzo[h]quinolinato)iridium(III) (abbreviation: [Ir(bzq)$_3$]), tris(2-phenylquinolinato-N,C$^{2'}$)iridium(III) (abbreviation: [Ir(pq)$_3$]), bis(2-phenylquinolinato-N,C$^{2'}$)iridium(III) acetylacetonate (abbreviation: [Ir(pq)$_2$(acac)]), bis[2-(2-pyridinyl-κN)phenyl-κC][2-(4-phenyl-2-pyridinyl-κN)phenyl-κC]iridium(III) (abbreviation: [Ir(ppy)$_2$(4dppy)]), bis[2-(2-pyridinyl-κN)phenyl-κC][2-(4-methyl-5-phenyl-2-pyridinyl-κN)phenyl-κC], [2-d$_3$-methyl-8-(2-pyridinyl-κN)benzofuro[2,3-b]pyridine-κC]bis[2-(5-d$_3$-methyl-2-pyridinyl-κN$^2$)phenyl-κC]iridium(III) (abbreviation: Ir(5mppy-d$_3$)$_2$(mbfpypy-d$_3$)), [2-(methyl-d3)-8-[4-(1-methylethyl-1-d)-2-pyridinyl-κN]benzofuro2, [3-b]pyridin-7-yl-κC]bis[5-(methyl-d3)-2-[5-(methyl-d$_3$)-2-pyridinyl-κN]phenyl-κC]iridium(III) (abbreviation: Ir(5mtpy-d6)$_2$(mbfpypy-iPr-d$_4$)), [2-d$_3$-methyl-(2-pyridinyl-κN)benzofuro[2,3-b]pyridine-κC]bis[2-(2-pyridinyl-κN)phenyl-κC]iridium(III) (abbreviation: Ir(ppy)$_2$(mbfpypy-d$_3$)), and [2-(4-methyl-5-phenyl-2-pyridinyl-κN)phenyl-κC]bis[2-(2-pyridinyl-κN)phenyl-κC]iridium(III) (abbreviation: Ir(ppy)$_2$(mdppy)); organometallic complexes such as bis(2,4-diphenyl-1,3-oxazolato-N,C$^{2'}$)iridium(III) acetylacetonate (abbreviation: [Ir(dpo)$_2$(acac)]), bis {2-[4'-(perfluorophenyl)phenyl]pyridinato-N,C$^2$}iridium(III) acetylacetonate (abbreviation: [Ir(p-PF-ph)$_2$(acac)]), and bis(2-phenylbenzothiazolato-N,C$^{2'}$)iridium(III) acetylacetonate (abbreviation: [Ir(bt)$_2$(acac)]); and a rare earth metal complex such as tris(acetylacetonato) (monophenanthroline)terbium(III) (abbreviation: [Tb(acac)$_3$(Phen)]).

<<Phosphorescent Substance (from 570 nm to 750 nm, Yellow or Red)>>

As examples of a phosphorescent substance which emits yellow or red light and whose emission spectrum has a peak wavelength of greater than or equal to 570 nm and less than or equal to 750 nm, the following substances can be given.

Examples of a phosphorescent substance include organometallic complexes having a pyrimidine ring, such as (diisobutyrylmethanato)bis[4,6-bis(3-methylphenyl)pyrimidinato]iridium(III) (abbreviation: [Ir(5mdppm)$_2$(dibm)]), bis[4,6-bis(3-methylphenyl)pyrimidinato](dipivaloylmethanato)iridium(III) (abbreviation: [Ir(5mdppm)$_2$(dpm)]), and (dipivaloylmethanato)bis[4,6-di(naphthalen-1-yl)pyrimidinato]iridium(III) (abbreviation: [Ir(d1npm)$_2$(dpm)]); organometallic complexes having a pyrazine ring, such as (acetylacetonato)bis(2,3,5-triphenylpyrazinato)iridium(III) (abbreviation: [Ir(tppr)$_2$(acac)]), bis(2,3,5-triphenylpyrazinato)(dipivaloylmethanato)iridium(III) (abbreviation: [Ir(tppr)$_2$(dpm)]), bis {4,6-dimethyl-2-[3-(3,5-dimethylphenyl)-5-phenyl-2-pyrazinyl-κN]phenyl-κC}(2,6-dimethyl-3,5-heptanedionato-κ$^2$O,O')iridium(III) (abbreviation: [Ir(dmdppr-P)$_2$(dibm)]), bis{4,6-dimethyl-2-[5-(4-cyano-2,6-dimethylphenyl)-3-(3,5-dimethylphenyl)-2-pyrazinyl-κN]phenyl-κC}(2,2,6,6-tetramethyl-3,5-heptanedionato-κ$^2$O,O')iridium(III) (abbreviation: [Ir(dmdppr-dmCP)$_2$(dpm)]), bis[2-(5-(2,6-dimethylphenyl)-3-(3,5-dimethylphenyl)-2-pyrazinyl-κN)-4,6-dimethylphenyl-κC](2,2',6,6'-tetramethyl-3,5-heptanedionato-K$^2$O,O')iridium(III) (abbreviation: [Ir(dmdppr-dmp)$_2$(dpm)]), (acetylacetonato)bis[2-methyl-3-phenylquinoxalinato-N,C$^{2'}$]iridium(III) (abbreviation: [Ir(mpq)$_2$(acac)]), (acetylacetonato)bis(2,3-diphenylquinoxalinato-N,C$^{2'}$)iridium(III) (abbreviation: [Ir(dpq)$_2$(acac)]), and (acetylacetonato)bis[2,3-bis(4-fluorophenyl)quinoxalinato]iridium(III) (abbreviation: [Ir(Fdpq)$_2$(acac)]); organometallic complexes having a pyridine ring, such as tris(1-phenylisoquinolinato-N,C$^{2'}$)iridium(III) (abbreviation: [Ir(piq)$_3$]), bis(1-phenylisoquinolinato-N,C$^{2'}$)iridium(III) acetylacetonate (abbreviation: [Ir(piq)$_2$(acac)]), and bis[4,6-dimethyl-2-(2-quinolinyl-κN)phenyl-κC](2,4-pentanedionato-κ$^2$O,O')iridium(III) (abbreviation: [Ir(dmpqn)$_2$(acac)]); a platinum complex such as 2,3,7,8,12,13,17,18-octaethyl-21H,23H-porphyrin platinum(II) (abbreviation: [PtOEP]); and rare earth metal complexes such as tris(1,3-diphenyl-1,3-propanedionato)(monophenanthroline)europium(III) (abbreviation: [Eu(DBM)$_3$(Phen)]) and tris[1-(2-thenoyl)-3,3,3-trifluoroacetonato](monophenanthroline)europium(III) (abbreviation: [Eu(TTA)$_3$(Phen)]).

<<TADF Material>>

Any of materials described below can be used as the TADF material. The TADF material is a material that has a small difference between its S1 and T1 levels (preferably less than or equal to 0.2 eV), enables up-conversion of a triplet excited state into a singlet excited state (i.e., reverse intersystem crossing) using a little thermal energy, and efficiently exhibits light (fluorescent light) from the singlet excited state. The thermally activated delayed fluorescence is efficiently obtained under the condition where the difference in energy between the triplet excitation energy level and the singlet excitation energy level is greater than or equal to 0 eV and less than or equal to 0.2 eV, preferably greater than or equal to 0 eV and less than or equal to 0.1 eV. Note that delayed fluorescent light by the TADF material refers to light emission having a spectrum similar to that of normal fluorescent light and an extremely long lifetime. The lifetime is longer than or equal to $1\times10^{-6}$ seconds, preferably longer than or equal to $1\times10^{-3}$ seconds.

Examples of the TADF material include fullerene, a derivative thereof, an acridine derivative such as proflavine, and eosin. Other examples thereof include a metal-containing porphyrin such as a porphyrin containing magnesium (Mg), zinc (Zn), cadmium (Cd), tin (Sn), platinum (Pt), indium (In), or palladium (Pd). Examples of the metal-containing porphyrin include a protoporphyrin-tin fluoride complex (abbreviation: $SnF_2$(Proto IX)), a mesoporphyrin-tin fluoride complex (abbreviation: $SnF_2$(Meso IX)), a hematoporphyrin-tin fluoride complex (abbreviation: $SnF_2$(Hemato IX)), a coproporphyrin tetramethyl ester-tin fluoride complex (abbreviation: $SnF_2$(Copro III-4Me)), an octaethylporphyrin-tin fluoride complex (abbreviation: $SnF_2$(OEP)), an etioporphyrin-tin fluoride complex (abbreviation: $SnF_2$(Etio I)), and an octaethylporphyrin-platinum chloride complex (abbreviation: $PtCl_2$OEP).

[Chemical Formula 3]
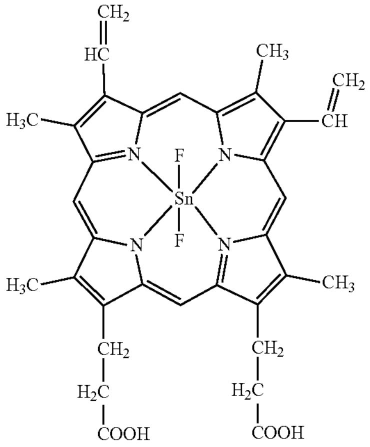
$SnF_2$(Proto IX)
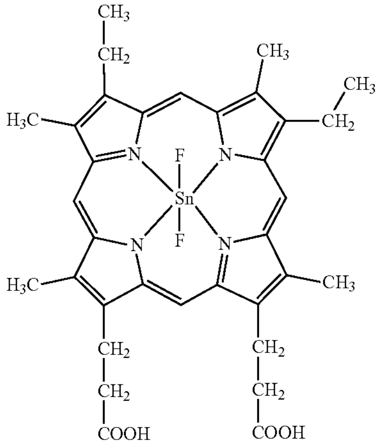
$SnF_2$(Meso IX)
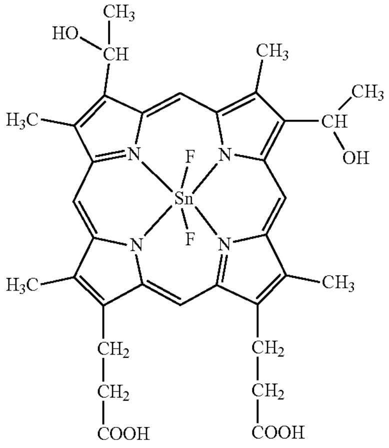
$SnF_2$(Hemato IX)
-continued
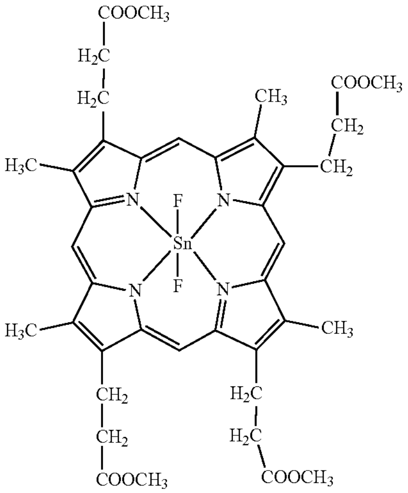
$SnF_2$(Copro III-4Me)
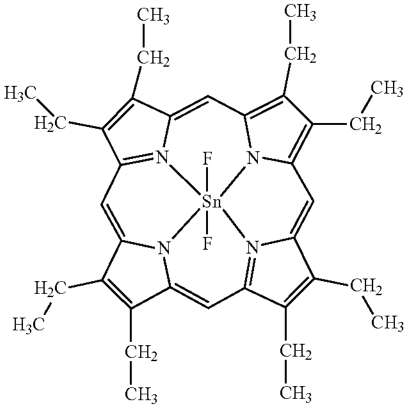
$SnF_2$(OEP)
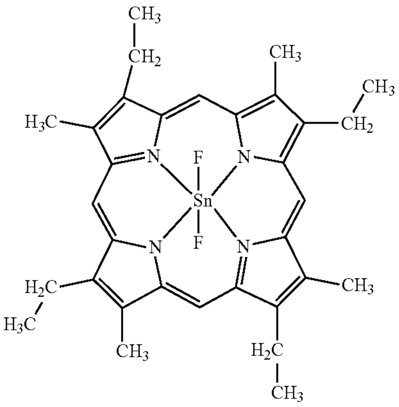
$SnF_2$(Etio I)

-continued

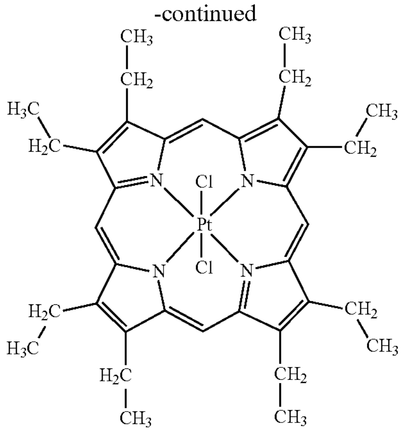

PtCl2OEP

Additionally, a heteroaromatic compound having a π-electron rich heteroaromatic compound and a π-electron deficient heteroaromatic compound, such as 2-(biphenyl-4-yl)-4,6-bis(12-phenylindolo[2,3-a]carbazol-11-yl)-1,3,5-triazine (abbreviation: PIC-TRZ), 2-{4-[3-(N-phenyl-9H-carbazol-3-yl)-9H-carbazol-9-yl]phenyl}-4,6-diphenyl-1,3,5-triazine (abbreviation: PCCzPTzn), 2-[4-(1 OH-phenoxazin-10-yl)phenyl]-4,6-diphenyl-1,3,5-triazine (abbreviation: PXZ-TRZ), 3-[4-(5-phenyl-5,10-dihydrophenazin-10-yl)phenyl]-4,5-diphenyl-1,2,4-triazole (abbreviation: PPZ-3TPT), 3-(9,9-dimethyl-9H-acridin-10-yl)-9H-xanthen-9-one (abbreviation: ACRXTN), bis[4-(9,9-dimethyl-9,10-dihydroacridine)phenyl]sulfone (abbreviation: DMAC-DPS), 10-phenyl-10H,10'H-spiro[acridin-9,9'-anthracen]-10'-one (abbreviation: ACRSA), 4-(9'-phenyl-3,3'-bi-9H-carbazol-9-yl)benzofuro[3,2-d]pyrimidine (abbreviation: 4PCCzBfpm), 4-[4-(9'-phenyl-3,3'-bi-9H-carbazol-9-yl)phenyl]benzofuro[3,2-d]pyrimidine (abbreviation: 4PCCzPBfpm), or 9-[3-(4,6-diphenyl-1,3,5-triazin-2-yl)phenyl]-9'-phenyl-2,3'-bi-9H-carbazole (abbreviation: mPCCzPTzn-02) may be used.

Note that a substance in which a π-electron rich heteroaromatic compound is directly bonded to a π-electron deficient heteroaromatic compound is particularly preferable because both the donor property of the π-electron rich heteroaromatic compound and the acceptor property of the π-electron deficient heteroaromatic compound are improved and the energy difference between the singlet excited state and the triplet excited state becomes small. As the TADF material, a TADF material in which the singlet and triplet excited states are in thermal equilibrium (TADF100) may be used. Since such a TADF material enables a short emission lifetime (excitation lifetime), the efficiency of a light-emitting element in a high-luminance region can be less likely to decrease.

[Chemical Formula 4]

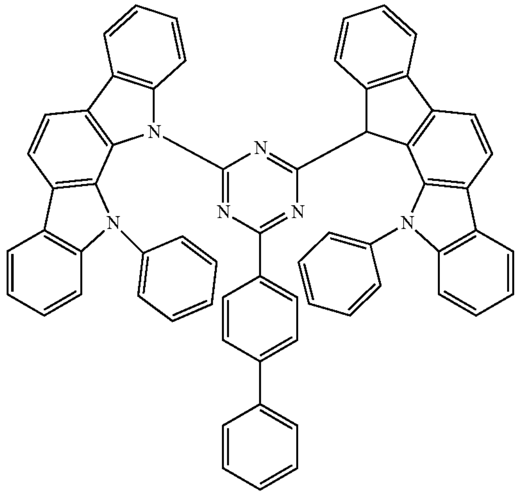

PIC-TRZ

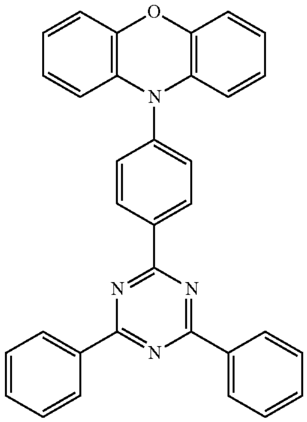

PXZ-TRZ

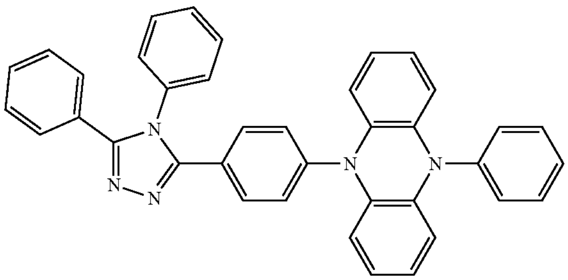

PPZ-3TPT

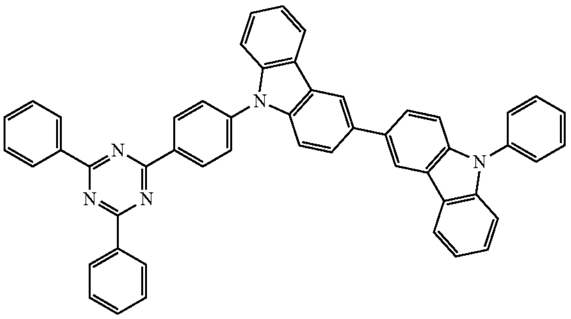

PCCzPTzn

-continued

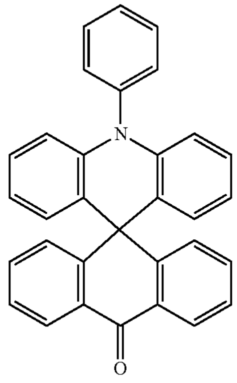

ACRSA

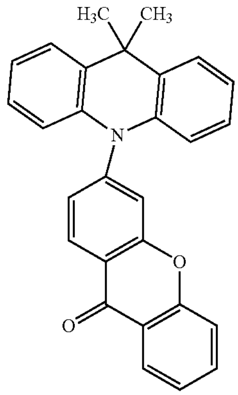

ACRXTN

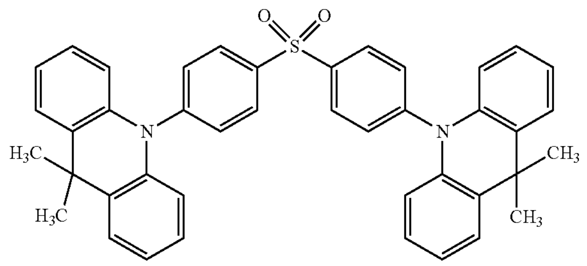

DMAC-DPS

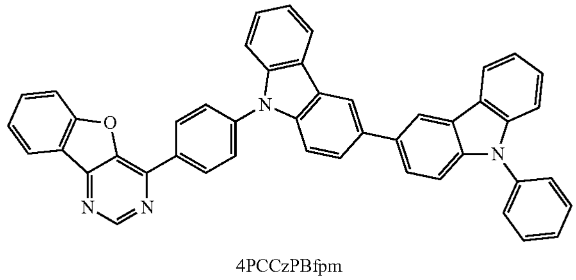

4PCCzPBfpm

-continued

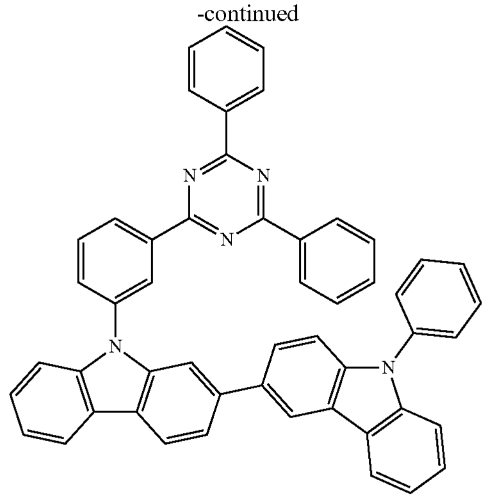

mPCCzPTzn-02

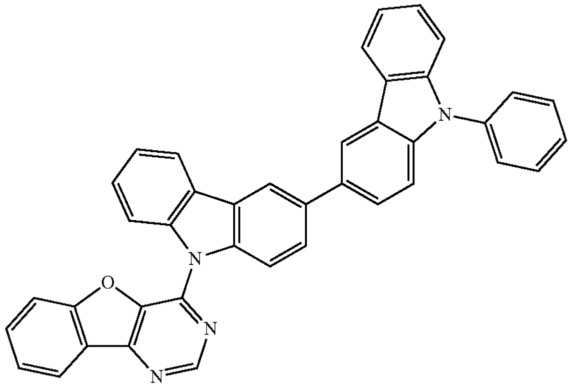

4PCCzBfpm

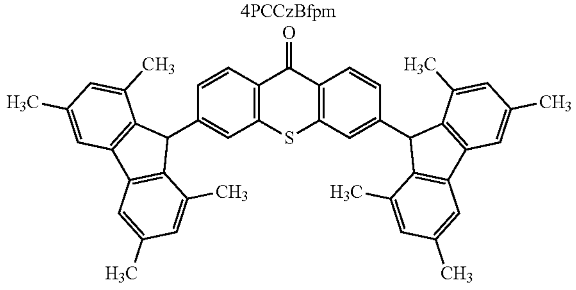

TADF100

In addition to the above, another example of a material having a function of converting triplet excitation energy into light is a nano-structure of a transition metal compound having a perovskite structure. In particular, a nano-structure of a metal halide perovskite material is preferable. The nano-structure is preferably a nanoparticle or a nanorod.

As the organic compound (e.g., the host material) used in combination with the above-described light-emitting substance (guest material) in the light-emitting layers (113, 113*a*, 113*b*, and 113*c*), one or more kinds selected from substances having a larger energy gap than that of the light-emitting substance (guest material) can be used.

<<Host Material for Fluorescent Light>>

In the case where the light-emitting substance used in the light-emitting layers (113, 113*a*, 113*b*, and 113*c*) is a fluorescent substance, an organic compound (a host material) used in combination with the fluorescent substance is preferably an organic compound that has a high energy level in a singlet excited state and has a low energy level in a triplet excited state or an organic compound having a high fluorescence quantum yield. Therefore, the hole-transport material (described above) and the electron-transport material (described below) shown in this embodiment, for example, can be used as long as they are organic compounds that satisfy such a condition.

In terms of a preferred combination with the light-emitting substance (fluorescent substance), examples of the organic compound (host material), some of which overlap the above specific examples, include fused polycyclic aromatic compounds such as an anthracene derivative, a tetracene derivative, a phenanthrene derivative, a pyrene derivative, a chrysene derivative, and a dibenzo[g,p] chrysene derivative.

Specific examples of the organic compound (host material) that is preferably used in combination with the fluorescent substance include 9-phenyl-3-[4-(10-phenyl-9-anthryl)phenyl]-9H-carbazole (abbreviation: PCzPA), 3,6-diphenyl-9-[4-(10-phenyl-9-anthryl)phenyl]-9H-carbazole (abbreviation: DPCzPA), 3-[4-(1-naphthyl)-phenyl]-9-phenyl-9H-carbazole (abbreviation: PCPN), 9,10-diphenylanthracene (abbreviation: DPAnth), N,N-diphenyl-9-[4-(10-phenyl-9-anthryl)phenyl]-9H-carbazol-3-amine (abbreviation: CzA1PA), 4-(10-phenyl-9-anthryl)triphenylamine (abbreviation: DPhPA), YGAPA, PCAPA, N,9-diphenyl-N-{4-[4-(10-phenyl-9-anthryl)phenyl]phenyl}-9H-carbazol-3-amine (abbreviation: PCAPBA), N-(9,10-diphenyl-2-anthryl)-N, 9-diphenyl-9H-carbazol-3-amine (abbreviation: 2PCAPA), 6,12-dimethoxy-5,11-diphenylchrysene, N,N,N',N',N",N",N"',N"'-octaphenyldibenzo[g,p] chrysene-2,7,10,15-tetraamine (abbreviation: DBC1), 9-[4-(10-phenyl-9-anthracenyl)phenyl]-9H-carbazole (abbreviation: CzPA), 7-[4-(10-phenyl-9-anthryl)phenyl]-7H-dibenzo[c,g]carbazole (abbreviation: cgDBCzPA), 6-[3-(9,10-diphenyl-2-anthryl)phenyl]-benzo[b]naphtho[1,2-d] furan (abbreviation: 2mBnfPPA), 9-phenyl-10-{4-(9-phenyl-9H-fluoren-9-yl)biphenyl-4'-yl}anthracene (abbreviation: FLPPA), 9,10-bis(3,5-diphenylphenyl)anthracene (abbreviation: DPPA), 9,10-di(2-naphthyl)anthracene (abbreviation: DNA), 2-tert-butyl-9,10-di(2-naphthyl) anthracene (abbreviation: t-BuDNA), 9-(1-naphthyl)-10-(2-naphthyl)anthracene (abbreviation: α,β-ADN), 2-(10-phenylanthracen-9-yl)dibenzofuran, 2-(10-phenyl-9-anthracenyl)-benzo[b]naphtho[2,3-d]furan (abbreviation: Bnf(II)PhA), 9-(1-naphthyl)-10-[4-(2-naphthyl)phenyl]anthracene (abbreviation: αN-βNPAnth), 9-(2-naphthyl)-10-[3-(2-naphthyl)phenyl]anthracene (abbreviation: βN-mβNPAnth), 1-[4-(10-[1,-biphenyl]-4-yl-9-anthracenyl) phenyl]-2-ethyl-1H-benzimidazole (abbreviation: EtBImPBPhA), 9,9'-bianthryl (abbreviation: BANT), 9,9'-(stilbene-3,3'-diyl)diphenanthrene (abbreviation: DPNS), 9,9'-(stilbene-4,4'-diyl)diphenanthrene (abbreviation: DPNS2), 1,3,5-tri(1-pyrenyl)benzene (abbreviation: TPB3), 5,12-diphenyltetracene, and 5,12-bis(biphenyl-2-yl)tetracene.

<<Host Material for Phosphorescence>>

In the case where the light-emitting substance used in the light-emitting layers (113, 113*a*, 113*b*, and 113*c*) is a phosphorescent substance, an organic compound having triplet excitation energy (an energy difference between a ground state and a triplet excited state) which is higher than that of the light-emitting substance is preferably selected as the organic compound (host material) used in combination with the phosphorescent substance. Note that when a plurality of organic compounds (e.g., a first host material and a second host material (or an assist material)) are used in combination with a light-emitting substance so that an exciplex is formed, the plurality of organic compounds are preferably mixed with the phosphorescent substance.

With such a structure, light emission can be efficiently obtained by exciplex-triplet energy transfer (ExTET), which is energy transfer from an exciplex to a light-emitting substance. Note that a combination of the plurality of organic compounds that easily forms an exciplex is preferred, and it is particularly preferable to combine a compound that easily accepts holes (hole-transport material) and a compound that easily accepts electrons (electron-transport material).

From the viewpoint of a preferred combination with the light-emitting substance (phosphorescent substance), the examples of the organic compounds (the host material and the assist material), but some of them partly overlapping the above specific examples, include an aromatic amine (an organic compound having an aromatic amine skeleton), a carbazole derivative (an organic compound having a carbazole ring), a dibenzothiophene derivative (an organic compound having a dibenzothiophene ring), a dibenzofuran derivative (an organic compound having a dibenzofuran ring), an oxadiazole derivative (an organic compound having an oxadiazole ring), a triazole derivative (an organic compound having an triazole ring), a benzimidazole derivative (an organic compound having an benzimidazole ring), a quinoxaline derivative (an organic compound having a quinoxaline ring), a dibenzoquinoxaline derivative (an organic compound having a dibenzoquinoxaline ring), a pyrimidine derivative (an organic compound having a pyrimidine ring), a triazine derivative (an organic compound having a triazine ring), a pyridine derivative (an organic compound having a pyridine ring), a bipyridine derivative (an organic compound having a bipyridine ring), a phenanthroline derivative (an organic compound having a phenanthroline ring), a furodiazine derivative (an organic compound having a furodiazine ring), and zinc- or aluminum-based metal complexes.

Among the above organic compounds, specific examples of the aromatic amine and the carbazole derivative, which are organic compounds having a high hole-transport property, are the same as the specific examples of the hole-transport materials described above, and those materials are preferable as the host material.

Among the above organic compounds, specific examples of the dibenzothiophene derivative and the dibenzofuran derivative, which are organic compounds having a high hole-transport property, include 4-{3-[3-(9-phenyl-9H-fluoren-9-yl)phenyl]phenyl}dibenzofuran (abbreviation: mmDBFFLBi-II), 4,4',4"-(benzene-1,3,5-triyl)tri(dibenzofuran) (abbreviation: DBF3P-II), DBT3P-II, 2,8-diphenyl-4-[4-(9-phenyl-9H-fluoren-9-yl)phenyl]dibenzothiophene (abbreviation: DBTFLP-III), 4-[4-(9-phenyl-9H-fluoren-9-yl)phenyl]-6-phenyldibenzothiophene (abbreviation: DBTFLP-IV), and 4-[3-(triphenylen-2-yl)phenyl]dibenzothiophene (abbreviation: mDBTPTp-II). Such derivatives are preferable as the host material.

Other examples of preferred host materials include metal complexes having an oxazole-based or thiazole-based ligand, such as bis[2-(2-benzoxazolyl)phenolato]zinc(II) (abbreviation: ZnPBO) and bis[2-(2-benzothiazolyl)phenolato]zinc(II) (abbreviation: ZnBTZ).

Among the above organic compounds, specific examples of the oxadiazole derivative, the triazole derivative, the benzimidazole derivative, the quinoxaline derivative, the dibenzoquinoxaline derivative, the quinazoline derivative, and the phenanthroline derivative, which are organic compounds having a high electron-transport property, include:

an organic compound including a heteroaromatic ring having a polyazole ring such as 2-(4-biphenylyl)-5-(4-tert-butylphenyl)-1,3,4-oxadiazole (abbreviation: PBD), 1,3-bis [5-(p-tert-butylphenyl)-1,3,4-oxadiazol-2-yl]benzene (abbreviation: OXD-7), 9-[4-(5-phenyl-1,3,4-oxadiazol-2-yl)phenyl]-9H-carbazole (abbreviation: CO11), 3-(4-biphenylyl)-4-phenyl-5-(4-tert-butylphenyl)-1,2,4-triazole (abbreviation: TAZ), 2,2',2"-(1,3,5-benzenetriyl)tris(1-phenyl-1H-benzimidazole) (abbreviation: TPBI), 2-[3-(dibenzothiophen-4-yl)phenyl]-1-phenyl-1H-benzimidazole (abbreviation: mDBTBIm-II), or 4,4'-bis(5-methylbenzoxazol-2-yl)stilbene (abbreviation: BzOS); an organic compound including a heteroaromatic ring having a pyridine ring such as bathophenanthroline (abbreviation: BPhen), bathocuproine (abbreviation: BCP), 2,9-di(naphthalen-2-yl)-4,7-diphenyl-1,10-phenanthroline (abbreviation: NBphen), 2,2-(1,3-phenylene)bis[9-phenyl-1,10-phenanthroline](abbreviation: mPPhen2P), or 2,2'-[biphenyl]-4,4'-diylbis[1,10-phenanthroline] (abbreviation: Phen2BP); 2-[3-(dibenzothiophen-4-yl)phenyl]dibenzo[f,h] quinoxaline (abbreviation: 2mDBTPDB q-II); 2-[3'-(dibenzothiophen-4-yl)biphenyl-3-yl]dibenzo[f,h]quinoxaline (abbreviation: 2mDBTBPDBq-II); 2-[3'-(9H-carbazol-9-yl) biphenyl-3-yl]dibenzo[f,h]quinoxaline (abbreviation: 2mCzBPDBq); 2-[4-(3,6-diphenyl-9H-carbazol-9-yl)phenyl]dibenzo[f,h]quinoxaline (abbreviation: 2CzPDBq-III); 7-[3-(dibenzothiophen-4-yl)phenyl]dibenzo[f,h]quinoxaline (abbreviation: 7mDBTPDBq-II); 6-[3-(dibenzothiophen-4-yl)phenyl]dibenzo[f,h]quinoxaline (abbreviation: 6mDBTPDBq-II); 2-{4-[9,10-di(2-naphthyl)-2-anthryl]phenyl}-1-phenyl-1H-benzimidazole (abbreviation: ZADN); and 2-4'-(9-phenyl-9H-carbazol-3-yl)-3,1'-biphenyl-1-yl] dibenzo[f,h]quinoxaline (abbreviation: 2mpPCBPDBq). Such organic compounds are preferable as the host material.

Among the above organic compounds, specific examples of the pyridine derivative, the diazine derivative (e.g., the pyrimidine derivative, the pyrazine derivative, and the pyridazine derivative), the triazine derivative, the furodiazine derivative, which are organic compounds having a high electron-transport property, include organic compounds including a heteroaromatic ring having a diazine ring such as 4,6-bis[3-(phenanthren-9-yl)phenyl]pyrimidine (abbreviation: 4,6mPnP2Pm), 4,6-bis[3-(4-dibenzothienyl)phenyl] pyrimidine (abbreviation: 4,6mDBTP2Pm-II), 4,6-bis[3-(9H-carbazol-9-yl)phenyl]pyrimidine (abbreviation: 4,6mCzP2Pm), 2-{4-[3-(N-phenyl-9H-carbazol-3-yl)-9H-carbazol-9-yl]phenyl}-4,6-diphenyl-1,3,5-triazine (abbreviation: PCCzPTzn), 9-[3-(4,6-diphenyl-1,3,5-triazin-2-yl) phenyl]-9'-phenyl-2,3'-bi-9H-carbazole (abbreviation: mPCCzPTzn-02), 3,5-bis[3-(9H-carbazol-9-yl)phenyl]pyridine (abbreviation: 35DCzPPy), 1,3,5-tri[3-(3-pyridyl)phenyl]benzene (abbreviation: TmPyPB), 9,9'-[pyrimidine-4,6-diylbis(biphenyl-3,3'-diyl)]bis(9H-carbazole) (abbreviation: 4,6mCzBP2Pm), 2-[3'-(9,9-dimethyl-9H-fluoren-2-yl)-1,1'-biphenyl-3-yl]-4,6-diphenyl-1,3,5-triazine (abbreviation: mFBPTzn), 8-(1,1'-biphenyl-4-yl)-4-[3-(dibenzothiophen-4-yl)phenyl]-[1]benzofuro[3,2-d]pyrimidine (abbreviation: 8BP-4mDBtPBfpm), 9-[3'-(dibenzothiophen-4-yl)biphenyl-3-yl]naphtho[1',2':4,5]furo[2,3-b]pyrazine (abbreviation: 9mDBtBPNfpr), 9-[(3'-dibenzothiophen-4-yl)biphenyl-4-yl]naphtho[1',2':4,5]furo[2,3-b]pyrazine (abbreviation: 9pmDBtBPNfpr), 5-[3-(4,6-diphenyl-1,3,5-triazin-2-yl) phenyl]-7,7-dimethyl-5H,7H-indeno[2,1-b]carbazole (abbreviation: mINc(II)PTzn), 2-[3'-(triphenylen-2-yl)-1,1'-biphenyl-3-yl]-4,6-diphenyl-1,3,5-triazine (abbreviation: mTpBPTzn), 2-[(1,1'-biphenyl)-4-yl]-4-phenyl-6-[9,9'-spirobi(9H-fluoren)-2-yl]-1,3,5-triazine (abbreviation: BP-SFTzn), 2,6-bis(4-naphthalen-1-ylphenyl)-4-[4-(3-pyridyl)phenyl]pyrimidine (abbreviation: 2,4NP-6PyPPm), 9-[4-(4,6-diphenyl-1,3,5-triazin-2-yl)-2-dibenzothiophenyl]-2-phenyl-9H-carbazole (abbreviation: PCDBfTzn), 2-[1,1'-biphenyl]-3-yl-4-phenyl-6-(8-[1,1': 4',1"-terphenyl]-4-yl-1-dibenzofuranyl)-1,3,5-triazine (abbreviation: mBP-TPDBfTzn), 6-(1,1'-biphenyl-3-yl)-4-[3,5-bis(9H-carbazol-9-yl)phenyl)-2-phenylpyrimidine (abbreviation: 6mBP-4Cz2PPm), and 4-[3,5-bis(9H-carbazol-9-yl)phenyl]-2-phenyl-6-(1,1'-biphenyl-4-yl)pyrimidine (abbreviation: 6BP-4Cz2PPm), and those materials are preferable as the host material.

Among the above organic compounds, specific examples of metal complexes that are organic compounds having a high electron-transport property include zinc- or aluminum-based metal complexes, such as tris(8-quinolinolato)aluminum(III) (abbreviation: Alq), tris(4-methyl-8-quinolinolato) aluminum(III) (abbreviation: $Almq_3$), bis(10-hydroxybenzo [h]quinolinato)beryllium(II) (abbreviation: $BeBq_2$), bis(2-methyl-8-quinolinolato)(4-phenylphenolato)aluminum(III) (abbreviation: BAlq), and bis(8-quinolinolato)zinc(II) (abbreviation: Znq), and metal complexes having a quinoline ring or a benzoquinoline ring. Such metal complexes are preferable as the host material.

Moreover, high-molecular compounds such as poly(2,5-pyridinediyl) (abbreviation: PPy), poly[(9,9-dihexylfluorene-2,7-diyl)-co-(pyridine-3,5-diyl)] (abbreviation: PF-Py), and poly[(9,9-dioctylfluorene-2,7-diyl)-co-(2,2'-bipyridine-6,6'-diyl)] (abbreviation: PF-BPy) are preferable as the host material.

Examples of organic compounds having bipolar properties, a high hole-transport property and a high electron-transport property, which can be used as the host material, include the organic compounds having a diazine ring such as 9-phenyl-9'-(4-phenyl-2-quinazolinyl)-3,3'-bi-9H-carbazole (abbreviation: PCCzQz), 2-[4'-(9-phenyl-9H-carbazol-3-yl)-3,1'-biphenyl-1-yl]dibenzo[f,h]quinoxaline (abbreviation: 2mpPCBPDBq), 5-[3-(4,6-diphenyl-1,3,5-triazin-2yl) phenyl]-7,7-dimethyl-5H, 7H-indeno[2,1-b]carbazole (abbreviation: mINc(II)PTzn), 11-(4-[1,1'-biphenyl]-4-yl-6-phenyl-1,3,5-triazin-2-yl)-11,12-dihydro-12-phenyl-indolo [2,3-a]carbazole (abbreviation: BP-Icz(II)Tzn), and 7-[4-(9-phenyl-9H-carbazol-2-yl)quinazolin-2-yl]-7H-dibenzo[c,g] carbazole (abbreviation: PC-cgDBCzQz).

<Electron-Transport Layer>

The electron-transport layers (114, 114*a*, and 114*b*) transport the electrons, which are injected from the second electrode 102 and the charge-generation layers (106, 106*a*, and 106*b*) by electron-injection layers (115, 115*a*, and 115*b*) described later, to the light-emitting layers (113, 113*a*, and 113*b*). The heat resistance of the light-emitting device of one embodiment of the present invention can be improved by including the stacked electron-transport layers. The electron-transport material used in the electron-transport layers (114, 114*a*, and 114*b*) is preferably a substance having an electron mobility of $1\times10^{-6}$ $cm^2/Vs$ or higher in the case where the square root of the electric field strength [V/cm] is 600. Note that any other substance can also be used as long as the substance have an electron-transport property higher than a hole-transport property. The electron-transport layers (114, 114*a*, and 114*b*) can function even with a single-layer structure and may have a stacked-layer structure including two or more layers. When a photolithography process is performed over the electron-transport layer including the above-described mixed material, which has heat resistance, an adverse effect of the thermal process on the device characteristics can be reduced.

<<Electron-Transport Material>>

As the electron-transport material that can be used for the electron-transport layers (114, 114*a*, and 114*b*), an organic compound having a high electron-transport property can be used, and for example, a heteroaromatic compound can be used. The term heteroaromatic compound refers to a cyclic compound including at least two different kinds of elements in a ring. Examples of cyclic structures include a three-membered ring, a four-membered ring, a five-membered ring, a six-membered ring, and the like, among which a five-membered ring and a six-membered ring are particularly preferred. The elements included in the heteroaromatic compound are preferably one or more of nitrogen, oxygen, and sulfur, in addition to carbon. In particular, a heteroaromatic compound containing nitrogen (a nitrogen-containing heteroaromatic compound) is preferred, and any of materials having a high electron-transport property (electron-transport materials), such as a nitrogen-containing heteroaromatic compound and a π-electron deficient heteroaromatic compound including the nitrogen-containing heteroaromatic compound, is preferably used.

The heteroaromatic compound is an organic compound including at least one heteroaromatic ring.

The heteroaromatic ring includes any one of a pyridine ring, a diazine ring, a triazine ring, a polyazole ring, an oxazole ring, a thiazole ring, and the like. A heteroaromatic ring having a diazine ring includes a heteroaromatic ring having a pyrimidine ring, a pyrazine ring, a pyridazine ring, or the like. A heteroaromatic ring having a polyazole ring includes a heteroaromatic ring having an imidazole ring, a triazole ring, or an oxadiazole ring.

The heteroaromatic ring includes a fused heteroaromatic ring having a fused ring structure. Examples of the fused heteroaromatic ring include a quinoline ring, a benzoquinoline ring, a quinoxaline ring, a dibenzoquinoxaline ring, a quinazoline ring, a benzoquinazoline ring, a dibenzoquinazoline ring, a phenanthroline ring, a furodiazine ring, and a benzimidazole ring.

Examples of the heteroaromatic compound having a five-membered ring structure, which is a heteroaromatic compound including carbon and one or more of nitrogen, oxygen, and sulfur, include a heteroaromatic compound having an imidazole ring, a heteroaromatic compound having a triazole ring, a heteroaromatic compound having an oxazole ring, a heteroaromatic compound having an oxadiazole ring, a heteroaromatic compound having a thiazole ring, a heteroaromatic compound having a benzimidazole ring, and the like.

Examples of the heteroaromatic compound having a six-membered ring structure, which is a heteroaromatic compound including carbon and one or more of nitrogen, oxygen, and sulfur, include a heteroaromatic compound having a heteroaromatic ring, such as a pyridine ring, a diazine ring (a pyrimidine ring, a pyrazine ring, a pyridazine ring, or the like), a triazine ring, or a polyazole ring. Other examples include a heteroaromatic compound having a bipyridine structure, a heteroaromatic compound having a terpyridine structure, and the like, which are included in examples of a heteroaromatic compound in which pyridine rings are connected.

Examples of the heteroaromatic compound having a fused ring structure including the above six-membered ring structure in a part include a heteroaromatic compound having a fused heteroaromatic ring such as a quinoline ring, a benzoquinoline ring, a quinoxaline ring, a dibenzoquinoxaline ring, a phenanthroline ring, a furodiazine ring (including a structure in which an aromatic ring is fused to a furan ring of a furodiazine ring), or a benzimidazole ring.

Specific examples of the above-described heteroaromatic compound having a five-membered ring structure (a polyazole ring (including an imidazole ring, a triazole ring, or an oxadiazole ring), an oxazole ring, a thiazole ring, or a benzimidazole ring) include 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 9-[4-(5-phenyl-1,3,4-oxadiazol-2-yl)phenyl]-9H-carbazole (abbreviation: CO11), 3-(4-biphenylyl)-4-phenyl-5-(4-tert-butylphenyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), 2,2',2''-(1,3,5-benzenetriyl)tris(1-phenyl-1H-benzimidazole) (abbreviation: TPBI), 2-[3-(dibenzothiophen-4-yl)phenyl]-1-phenyl-1H-benzimidazole (abbreviation: mDBTBIm-II), and 4,4'-bis(5-methylbenzoxazol-2-yl)stilbene (abbreviation: BzOS).

Specific examples of the above-described heteroaromatic compound having a six-membered ring structure (including a heteroaromatic ring having a pyridine ring, a diazine ring, a triazine ring, or the like) include: a heteroaromatic compound including a heteroaromatic ring having a pyridine ring, such as 3,5-bis[3-(9H-carbazol-9-yl)phenyl]pyridine (abbreviation: 35DCzPPy) or 1,3,5-tri[3-(3-pyridyl)phenyl]benzene (abbreviation: TmPyPB); a heteroaromatic compound including a heteroaromatic ring having a triazine ring, such as 2-{4-[3-(N-phenyl-9H-carbazol-3-yl)-9H-carbazol-9-yl]phenyl}-4,6-diphenyl-1,3,5-triazine (abbreviation: PCCzPTzn), 9-[3-(4,6-diphenyl-1,3,5-triazin-2-yl)phenyl]-9'-phenyl-2,3'-bi-9H-carbazole (abbreviation: mPCCzPTzn-02), 5-[3-(4,6-diphenyl-1,3,5-triazin-2-yl)phenyl]-7,7-dimethyl-5H,7H-indeno[2,1-b]carbazole (abbreviation: mINc(II)PTzn), 2-[3'-(triphenylen-2-yl)-1,1'-biphenyl-3-yl]-4,6-diphenyl-1,3,5-triazine (abbreviation: mTpBPTzn), 2-[(1,1'-biphenyl)-4-yl]-4-phenyl-6-[9,9'-spirobi(9H-fluoren)-2-yl]-1,3,5-triazine (abbreviation: BP-SFTzn), 2,6-bis(4-naphthalen-1-ylphenyl)-4-[4-(3-pyridyl)phenyl]pyrimidine (abbreviation: 2,4NP-6PyPPm), 9-[4-(4,6-diphenyl-1,3,5-triazin-2-yl)-2-dibenzothiophenyl]-2-phenyl-9H-carbazole (abbreviation: PCDBfTzn), 2-[1,1'-biphenyl]-3-yl-4-phenyl-6-(8-[1,1':4',1''-terphenyl]-4-yl-1-dibenzofuranyl)-1,3,5-triazine (abbreviation: mBP-TPDBfTzn), 2-{3-[3-(dibenzothiophen-4-yl)phenyl]phenyl}-4,6-diphenyl-1,3,5-triazine (abbreviation: mDBtBPTzn), or mFBPTzn; and a heteroaromatic compound including a heteroaromatic ring having a diazine (pyrimidine) ring, such as 4,6-bis[3-(phenanthren-9-yl)phenyl]pyrimidine (abbreviation: 4,6mPnP2Pm), 4,6-bis[3-(4-dibenzothienyl)phenyl]pyrimidine (abbreviation: 4,6mDBTP2Pm-II), 4,6-bis[3-(9H-carbazol-9-yl)phenyl]pyrimidine (abbreviation: 4,6mCzP2Pm), 4,6mCzBP2Pm, 6-(1,1'-biphenyl-3-yl)-4-[3,5-bis(9H-carbazol-9-yl)phenyl]-2-phenylpyrimidine (abbreviation: 6mBP-4Cz2PPm), 4-[3,5-bis(9H-carbazol-9-yl)phenyl]-2-phenyl-6-(1,1'-biphenyl-4-yl)pyrimidine (abbreviation: 6BP-4Cz2PPm), 4-[3-(dibenzothiophen-4-yl)phenyl]-8-(naphthalen-2-yl)-[1]benzofuro[3,2-d]pyrimidine (abbreviation: 8(3N-4mDBtPBfpm), 8BP-4mDBtPBfpm, 9mDBtBPNfpr, 9pmDBtBPNfpr, 3,8-bis[3-(dibenzothiophen-4-yl)phenyl]benzofuro[2,3-b]pyrazine (abbreviation: 3,8mDBtP2Bfpr), 4,8-bis[3-(dibenzothiophen-4-yl)phenyl]-[1]benzofuro[3,2-d]pyrimidine (abbreviation: 4,8mDBtP2Bfpm), 8-[3'-(dibenzothiophen-4-yl)(1,1'-biphenyl-3-yl)]naphtho[1',2':4,5]furo[3,2-d]pyrimidine (abbreviation: 8mDBtBPNfpm), or 8-[(2,2'-binaphthalen)-6-yl]-4-[3-(dibenzothiophen-4-yl)phenyl]-[1]benzofuro[3,2-d]

pyrimidine (abbreviation: 8(βN2)-4mDBtPBfpm). Note that the above aromatic compounds including a heteroaromatic ring include a heteroaromatic compound having a fused heteroaromatic ring.

Other examples include heteroaromatic compounds including a heteroaromatic ring having a diazine (pyrimidine) ring, such as 2,2'-(pyridine-2,6-diyl)bis(4-phenylbenzo[h]quinazoline) (abbreviation: 2,6(P-Bqn)$_2$Py), 2,2'-(2,2'-bipyridine-6,6'-diyl)bis(4-phenylbenzo[h]quinazoline) (abbreviation: 6,6'(P-Bqn)$_2$BPy), 2,2'-(pyridine-2,6-diyl)bis{4-[4-(2-naphthyl)phenyl]-6-phenylpyrimidine} (abbreviation: 2,6(NP-PPm)$_2$Py), or 6-(1,1'-biphenyl-3-yl)-4-[3,5-bis(9H-carbazol-9-yl)phenyl]-2-phenylpyrimidine (abbreviation: 6mBP-4Cz2PPm) and a heteroaromatic compound including a heteroaromatic ring having a triazine ring, such as 2,4,6-tris(3'-(pyridin-3-yl)biphenyl-3-yl)-1,3,5-triazine (abbreviation: TmPPPyTz), 2,4,6-tris(2-pyridyl)-1,3,5-triazine (abbreviation: 2Py3Tz), or 2-[3-(2,6-dimethyl-3-pyridinyl)-5-(9-phenanthrenyl)phenyl]-4,6-diphenyl-1,3,5-triazine (abbreviation: mPn-mDMePyPTzn).

Specific examples of the above-described heteroaromatic compound having a fused ring structure including the above six-membered ring structure in a part (a heteroaromatic compound having a fused ring structure) include a heteroaromatic compound having a quinoxaline ring, such as bathophenanthroline (abbreviation: BPhen), bathocuproine (abbreviation: BCP), 2,9-di(naphthalen-2-yl)-4,7-diphenyl-1,10-phenanthroline (abbreviation: NBPhen), 2,2'-(1,3-phenylene)bis[9-phenyl-1,10-phenanthroline] (abbreviation: mPPhen2P), 2,2'-(pyridin-2,6-diyl)bis(4-phenylbenzo[h]quinazoline) (abbreviation: 2,6(P-Bqn)$_2$Py), 2-[3-(dibenzothiophen-4-yl)phenyl]dibenzo[f,h]quinoxaline (abbreviation: 2mDBTPDBq-II), 2-[3'-(dibenzothiophen-4-yl)biphenyl-3-yl]dibenzo[f,h]quinoxaline (abbreviation: 2mDBTBPDBq-II), 2-[3'-(9H-carbazol-9-yl)biphenyl-3-yl]dibenzo[f,h]quinoxaline (abbreviation: 2mCzBPDBq), 2-[4-(3,6-diphenyl-9H-carbazol-9-yl)phenyl]dibenzo[f,h]quinoxaline (abbreviation: 2CzPDBq-III), 7-[3-(dibenzothiophen-4-yl)phenyl]dibenzo[f,h]quinoxaline (abbreviation: 7mDBTPDBq-II), 6-[3-(dibenzothiophen-4-yl)phenyl]dibenzo[f,h]quinoxaline (abbreviation: 6mDBTPDBq-II), or 2mpPCBPDBq.

For the electron-transport layers (114, 114*a*, and 114*b*), any of the metal complexes given below can be used as well as the heteroaromatic compounds described above. Examples of the metal complexes include a metal complex having a quinoline ring or a benzoquinoline ring, such as tris(8-quinolinolato)aluminum(III) (abbreviation: $Alq_3$), $Almq_3$, 8-quinolinolatolithium(I) (abbreviation: Liq), $BeBq_2$, bis(2-methyl-8-quinolinolato)(4-phenylphenolato)aluminum(III) (abbreviation: BAlq), or bis(8-quinolinolato)zinc(II) (abbreviation: Znq), and a metal complex having an oxazole ring or a thiazole ring, such as bis[2-(2-benzoxazolyl)phenolato]zinc(II) (abbreviation: ZnPBO), or bis[2-(2-benzothiazolyl)phenolato]zinc(II) (abbreviation: ZnBTZ).

High-molecular compounds such as poly(2,5-pyridinediyl) (abbreviation: PPy), poly[(9,9-dihexylfluorene-2,7-diyl)-co-(pyridine-3,5-diyl)] (abbreviation: PF-Py), and poly[(9,9-dioctylfluorene-2,7-diyl)-co-(2,2'-bipyridine-6,6'-diyl)] (abbreviation: PF-BPy) can be used as the electron-transport material.

Each of the electron-transport layers (114, 114*a*, and 114*b*) is not limited to a single layer and may be a stack of two or more layers each containing any of the above substances.

<Electron-Injection Layer>

The electron-injection layers (115, 115*a*, and 115*b*) contain a substance having a high electron-injection property. The electron-injection layers (115, 115*a*, and 115*b*) are layers for increasing the efficiency of electron injection from the second electrode 102 and are preferably formed using a material whose value of the LUMO level has a small difference (0.5 eV or less) from the work function of a material used for the second electrode 102. Thus, the electron-injection layers (115, 115*a*, and 115*b*) can be formed using an alkali metal, an alkaline earth metal, or a compound thereof, such as lithium, cesium, lithium fluoride (LiF), cesium fluoride (CsF), calcium fluoride ($CaF_2$), 8-quinolinolato-lithium (abbreviation: Liq), 2-(2-pyridyl)phenolato-lithium (abbreviation: LiPP), 2-(2-pyridyl)-3-pyridinolato-lithium (abbreviation: LiPPy), 4-phenyl-2-(2-pyridyl)phenolatolithium (abbreviation: LiPPP), an oxide of lithium ($LiO_x$), or cesium carbonate. A rare earth metal such as ytterbium (Yb) and a compound of a rare earth metal such as erbium fluoride ($ErF_3$) can also be used. For the electron-injection layers (115, 115*a*, and 115*b*), a plurality of kinds of materials given above may be mixed or stacked as films. Electride may also be used for the electron-injection layers (115, 115*a*, and 115*b*). Examples of the electride include a substance in which electrons are added at high concentration to calcium oxide-aluminum oxide. Any of the substances used for the electron-transport layers (114, 114*a*, and 114*b*), which are given above, can also be used.

A mixed material in which an organic compound and an electron donor (donor) are mixed may also be used for the electron-injection layers (115, 115*a*, and 115*b*). Such a mixed material is excellent in an electron-injection property and an electron-transport property because electrons are generated in the organic compound by the electron donor. The organic compound here is preferably a material excellent in transporting the generated electrons; specifically, for example, the above-described electron-transport materials used for the electron-transport layers (114, 114*a*, and 114*b*), such as a metal complex and a heteroaromatic compound, can be used. As the electron donor, a substance showing an electron-donating property with respect to an organic compound is preferably used. Specifically, an alkali metal, an alkaline earth metal, and a rare earth metal are preferable, and lithium, cesium, magnesium, calcium, erbium, ytterbium, and the like are given. In addition, an alkali metal oxide and an alkaline earth metal oxide are preferable, and lithium oxide, calcium oxide, barium oxide, and the like are given. Alternatively, a Lewis base such as magnesium oxide can be used. Further alternatively, an organic compound such as tetrathiafulvalene (abbreviation: TTF) can be used. Alternatively, a stack of two or more of these materials may be used.

A mixed material in which an organic compound and a metal are mixed may also be used for the electron-injection layers (115, 115*a*, and 115*b*). The organic compound used here preferably has a lowest unoccupied molecular orbital (LUMO) level higher than or equal to −3.6 eV and lower than or equal to −2.3 eV. Moreover, a material having an unshared electron pair is preferable.

Thus, as the organic compound used in the above mixed material, a mixed material obtained by mixing a metal and the heteroaromatic compound given above as the material that can be used for the electron-transport layer may be used. Preferred examples of the heteroaromatic compound include materials having an unshared electron pair, such as a heteroaromatic compound having a five-membered ring structure (e.g., an imidazole ring, a triazole ring, an oxazole ring, an oxadiazole ring, a thiazole ring, or a benzimidazole ring), a heteroaromatic compound having a six-membered ring structure (e.g., a pyridine ring, a diazine ring (including a pyrimidine ring, a pyrazine ring, a pyridazine ring, or the like), a triazine ring, a bipyridine ring, or a terpyridine ring), and a heteroaromatic compound having a fused ring structure including a six-membered ring structure as a part (e.g., a quinoline ring, a benzoquinoline ring, a quinoxaline ring, a dibenzoquinoxaline ring, or a phenanthroline ring). Since the materials are specifically described above, description thereof is omitted here.

As a metal used for the above mixed material, a transition metal that belongs to Group 5, Group 7, Group 9, or Group 11 or a material that belongs to Group 13 in the periodic table is preferably used, and examples include Ag, Cu, Al, and In. Here, the organic compound forms a singly occupied molecular orbital (SOMO) with the transition metal.

To amplify light obtained from the light-emitting layer 113*b*, for example, the optical path length between the second electrode 102 and the light-emitting layer 113*b* is preferably less than one fourth of the wavelength λ of light emitted from the light-emitting layer 113*b*. In that case, the optical path length can be adjusted by changing the thickness of the electron-transport layer 114*b* or the electron-injection layer 115*b*.

When the charge-generation layer 106 is provided between the two EL layers (103*a* and 103*b*) as in the light-emitting device in FIG. 2D, a structure in which a plurality of EL layers are stacked between the pair of electrodes (the structure is also referred to as a tandem structure) can be obtained.

<Charge-Generation Layer>

The charge-generation layer 106 has a function of injecting electrons into the EL layer 103*a* and injecting holes into the EL layer 103*b* when voltage is applied between the first electrode (anode) 101 and the second electrode (cathode) 102. The charge-generation layer 106 may have either a structure in which an electron acceptor (acceptor) is added to a hole-transport material or a structure in which an electron donor (donor) is added to an electron-transport material. Alternatively, both of these layers may be stacked. Note that forming the charge-generation layer 106 with the use of any of the above materials can inhibit an increase in driving voltage caused by the stack of the EL layers.

In the case where the charge-generation layer 106 has a structure in which an electron acceptor is added to a hole-transport material, which is an organic compound, any of the materials described in this embodiment can be used as the hole-transport material. Examples of the electron acceptor include 7,7,8,8-tetracyano-2,3,5,6-tetrafluoroquinodimethane (abbreviation: $F_4$-TCNQ) and chloranil. Other examples include oxides of metals that belong to Group 4 to Group 8 of the periodic table. Specific examples include vanadium oxide, niobium oxide, tantalum oxide, chromium oxide, molybdenum oxide, tungsten oxide, manganese oxide, and rhenium oxide.

In the case where the charge-generation layer 106 is an electron-injection buffer layer in which an electron donor is added to an electron-transport material, any of the materials described in this embodiment can be used as the electron-transport material. As the electron donor, it is possible to use an alkali metal, an alkaline earth metal, a rare earth metal, a metal belonging to Group 2 or Group 13 of the periodic table, or an oxide or a carbonate thereof. Specifically, lithium (Li), cesium (Cs), magnesium (Mg), calcium (Ca), ytterbium (Yb), indium (In), lithium oxide, cesium carbonate, or the like is preferably used. An organic compound such as tetrathianaphthacene may be used as the electron donor.

Although FIG. 2D illustrates the structure in which two EL layers 103 are stacked, three or more EL layers may be stacked with charge-generation layers each provided between two adjacent EL layers.

<Substrate>

The light-emitting device described in this embodiment can be formed over a variety of substrates. Note that the type of substrate is not limited to a certain type. Examples of the substrate include semiconductor substrates (e.g., a single crystal substrate and a silicon substrate), an SOI substrate, a glass substrate, a quartz substrate, a plastic substrate, a metal substrate, a stainless steel substrate, a substrate including stainless steel foil, a tungsten substrate, a substrate including tungsten foil, a flexible substrate, an attachment film, paper including a fibrous material, and a base material film.

Examples of the glass substrate include a barium borosilicate glass substrate, an aluminoborosilicate glass substrate, and a soda lime glass substrate. Examples of the flexible substrate, the attachment film, and the base material film include plastics typified by polyethylene terephthalate (PET), polyethylene naphthalate (PEN), and polyether sulfone (PES), a synthetic resin such as acrylic resin, polypropylene, polyester, polyvinyl fluoride, polyvinyl chloride, polyamide, polyimide, aramid, epoxy resin, an inorganic vapor deposition film, and paper.

For fabrication of the light-emitting device in this embodiment, a gas phase method such as an evaporation method or a liquid phase method such as a spin coating method or an ink-jet method can be used. When an evaporation method is used, a physical vapor deposition method (PVD method) such as a sputtering method, an ion plating method, an ion beam evaporation method, a molecular beam evaporation method, or a vacuum evaporation method, a chemical vapor deposition method (CVD method), or the like can be used. Specifically, the layers having various functions (the hole-injection layer 111, the hole-transport layer 112, the light-emitting layer 113, the electron-transport layer 114, and the electron-injection layer 115) included in the EL layers of the light-emitting device can be formed by an evaporation method (e.g., a vacuum evaporation method), a coating method (e.g., a dip coating method, a die coating method, a bar coating method, a spin coating method, or a spray coating method), a printing method (e.g., an ink-jet method, screen printing (stencil), offset printing (planography), flexography (relief printing), gravure printing, or micro-contact printing), or the like.

In the case where a film formation method such as the coating method or the printing method is employed, a high-molecular compound (e.g., an oligomer, a dendrimer, or a polymer), a middle-molecular compound (a compound between a low-molecular compound and a high-molecular compound with a molecular weight of 400 to 4000), an inorganic compound (e.g., a quantum dot material), or the like can be used. The quantum dot material can be a colloidal quantum dot material, an alloyed quantum dot material, a core-shell quantum dot material, a core quantum dot material, or the like.

Materials that can be used for the layers (the hole-injection layer 111, the hole-transport layer 112, the light-emitting layer 113, the electron-transport layer 114, and the electron-injection layer 115) included in the EL layer 103 of the light-emitting device described in this embodiment are not limited to the materials described in this embodiment, and other materials can be used in combination as long as the functions of the layers are fulfilled.

Note that in this specification and the like, the terms "layer" and "film" can be interchanged with each other as appropriate.

The structures described in this embodiment can be used in combination with any of the structures described in the other embodiments as appropriate.

Embodiment 3

In this embodiment, specific structure examples and manufacturing methods of a light-emitting apparatus (also referred to as a display panel) of one embodiment of the present invention will be described.

Structure Example 1 of Light-Emitting Apparatus 700

Figure 3A:
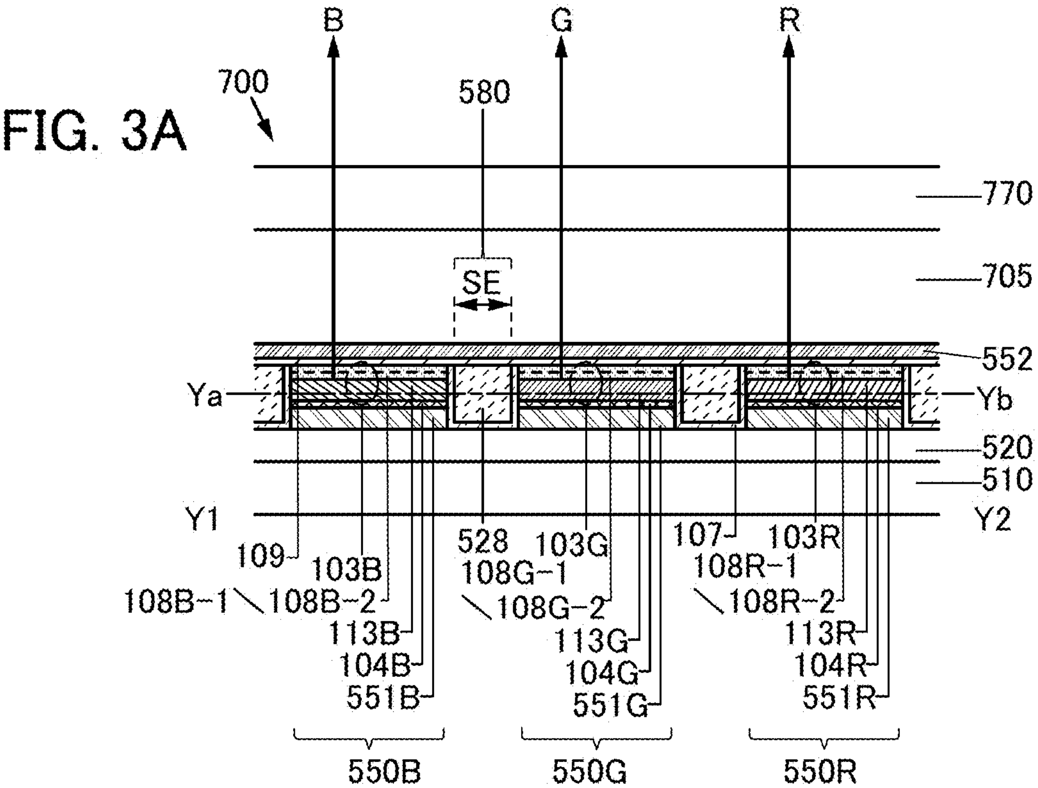
FIGS. 3A to 3D illustrate a light-emitting apparatus of an embodiment.

A light-emitting apparatus 700 illustrated in FIG. 3A includes a light-emitting device 550B, a light-emitting device 550G, a light-emitting device 550R, and a partition 528. The light-emitting device 550B, the light-emitting device 550G, the light-emitting device 550R, and the partition 528 are formed over a functional layer 520 provided over a first substrate 510. The functional layer 520 includes, for example, a driver circuit GD, a driver circuit SD, and the like that are composed of a plurality of transistors, and wirings for electrical connections between components. Note that these driver circuits are electrically connected to the light-emitting device 550B, the light-emitting device 550G, and the light-emitting device 550R, for example, to drive them. The light-emitting apparatus 700 includes an insulating layer 705 over the functional layer 520 and the light-emitting devices, and the insulating layer 705 has a function of attaching a second substrate 770 and the functional layer 520.

The light-emitting device 550B, the light-emitting device 550G, and the light-emitting device 550R each have any of the device structures described in Embodiments 1 and 2. Specifically, the case is described in which the EL layer 103 in the structure illustrated in FIG. 2A differs between the light-emitting devices.

In this specification and the like, a structure in which light-emitting layers in light-emitting devices of different colors (for example, blue (B), green (G), and red (R)) are separately formed or separately patterned may be referred to as a side-by-side (SBS) structure. Note that in the light-emitting apparatus 700 illustrated in FIG. 3A, the light-emitting device 550B, the light-emitting device 550G, and the light-emitting device 550R are arranged in this order; however, one embodiment of the present invention is not limited thereto. For example, in the light-emitting apparatus 700, the light-emitting device 550R, the light-emitting device 550G, and the light-emitting device 550B may be arranged in this order.

As illustrated in FIG. 3A, the light-emitting device 550B includes an electrode 551B, the electrode 552, and the EL layer 103B. Note that a specific structure of each layer is as described in Embodiment 1 and Embodiment 2. The EL layer 103B has a stacked-layer structure of layers having different functions including a light-emitting layer. Although in FIG. 3A, only a hole-injection/transport layer 104B, an electron-transport layer (108B-1108B-2) having a structure in which a first electron-transport layer (108B-1) and a second electron-transport layer (108B-2) are stacked, and the electron-injection layer 109 are illustrated as layers of the EL layer 103B including the light-emitting layer, the present invention is not limited to the illustration. Note that the hole-injection/transport layer 104B represents the layer having the functions of the hole-injection layer and the hole-transport layer described in Embodiment 2 and may have a stacked-layer structure. Note that in this specification, a hole-injection/transport layer in any light-emitting device can be interpreted in the above manner.

Note that the electron-transport layer (108B-1108B-2) has the structure described in Embodiment 1. The electron-transport layer (108B-1108B-2) can have a function of blocking holes moving from the anode side to the cathode side through the light-emitting layer. The electron-injection layer 109 may have a stacked-layer structure in which some or all of layers are formed using different materials.

As illustrated in FIG. 3A, an insulating layer 107 may be formed on side surfaces (or end portions) of the hole-injection/transport layer 104B, the light-emitting layer, and the electron-transport layer (108B-1108B-2), which are included in the EL layer 103B including the light-emitting layer. The insulating layer 107 is formed in contact with side surfaces (or end portions) of the EL layer 103B. Accordingly, entry of oxygen, moisture, and a substance containing constituent elements of oxygen or moisture through the side surface of the EL layer 103B into the inside of the EL layer 103B can be inhibited. For the insulating layer 107, aluminum oxide, magnesium oxide, hafnium oxide, gallium oxide, indium gallium zinc oxide, silicon nitride, or silicon nitride oxide can be used, for example. Some of the above-described materials may be stacked to form the insulating layer 107. The insulating layer 107 can be formed by a sputtering method, a CVD method, an MBE method, a PLD method, an ALD method, or the like and is formed preferably by an ALD method, which achieves favorable coverage.

The electron-injection layer 109 is formed to cover some layers in the EL layer 103B (the light-emitting layer 113B, the hole-injection/transport layer 104B, and the electron-transport layer (108B-1108B-2)) and the insulating layer 107. The electron-injection layer 109 may have a stacked-layer structure of two or more layers having different electric resistances.

The electrode 552 is formed over the electron-injection layer 109. Note that the electrode 551B and the electrode 552 have an overlap region. The EL layer 103B is positioned between the electrode 551B and the electrode 552.

The EL layer 103B illustrated in FIG. 3A has a structure similar to that of the EL layer 103 described in Embodiment 2. The EL layer 103B is capable of emitting blue light, for example.

As illustrated in FIG. 3A, the light-emitting device 550G includes an electrode 551G, the electrode 552, and an EL layer 103G. Note that a specific structure of each layer is as described in Embodiments 1 and 2. The EL layer 103G has a stacked-layer structure of layers having different functions including a light-emitting layer. Although in FIG. 3A, only a hole-injection/transport layer 104G, an electron-transport layer (108G-1108G-2) having a structure in which a first electron-transport layer (108G-1) and a second electron-transport layer (108G-2) are stacked, and the electron-injection layer 109 are illustrated as layers of the EL layer 103G including the light-emitting layer, the present invention is not limited to the illustration. Note that the hole-injection/transport layer 104G represents the layer having the functions of the hole-injection layer and the hole-transport layer described in Embodiment 2 and may have a stacked-layer structure.

Note that the electron-transport layer (108B-1108B-2) has the structure described in Embodiment 1. The electron-transport layer (108B-1108B-2) can have a function of blocking holes moving from the anode side to the cathode side through the light-emitting layer. The electron-injection layer 109 may have a stacked-layer structure in which some or all of layers are formed using different materials.

As illustrated in FIG. 3A, the insulating layer 107 may be formed on side surfaces (or end portions) of the hole-injection/transport layer 104G, the light-emitting layer, and the electron-transport layer (108G-1108G-2), which are included in the EL layer 103G including the light-emitting layer. The insulating layer 107 is formed in contact with side surfaces (or end portions) of the EL layer 103G. Accordingly, entry of oxygen, moisture, and constituent elements thereof through the side surface of the EL layer 103G into the inside of the EL layer 103G can be inhibited. For the insulating layer 107, aluminum oxide, magnesium oxide, hafnium oxide, gallium oxide, indium gallium zinc oxide, silicon nitride, or silicon nitride oxide can be used, for example. Some of the above-described materials may be stacked to form the insulating layer 107. The insulating layer 107 can be formed by a sputtering method, a CVD method, an MBE method, a PLD method, an ALD method, or the like and is formed preferably by an ALD method, which achieves favorable coverage.

The electron-injection layer 109 is formed to cover some layers in the EL layer 103G (the light-emitting layer 113G, the hole-injection/transport layer 104G, and the electron-transport layer (108G-1108G-2)) and the insulating layer 107. The electron-injection layer 109 may have a stacked-layer structure of two or more layers having different electric resistances.

The electrode 552 is formed over the electron-injection layer 109. Note that the electrode 551G and the electrode 552 have an overlap region. The EL layer 103G is positioned between the electrode 551G and the electrode 552.

The EL layer 103G illustrated in FIG. 3A has a structure similar to that of the EL layer 103 described in Embodiment 2. The EL layer 103G is capable of emitting green light, for example.

As illustrated in FIG. 3A, the light-emitting device 550R includes an electrode 551R, the electrode 552, and an EL layer 103R. Note that a specific structure of each layer is as described in Embodiments 1 and 2. The EL layer 103R has a stacked-layer structure of layers having different functions including the light-emitting layer 113R. Although in FIG. 3A, only a hole-injection/transport layer 104R, an electron-transport layer (108R-1108R-2) having a structure in which a first electron-transport layer (108R-1) and a second electron-transport layer (108R-2) are stacked, and the electron-injection layer 109 are illustrated as layers of the EL layer 103R including the light-emitting layer, the present invention is not limited to the illustration. Note that the hole-injection/transport layer 104R represents the layer having the functions of the hole-injection layer and the hole-transport layer described in Embodiment 2 and may have a stacked-layer structure.

Note that the electron-transport layer (108R-1108R-2) has the structure described in Embodiment 1. The electron-transport layer (108R-1108R-2) can have a function of blocking holes moving from the anode side to the cathode side through the light-emitting layer. The electron-injection layer 109 may have a stacked-layer structure in which some or all of layers are formed using different materials.

As illustrated in FIG. 3A, an insulating layer 107 may be formed on side surfaces (or end portions) of the hole-injection/transport layer 104R, the light-emitting layer, and the electron-transport layer (108R-1108R-2), which are included in the EL layer 103R including the light-emitting layer. The insulating layer 107 is formed in contact with side surfaces (or end portions) of the EL layer 103R. Accordingly, entry of oxygen, moisture, and constituent elements of oxygen or moisture through the side surface of the EL layer 103R into the inside of the EL layer 103R can be inhibited. For the insulating layer 107, aluminum oxide, magnesium oxide, hafnium oxide, gallium oxide, indium gallium zinc oxide, silicon nitride, or silicon nitride oxide can be used, for example. Some of the above-described materials may be stacked to form the insulating layer 107. The insulating layer 107 can be formed by a sputtering method, a CVD method, an MBE method, a PLD method, an ALD method, or the like and is formed preferably by an ALD method, which achieves favorable coverage.

The electron-injection layer 109 is formed to cover some layers in the EL layer 103R (the light-emitting layer, the hole-injection/transport layer 104R, and the electron-transport layer (108R-1108R-2)) and the insulating layer 107. The electron-injection layer 109 may have a stacked-layer structure of two or more layers having different electric resistances.

The electrode 552 is formed over the electron-injection layer 109. Note that the electrode 551R and the electrode 552 have an overlap region. The EL layer 103R is positioned between the electrode 551R and the electrode 552.

The EL layer 103R illustrated in FIG. 3A has a structure similar to that of the EL layer 103 described in Embodiment 2. The EL layer 103R is capable of emitting red light, for example.

The partition 528 is provided between the EL layer 103B, the EL layer 103G, and the EL layer 103R. As illustrated in FIG. 3A, the side surfaces (or end portions) of each of the EL layers (103B, 103G, and 103R) of the light-emitting devices are in contact with the partition 528 with the insulating layer 107 therebetween.

In each of the EL layers, especially the hole-injection layer, which is included in the hole-transport region placed between the anode and the light-emitting layer, often has high conductivity; thus, a hole-injection layer formed as a layer shared by adjacent light-emitting devices might cause crosstalk. Thus, providing the partition 528 made of an insulating material between the EL layers as shown in this structure example can suppress occurrence of crosstalk between adjacent light-emitting devices.

In the manufacturing method described in this embodiment, a side surface (or an end portion) of the EL layer is exposed in the patterning step. This may promote deterioration of the EL layer by allowing the entry of oxygen, water, and the like through the side surface (or the end portion). Hence, providing the partition 528 can inhibit the deterioration of the EL layer in the fabrication process.

Furthermore, a projecting portion generated between adjacent light-emitting devices can be flattened by provision of the partition 528. When the projecting portion is flattened, disconnection of the electrode 552 formed over the EL layers can be inhibited. Examples of an insulating material used to form the partition 528 include organic materials such as an acrylic resin, a polyimide resin, an epoxy resin, an imide resin, a polyamide resin, a polyimide-amide resin, a silicone resin, a siloxane resin, a benzocyclobutene-based resin, a phenol resin, and precursors of these resins. Other examples include organic materials such as polyvinyl alcohol (PVA), polyvinyl butyral, polyvinyl pyrrolidone, polyethylene glycol, polyglycerin, pullulan, water-soluble cellulose, and alcohol-soluble polyamide resin. A photosensitive resin such as a photoresist can also be used. Examples of the photosensitive resin include positive-type materials and negative-type materials.

With the use of the photosensitive resin, the partition 528 can be fabricated by only light exposure and developing steps. The partition 528 may be fabricated using a negative photosensitive resin (e.g., a resist material). In the case where an insulating layer containing an organic material is used as the partition 528, a material absorbing visible light is suitably used. When a material that absorbs visible light is used as the partition 528, light emitted by the EL layer can be absorbed by the partition 528, whereby light that might leak to an adjacent EL layer (stray light) can be reduced. Accordingly, a display panel with high display quality can be provided.

For example, the difference between the level of the top surface of the partition 528 and the level of the top surface of any of the EL layer 103B, the EL layer 103G, and the EL layer 103R is 0.5 times or less, and further 0.3 times or less the thickness of the partition 528. The partition 528 may be provided such that the level of the top surface of any of the EL layer 103B, the EL layer 103G, and the EL layer 103R is higher than the level of the top surface of the partition 528, for example. The partition 528 may be provided such that the level of the top surface of the partition 528 is higher than the level of the top surface of the light-emitting layer in any of the EL layer 103B, the EL layer 103G, and the EL layer 103R, for example.

When electrical continuity is established between the EL layer 103B, the EL layer 103G, and the EL layer 103R in a light-emitting apparatus (display panel) with a high resolution exceeding 1000 ppi, crosstalk occurs, resulting in a narrower color gamut that the light-emitting apparatus is capable of reproducing. Providing the partition 528 in a high-resolution display panel with more than 1000 ppi, preferably more than 2000 ppi, or further preferably in an ultrahigh-resolution display panel with more than 5000 ppi allows the display panel to express vivid colors.

Figure 3B:
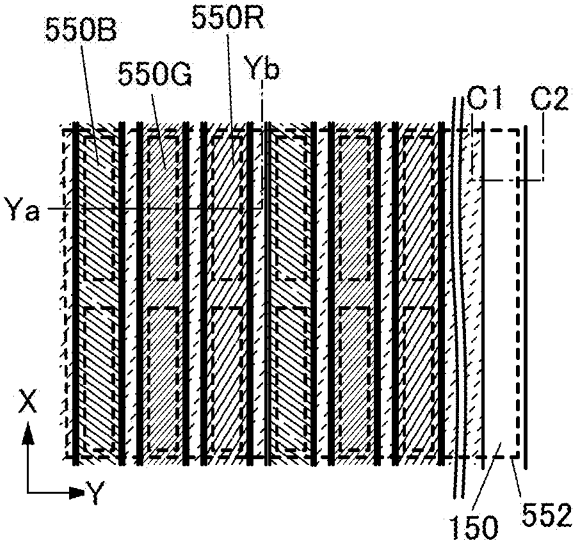
Figure 3C:
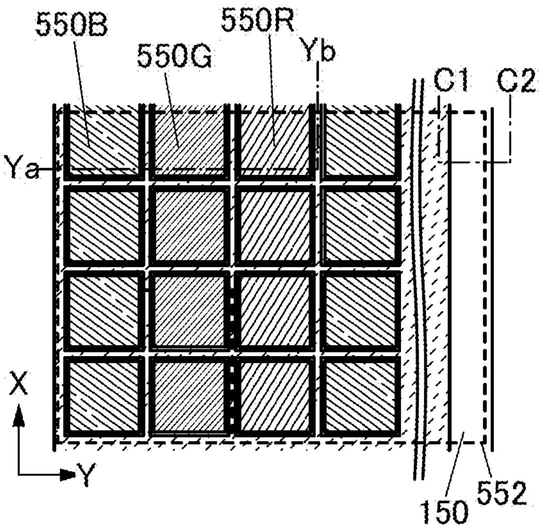

FIGS. 3B and 3C are each a schematic top view of the light-emitting apparatus 700 taken along the dash-dot line Ya-Yb in the cross-sectional view of FIG. 3A. Specifically, the light-emitting devices 550B, the light-emitting devices 550G, and the light-emitting devices 550R are arranged in a matrix. Note that FIG. 3B illustrates what is called a stripe arrangement, in which the light-emitting devices of the same color are arranged in the X-direction. In the Y direction perpendicular to the X direction, light-emitting devices of different colors are arranged. Note that the arrangement method of the light-emitting devices is not limited thereto; another method such as a delta, zigzag, PenTile, or diamond arrangement may also be used.

The EL layers (103B, 103G, and 103R) are processed to be separated by patterning using a photolithography method; hence, a high-resolution light-emitting apparatus (display panel) can be fabricated. End portions (side surfaces) of the EL layer processed by patterning using a photolithography method have substantially one surface (or are positioned on substantially the same plane). In this case, the width (SE) of a space 580 between the EL layers is preferably 5 μm or less, further preferably 1 μm or less.

In the EL layer, especially the hole-injection layer, which is included in the hole-transport region between the anode and the light-emitting layer, often has high conductivity; thus, a hole-injection layer formed as a layer shared by adjacent light-emitting devices might cause crosstalk. Therefore, processing the EL layers to be separated by patterning using a photolithography method as shown in this structure example can suppress occurrence of crosstalk between adjacent light-emitting devices.

Figure 3D:
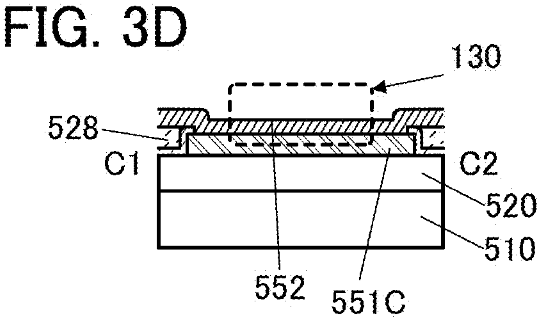

FIG. 3D is a schematic cross-sectional view including a region 150, taken along the dash-dot line C1-C2 in FIGS. 3B and 3C. FIG. 3D illustrates a connection portion 130 where a connection electrode 551C and an electrode 552 are electrically connected to each other. In the connection portion 130, the electrode 552 is provided over and in contact with the connection electrode 551C. The partition 528 is provided so as to cover an end portion of the connection electrode 551C.

Example 1 of Method of Manufacturing Light-Emitting Apparatus

Figure 4A:
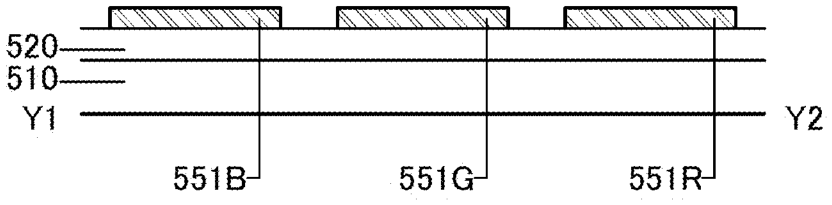
FIGS. 4A to 4C illustrate a fabrication method of a light-emitting apparatus of an embodiment.

The electrode 551B, the electrode 551G, and the electrode 551R are formed as illustrated in FIG. 4A. For example, a conductive film is formed over the functional layer 520 over the first substrate 510 and processed into predetermined shapes by a photolithography method.

The conductive film can be formed by any of a sputtering method, a chemical vapor deposition (CVD) method, a molecular beam epitaxy (MBE) method, a vacuum evaporation method, a pulsed laser deposition (PLD) method, an atomic layer deposition (ALD) method, and the like. Examples of the CVD method include a plasma-enhanced chemical vapor deposition (PECVD) method and a thermal CVD method. An example of a thermal CVD method is a metal organic CVD (MOCVD) method.

The conductive film may be processed into a thin film by a nanoimprinting method, a sandblasting method, a lift-off method, or the like as well as a photolithography method described above. Alternatively, island-shaped thin films may be directly formed by a film formation method using a shielding mask such as a metal mask.

There are two typical examples of photolithography methods. In one of the methods, a resist mask is formed over a thin film that is to be processed, the thin film is processed by etching or the like, and then the resist mask is removed. In the other method, a photosensitive thin film is formed and then processed into a desired shape by light exposure and development. The former method involves heat treatment steps such as pre-applied bake (PAB) after resist application and post-exposure bake (PEB) after light exposure. In one embodiment of the present invention, a lithography method is used not only for processing of a conductive film but also for processing of a thin film used for the formation of an EL layer (a film made of an organic compound or a film partly including an organic compound).

As light for exposure in a photolithography method, it is possible to use light with the i-line (wavelength: 365 nm), light with the g-line (wavelength: 436 nm), light with the h-line (wavelength: 405 nm), or light in which the i-line, the g-line, and the h-line are mixed. Alternatively, ultraviolet light, KrF laser light, ArF laser light, or the like can be used. Exposure may be performed by liquid immersion exposure technique. As the light for exposure, extreme ultraviolet (EUV) light or X-rays may also be used. Instead of the light for exposure, an electron beam can be used. It is preferable to use EUV, X-rays, or an electron beam because extremely minute processing can be performed. Note that a photomask is not needed when exposure is performed by scanning with a beam such as an electron beam.

For etching of a thin film using a resist mask, a dry etching method, a wet etching method, a sandblast method, or the like can be used.

Figure 4B:
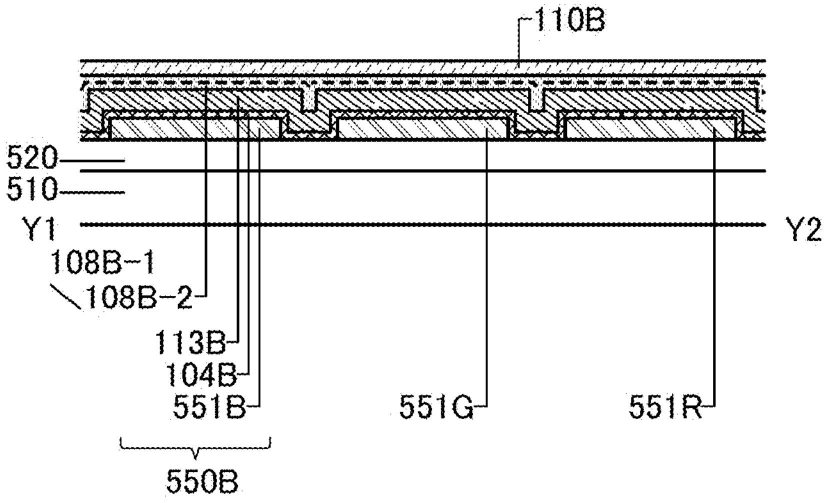

Then, as illustrated in FIG. 4B, the part of the EL layer 103B is formed over the electrodes 551B, 551G, and 551R. In FIG. 4B, as the part of the EL layer 103B, the hole-injection/transport layer 104B, the light-emitting layer 113B, and the electron-transport layer (108B-1108B-2) are formed. The part of the EL layer 103B can be formed over the electrodes 551B, 551G, and 551R to cover these electrodes by a vacuum evaporation method, for example. Furthermore, a sacrificial layer 110B is formed over the electron-transport layer (108B-1108B-2) which are the part of the EL layer 103B.

For the sacrificial layer 110B, a film highly resistant to etching treatment performed on the EL layer 103B, i.e., a film having high etching selectivity with respect to the EL layer 103B, can be used. The sacrificial layer 110B preferably has a stacked-layer structure of a first sacrificial layer and a second sacrificial layer which have different etching selectivities to the EL layer 103B. For the sacrificial layer 110B, it is possible to use a film that can be removed by a wet etching method, which causes less damage to the EL layer 103B. In wet etching, oxalic acid or the like can be used as an etching material.

For the sacrificial layer 110B, an inorganic film such as a metal film, an alloy film, a metal oxide film, a semiconductor film, or an inorganic insulating film can be used, for example. The sacrificial layer 110B can be formed by any of a variety of film formation methods such as a sputtering method, an evaporation method, a CVD method, and an ALD method.

For the sacrificial layer 110B, a metal material such as gold, silver, platinum, magnesium, nickel, tungsten, chromium, molybdenum, iron, cobalt, copper, palladium, titanium, aluminum, yttrium, zirconium, or tantalum or an alloy material containing the metal material can be used, for example. It is preferable to use a low-melting-point material such as aluminum or silver, in particular.

A metal oxide such as indium gallium zinc oxide (also referred to as In—Ga—Zn oxide or IGZO) can be used for the sacrificial layer 110B. It is also possible to use indium oxide, indium zinc oxide (In—Zn oxide), indium tin oxide (In—Sn oxide), indium titanium oxide (In—Ti oxide), indium tin zinc oxide (In—Sn—Zn oxide), indium titanium zinc oxide (In—Ti—Zn oxide), indium gallium tin zinc oxide (In—Ga—Sn—Zn oxide), or the like. Indium tin oxide containing silicon, or the like can also be used.

An element M (M is one or more of aluminum, silicon, boron, yttrium, copper, vanadium, beryllium, titanium, iron, nickel, germanium, zirconium, molybdenum, lanthanum, cerium, neodymium, hafnium, tantalum, tungsten, and magnesium) can be used instead of gallium. In particular, Mis preferably one or more of gallium, aluminum, and yttrium.

For the sacrificial layer 110B, an inorganic insulating material such as aluminum oxide, hafnium oxide, or silicon oxide can be used.

The sacrificial layer 110B is preferably formed using a material that can be at least dissolved in a solvent chemically stable with respect to the uppermost film (electron-transport layer (108B-1108B-2)) which is part of the EL layer 103B. Specifically, a material that will be dissolved in water or alcohol can be suitably used for the sacrificial layer 110B. In formation of the sacrificial layer 110B, it is preferable that a solution in which such a material is dissolved in a solvent such as water or alcohol be applied by a wet process and followed by heat treatment for evaporating the solvent. At this time, the heat treatment is preferably performed under a reduced-pressure atmosphere, in which case the solvent can be removed at a low temperature in a short time and thermal damage to the EL layer 103B can be accordingly minimized.

In the case where the sacrificial layer 110B having a stacked-layer structure is formed, the stacked-layer structure can include the first sacrificial layer formed using any of the above-described materials and the second sacrificial layer thereover.

The second sacrificial layer in that case is a film used as a hard mask for etching of the first sacrificial layer. In processing the second sacrificial layer, the first sacrificial layer is exposed. Thus, a combination of films having greatly different etching rates is selected for the first sacrificial layer and the second sacrificial layer. Thus, a film that can be used for the second sacrificial layer can be selected in accordance with the etching conditions of the first sacrificial layer and those of the second sacrificial layer.

For example, in the case where the second sacrificial layer is etched by dry etching with use of a fluorine-containing gas (also referred to as fluorine-based gas), the second sacrificial layer can be formed using silicon, silicon nitride, silicon oxide, tungsten, titanium, molybdenum, tantalum, tantalum nitride, an alloy containing molybdenum and niobium, an alloy containing molybdenum and tungsten, or the like. Here, a metal oxide film using IGZO, ITO, or the like is given as a film having high etching selectivity (that is, enabling low etching rate) in dry etching using the fluorine-based gas, and such a film can be used as the first sacrificial layer.

Note that the material for the second sacrificial layer is not limited to the above and can be selected from a variety of materials in view of the etching conditions of the first sacrificial layer and those of the second sacrificial layer. For example, any of the films that can be used for the first sacrificial layer can be used for the second sacrificial layer.

For the second sacrificial layer, for example, a nitride film can be used. Specifically, it is possible to use a nitride such as silicon nitride, aluminum nitride, hafnium nitride, titanium nitride, tantalum nitride, tungsten nitride, gallium nitride, or germanium nitride.

Alternatively, an oxide film can be used for the second sacrificial layer. Typically, it is possible to use a film of an oxide or an oxynitride such as silicon oxide, silicon oxynitride, aluminum oxide, aluminum oxynitride, hafnium oxide, or hafnium oxynitride.

Figure 4C:
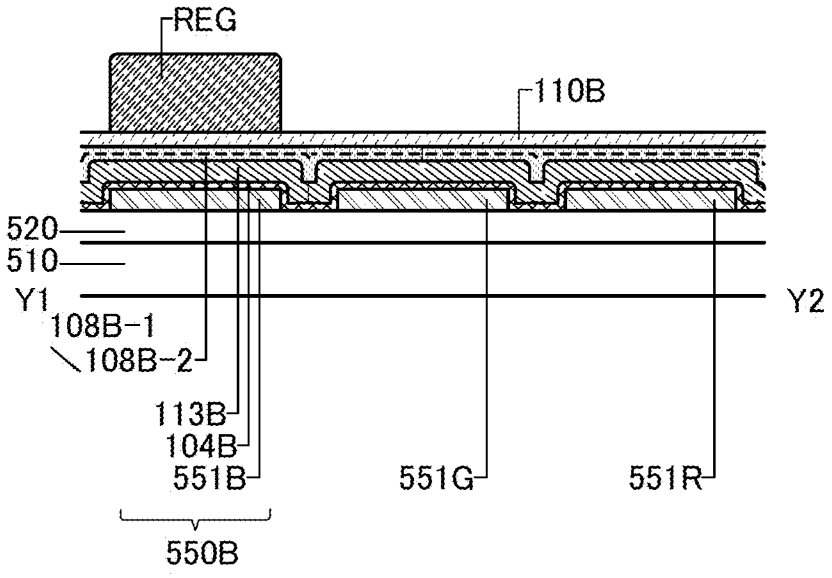

Next, as illustrated in FIG. 4C, a resist is applied onto the sacrificial layer 110B, and the resist having a desired shape (a resist mask REG) is formed by a photolithography method. Such a method involves heat treatment steps such as pre-applied bake (PAB) after the resist application and post-exposure bake (PEB) after light exposure. The temperature reaches approximately 100° C. during the PAB, and approximately 120° C. during the PEB, for example. Therefore, the light-emitting device should be resistant to such high treatment temperatures.

Figure 5A:
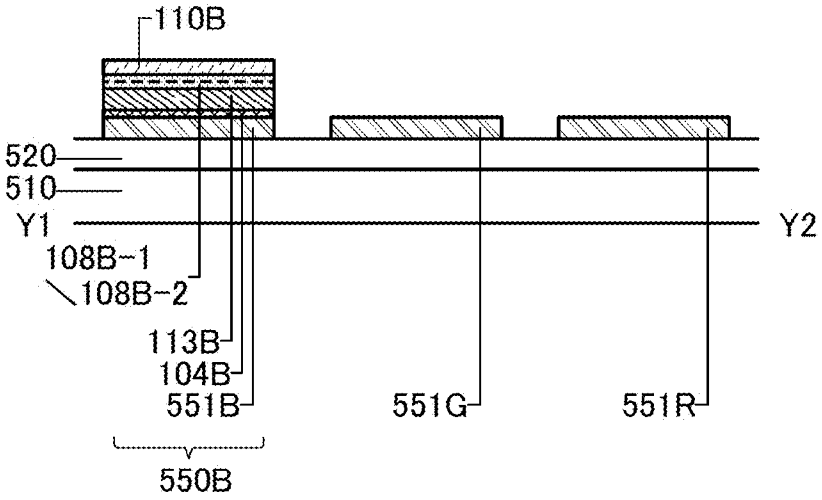
FIGS. 5A to 5C illustrate the fabrication method of a light-emitting apparatus of an embodiment.

Next, with the use of the obtained resist mask REG, part of the sacrificial layer 110B not covered with the resist mask REG is removed by etching; the resist mask REG is removed; and part of the EL layer 103B not covered with the sacrificial layer 110B is then removed by etching, i.e., the EL layer 103B over the electrode 551G and the EL layer 103B over the electrode 551R are removed by etching, so that the EL layer 103B is processed to have side surfaces (or have their side surfaces exposed) or have a belt-like shape that extends in the direction perpendicular to the plane of the paper sheet. Specifically, dry etching is performed using the sacrificial layer 110B formed in a pattern over the EL layer 103B overlapping the electrode 551B. Note that in the case where the sacrificial layer 110B has the aforementioned stacked-layer structure of the first sacrificial layer and the second sacrificial layer, the EL layer 103B may be processed into a predetermined shape in the following manner: part of the second sacrificial layer is etched with the use of the resist mask REG, the resist mask REG is then removed, and part of the first sacrificial layer is etched with the use of the second sacrificial layer as a mask. The structure illustrated in FIG. 5A is obtained through these etching steps.

Figure 5B:
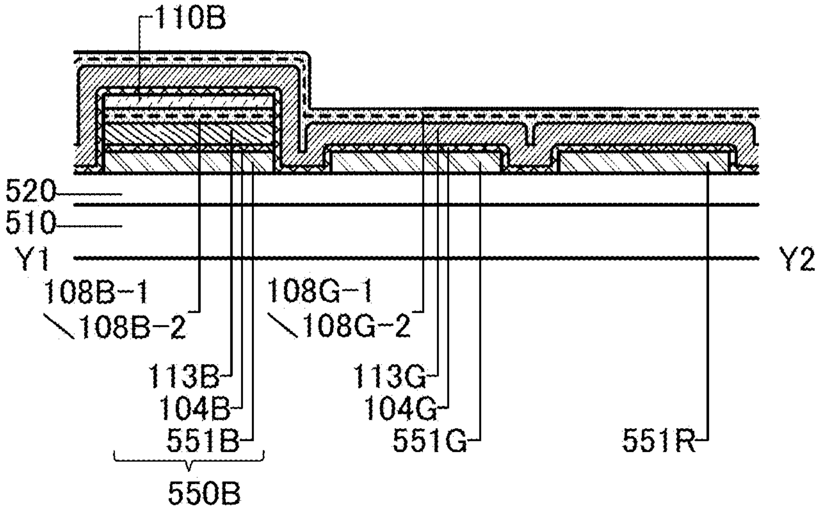

Then, as illustrated in FIG. 5B, the part of the EL layer 103G is formed over the sacrificial layer 110B and the electrodes 551G, and 551R. In FIG. 5B, as the EL layer 103G, the hole-injection/transport layer 104G, the light-emitting layer 113G, and the electron-transport layer (108G-1\108G-2) are formed. The EL layer 103G can be formed over the sacrificial layer 110B and the electrodes 551G and 551R to cover these electrodes by a vacuum evaporation method, for example.

Figure 5C:
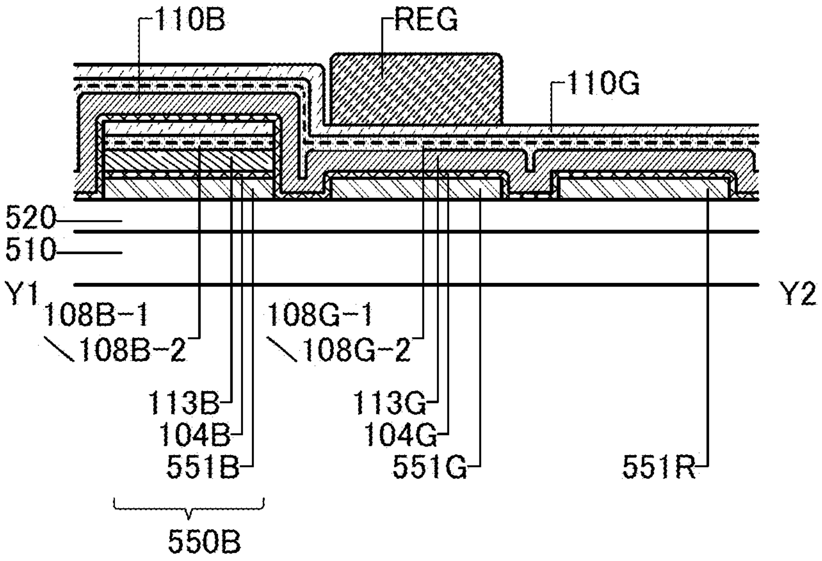
Figure 6A:
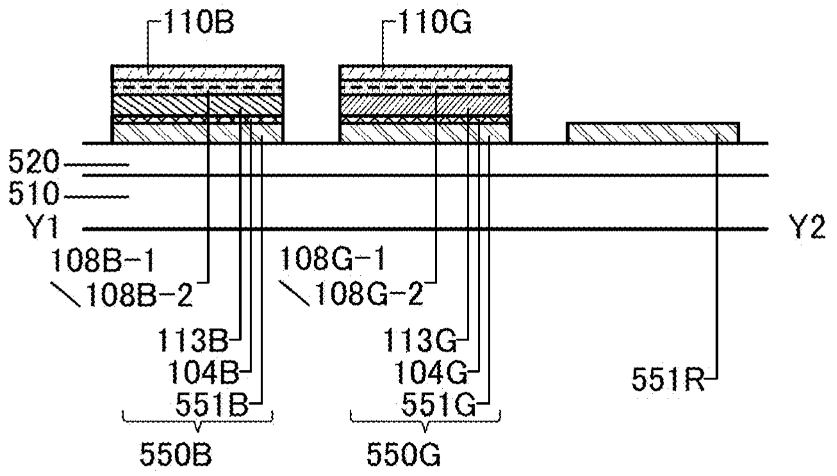
FIGS. 6A to 6C illustrate the fabrication method of a light-emitting apparatus of an embodiment.

Then, as illustrated in FIG. 5C, a sacrificial layer 110G is formed over the electron-transport layer (108G-1\108G-2) which is part of the EL layer 103G, a resist is applied onto the sacrificial layer 110G, and the resist having a desired shape (resist mask REG) is formed by a photolithography method. Part of the sacrificial layer not covered with the obtained resist mask is removed by etching, the resist mask is removed, and part of the EL layer 103G not covered with the sacrificial layer 110G is then removed by etching. Thus, part of the EL layer 103G over the electrode 551B and part of the EL layer 103G over the electrode 551R are removed by etching, so that the EL layer 103G is processed to have side surfaces (or have their side surfaces exposed) or have a belt-like shape that extends in the direction intersecting the sheet of the diagram as illustrated in FIG. 6A. Note that in the case where the sacrificial layer 110G has the aforementioned stacked-layer structure of the first sacrificial layer and the second sacrificial layer, part of the EL layer 103G may be processed into a predetermined shape in the following manner: part of the second sacrificial layer is etched with the use of the resist mask, the resist mask is then removed, and part of the first sacrificial layer is etched with the use of the second sacrificial layer as a mask.

Figure 6B:
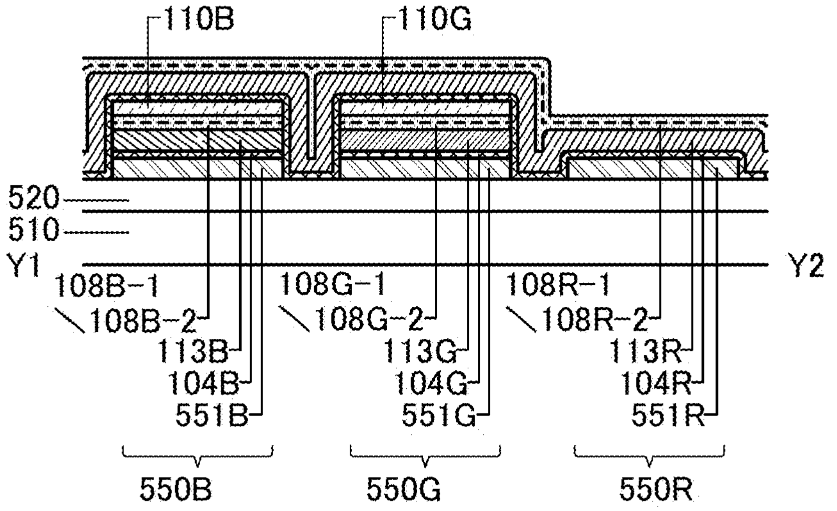

Then, as illustrated in FIG. 6B, the part of the EL layer 103R is formed over the sacrificial layers 110B and 110G and the electrode 551R. In FIG. 6B, as the part of the EL layer 103R, the hole-injection/transport layer 104R, the light-emitting layer, and the electron-transport layer (108R-1\108R-2) are formed. The part of the EL layer 103R can be formed over the sacrificial layers 110B and 110G and the electrode 551R to cover the electrode by a vacuum evaporation method, for example.

Figure 6C:
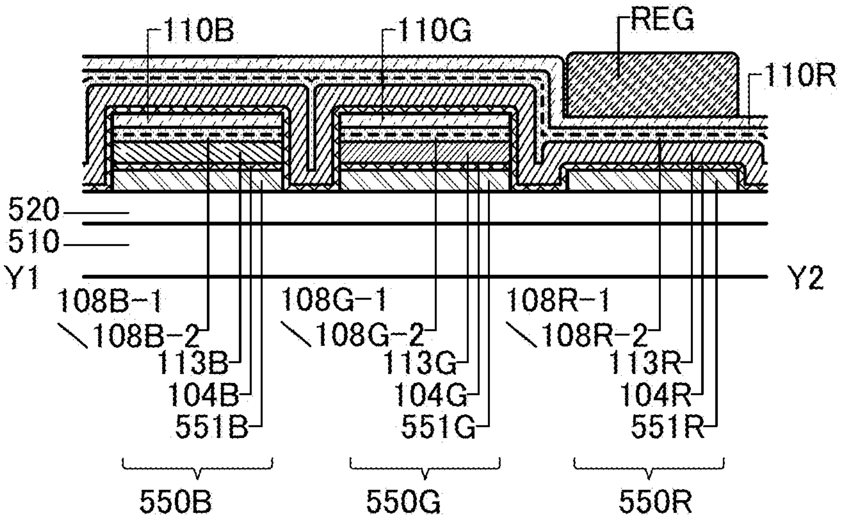
Figure 7A:
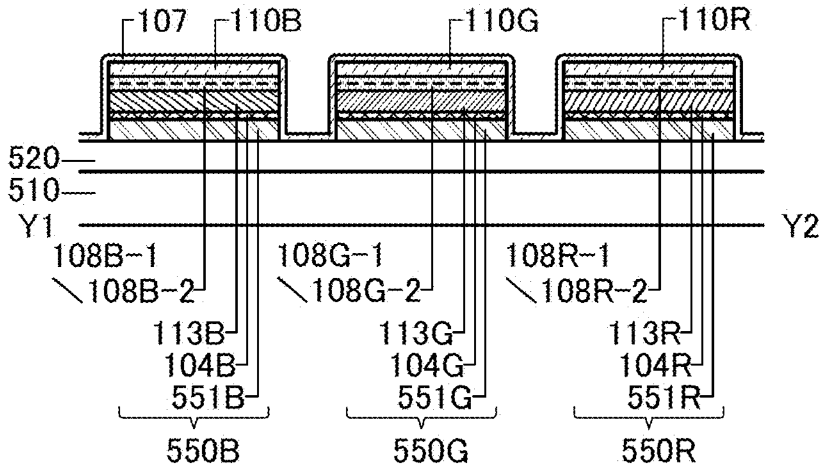
FIGS. 7A to 7C illustrate the fabrication method of a light-emitting apparatus of an embodiment.

Then, as illustrated in FIG. 6C, a sacrificial layer 110R is formed over the electron-transport layer (108R-1\108R-2) which is part of the EL layer 103R, a resist is applied onto the sacrificial layer 110R, and the resist having a desired shape (resist mask REG) is formed by a photolithography method. Part of the sacrificial layer not covered with the obtained resist mask is removed by etching, the resist mask is removed, and part of the EL layer 103R not covered with the sacrificial layer 110R is then removed by etching. Thus, part of the EL layer 103R over the electrode 551B and part of the EL layer 103R over the electrode 551G are removed by etching, so that the EL layer 103R is processed to have side surfaces (or have their side surfaces exposed) or have a belt-like shape that extends in the direction intersecting the sheet of the diagram. Note that in the case where the sacrificial layer 110G has the aforementioned stacked-layer structure of the first sacrificial layer and the second sacrificial layer, the EL layer 103G may be processed into a predetermined shape in the following manner: part of the second sacrificial layer is etched with the use of the resist mask, the resist mask is then removed, and part of the first sacrificial layer is etched with the use of the second sacrificial layer as a mask. Then, the insulating layer 107 is formed over the sacrificial layers (110B, 110G, and 110R) with the sacrificial layers (110B, 110G, and 110R) remaining over the EL layers (103B, 103G, and 103R), so that the structure illustrated in FIG. 7A is obtained.

Note that the insulating layer 107 can be formed by an ALD method, for example. In this case, the insulating layer 107 is formed in contact with the side surfaces of the EL layers (103B, 103G, and 103R) as illustrated in FIG. 7A. This can inhibit entry of oxygen, moisture, and constituent elements thereof into the inside through the side surfaces of the EL layers (103B, 103G, and 103R). Examples of the material used for the insulating layer 107 include aluminum oxide, magnesium oxide, hafnium oxide, gallium oxide, indium gallium zinc oxide, silicon nitride, and silicon nitride oxide.

Figure 7B:
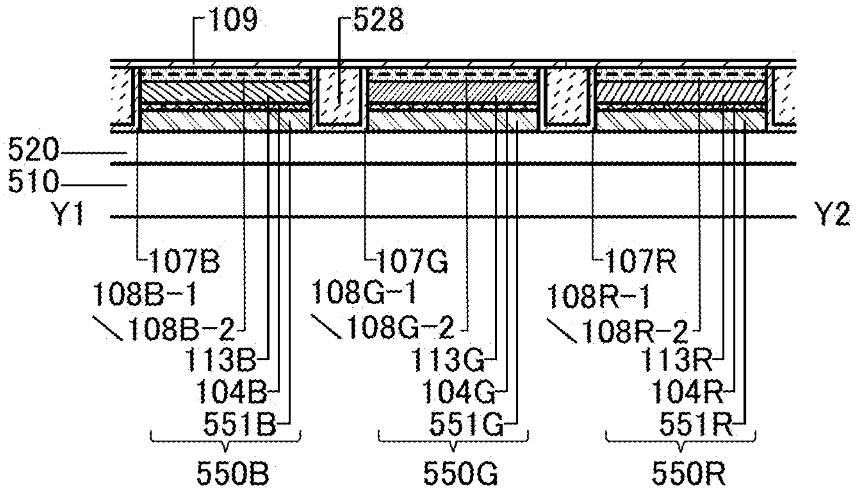

Then, as illustrated in FIG. 7B, after the sacrificial layers (110B, 110G, and 110R) are removed, the partition 528 is formed over the insulating layers (107B, 107G, and 107R), and the electron-injection layer 109 is formed over the partition 528 and the electron-transport layers (108B-1\108B-2, 108G-1\108G-2, and 108R-1\108R-2). The electron-injection layer 109 is formed by a vacuum evaporation method, for example. Note that the electron-injection layer 109 is formed over the electron-transport layers (108B-1\108B-2, 108G-1\108G-2, and 108R-1\108R-2). The electron-injection layer 109 is in contact with the side surfaces (end portions) of the hole-injection/transport layer (104R, 104G, and 104B), the light-emitting layers (103B, 103G, and 103R), and the electron-transport layers (108B-1\108B-2, 108G-1\108G-2, and 108R-1\108R-2), which are part of the EL layers (103B, 103G, and 103R), with the insulating layers (107B, 107G, and 107R) therebetween.

Figure 7C:
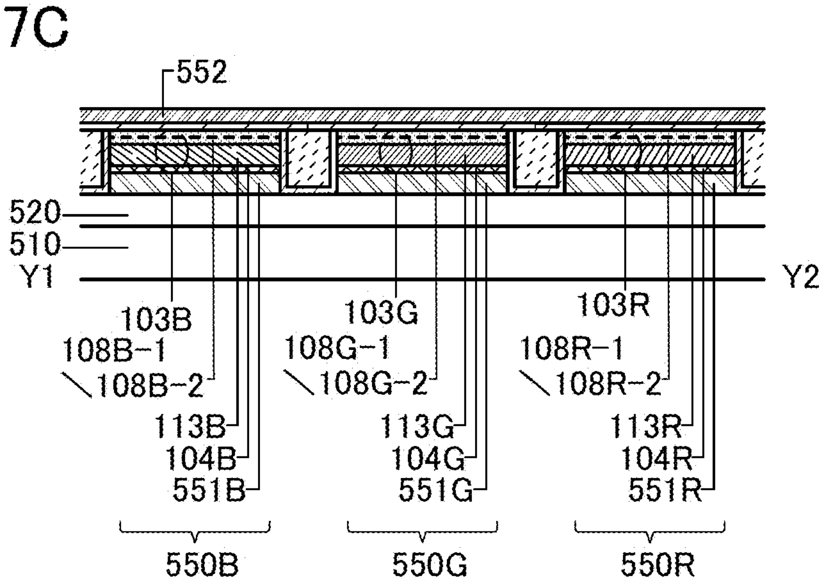

Next, as illustrated in FIG. 7C, the electrode 552 is formed. The electrode 552 is formed by a vacuum evaporation method, for example. The electrode 552 is formed over the electron-injection layer 109. The electrode 552 is in contact with the side surfaces (or end portions) of the EL layers (103B, 103G, and 103R) with the electron-injection layer 109 and the insulating layers (107B, 107G, and 107R) therebetween. The EL layers (103B, 103G, 103R) illustrated in FIG. 7C include the hole-injection/transport layers (104R, 104G, and 104B), the light-emitting layers, and the electron-transport layers (108B-1\108B-2, 108G-1\108G-2, and 108R-1\108R-2). Thus, the EL layers (103B, 103G, and 103R) and the electrode 552, specifically the hole-injection/transport layers (104B, 104G, and 104R) in the EL layers (103B, 103G, and 103R) and the electrode 552 can be prevented from being electrically short-circuited.

Through the above steps, the EL layer 103B, the EL layer 103G, and the EL layer 103R in the light-emitting device 550B, the light-emitting device 550G, and the light-emitting device 550R can be processed to be separated from each other.

The EL layers (EL layers 103B, 103G, and 103R) are processed to be separated by patterning using a photolithography method; hence, a high-resolution light-emitting apparatus (display panel) can be fabricated. End portions (side surfaces) of the EL layer processed by patterning using a photolithography method have substantially one surface (or are positioned on substantially the same plane).

In the EL layer, especially the hole-injection layer, which is included in the hole-transport region between the anode and the light-emitting layer, often has high conductivity; thus, a hole-injection layer formed as a layer shared by adjacent light-emitting devices might cause crosstalk. Therefore, processing the EL layers to be separated by patterning using a photolithography method as shown in this structure example can suppress occurrence of crosstalk between adjacent light-emitting devices.

Structure Example 2 of Light-Emitting Apparatus 700

Figure 8:
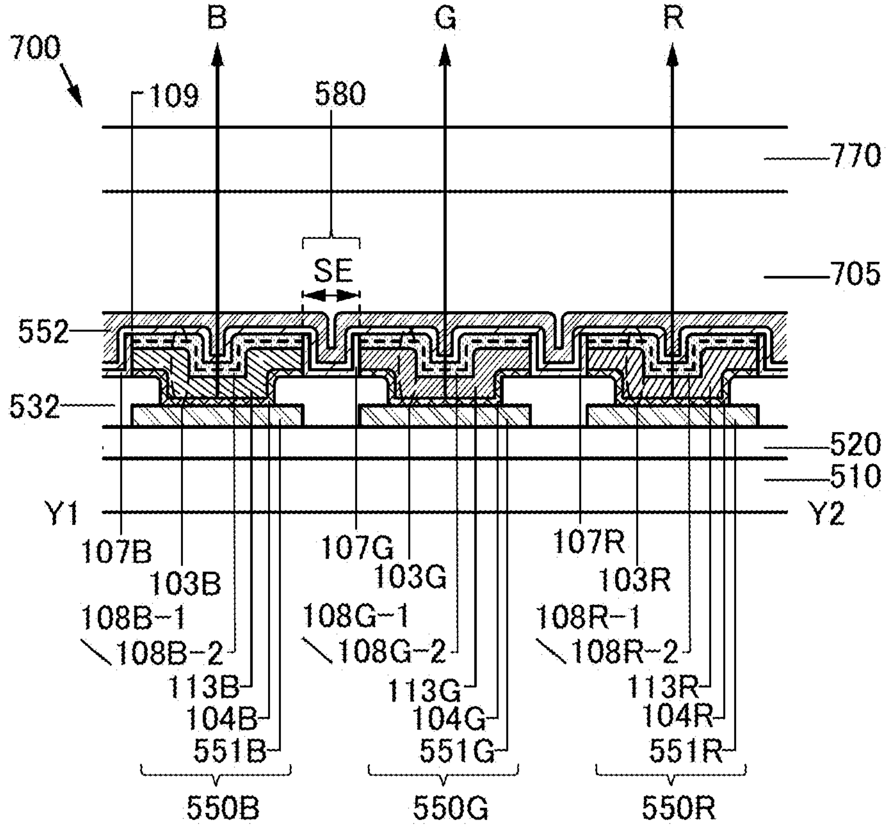
FIG. 8 illustrates a light-emitting apparatus of an embodiment.

The light-emitting apparatus 700 illustrated in FIG. 8 includes the light-emitting device 550B, the light-emitting device 550G, the light-emitting device 550R, and the partition 532. The light-emitting device 550B, the light-emitting device 550G, the light-emitting device 550R, and the partition 532 are formed over the functional layer 520 provided over the first substrate 510. The functional layer 520 includes, for example, the driver circuit GD, the driver circuit SD, and the like that are composed of a plurality of transistors, and wirings that electrically connect these circuits. Note that these driver circuits are electrically connected to the light-emitting device 550B, the light-emitting device 550G, and the light-emitting device 550R, for example, to drive them.

The light-emitting device 550B, the light-emitting device 550G, and the light-emitting device 550R each have the device structure described in Embodiments 1 and 2. Specifically, the case is described in which the EL layer 103 in the structure illustrated in FIG. 2A differs between the light-emitting devices.

Note that specific structures of the light-emitting devices illustrated in FIG. 8 are the same as the structures of the light-emitting devices 550B, 550G, and 550R described with reference to FIGS. 3A to 3D.

As illustrated in FIG. 8, the EL layers (103B, 103G, and 103R) of the light-emitting devices (550B, 550G, and 550R) each include the hole-injection/transport layer (104B, 104G, or 104R), the light-emitting layer (113B, 113G, or 113R), the electron-transport layer (108B-1108B-2, 108G-1108G-2, or 108R-1108R-2), and the electron-injection layer 109.

The EL layers (103B, 103G, and 103R) in this structure are processed to be separated by patterning using a photolithography method; hence, end portions (side surfaces) of the processed EL layers have substantially one surface (or are positioned on substantially the same plane).

The space 580 is provided between the adjacent light-emitting devices, each of which includes the EL layer (103B, 103G, or 103R). When the space 580 is denoted by a distance SE between the EL layers in adjacent light-emitting devices, decreasing the distance SE increases the aperture ratio and the resolution. By contrast, as the distance SE is increased, the effect of the difference in the fabrication process between the adjacent light-emitting devices becomes permissible, which leads to an increase in manufacturing yield. Since the light-emitting device fabricated according to this specification is suitable for a miniaturization process, the distance SE between the EL layers in the adjacent light-emitting devices can be longer than or equal to 0.5 μm and shorter than or equal to 5 μm, preferably longer than or equal to 1 μm and shorter than or equal to 3 μm, further preferably longer than or equal to 1 μm and shorter than or equal to 2.5 μm, and still further preferably longer than or equal to 1 μm and shorter than or equal to 2 μm. Typically, the distance SE is preferably longer than or equal to 1 μm and shorter than or equal to 2 (e.g., 1.5 μm or a neighborhood thereof).

In the EL layer, especially the hole-injection layer, which is included in the hole-transport region between the anode and the light-emitting layer, often has high conductivity; thus, a hole-injection layer formed as a layer shared by adjacent light-emitting devices might cause crosstalk. Therefore, processing the EL layers to be separated by patterning using a photolithography method as shown in this structure example can suppress occurrence of crosstalk between adjacent light-emitting devices.

In this specification and the like, a device formed using a metal mask or a fine metal mask (FMM) may be referred to as a device having a metal mask (MM) structure. In this specification and the like, a device formed without using a metal mask or an FMM may be referred to as a device having a metal maskless (MML) structure. A light-emitting apparatus having an MML structure is manufactured without using a metal mask and thus has higher flexibility in designing the pixel arrangement, the pixel shape, and the like than a light-emitting apparatus having an FMM structure or an MM structure.

Note that in the method for manufacturing a light-emitting apparatus having an MML structure, an island-shaped EL layer is formed not by processing with the use of a metal mask but by processing after formation of an EL layer. Accordingly, a light-emitting apparatus with a higher resolution or a higher aperture ratio than a conventional one can be achieved. Moreover, EL layers of different colors can be formed separately, which enables extremely vivid images; thus, a light-emitting apparatus with a high contrast and high display quality can be fabricated. Provision of a sacrificial layer over an EL layer can reduce damage on the EL layer during a fabrication process and increase the reliability of the light-emitting device.

As a way of processing the light-emitting layer into an island shape, there is performing processing by a photolithography method on the EL layer in which components up to the light-emitting layer are formed. In this way, damage to the light-emitting layer (e.g., processing damage) might significantly degrade the reliability. In view of the above, in the manufacture of the display panel of one embodiment of the present invention, a sacrificial layer or the like is preferably formed over a layer above the light-emitting layer (e.g., a carrier-transport layer or a carrier-injection layer, and specifically an electron-transport layer or an electron-injection layer), followed by the processing of the light-emitting layer into an island shape. Such a method provides a highly reliable display panel.

The structures described in this embodiment can be used in combination with any of the structures described in the other embodiments as appropriate.

Embodiment 4

In this embodiment, an apparatus 720 is described with reference to FIGS. 9A to 9F, FIGS. 10A to 10C, and FIGS. 11A and 11B. The apparatus 720 illustrated in FIG. 9A to FIG. 11B includes any of the light-emitting devices described in Embodiments 1 and 2 and therefore is a light-emitting apparatus. Furthermore, the apparatus 720 described in this embodiment can be used in a display portion of an electronic appliance or the like and therefore can also be referred to as a display panel or a display apparatus. Moreover, when the apparatus 720 includes the light-emitting device as a light source and a light-receiving device that can receive light from the light-emitting device, the apparatus 720 can be referred to as a light-emitting and light-receiving apparatus. Note that the light-emitting apparatus, the display panel, the display apparatus, and the light-emitting and light-receiving apparatus each include at least a light-emitting device.

Furthermore, the light-emitting apparatus, the display panel, the display apparatus, and the light-emitting and light-receiving apparatus of this embodiment can have high definition or large size. Therefore, the light-emitting apparatus, the display panel, the display apparatus, and the light-emitting and light-receiving apparatus of this embodiment can be used, for example, in display portions of electronic appliances such as a digital camera, a digital video camera, a digital photo frame, a mobile phone, a portable game console, a smart phone, a wristwatch terminal, a tablet terminal, a portable information terminal, and an audio reproducing apparatus, in addition to display portions of electronic appliances with a relatively large screen, such as a television apparatus, a desktop or laptop personal computer, a monitor of a computer or the like, digital signage, and a large game machine such as a pachinko machine.

Figure 9A:
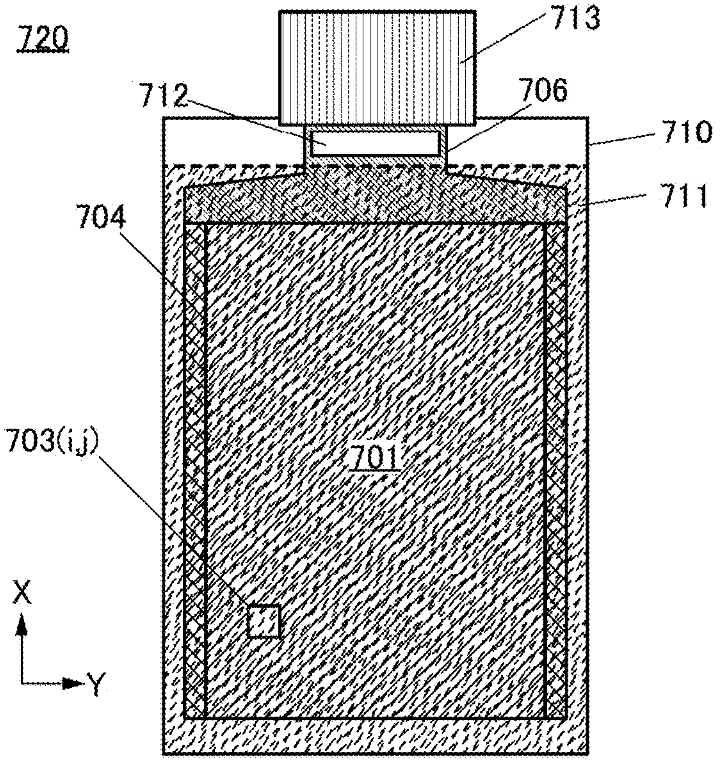
FIGS. 9A to 9F illustrate an apparatus of an embodiment and pixel arrangements.

FIG. 9A is a top view of the apparatus 720 (e.g., the light-emitting apparatus, the display panel, the display apparatus, and the light-emitting and light-receiving apparatus).

Figure 9B:
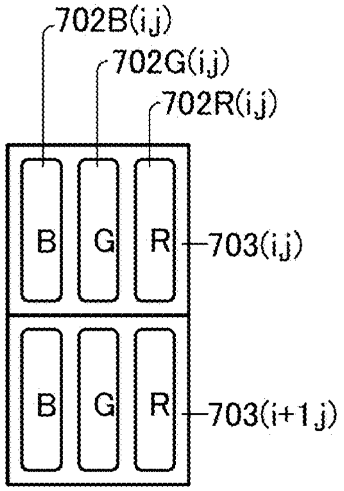

In FIG. 9A, the apparatus 720 has a structure in which a substrate 710 and a substrate 711 are attached to each other. In addition, the apparatus 720 includes a display region 701, a circuit 704, a wiring 706, and the like. Note that the display region 701 includes a plurality of pixels. As illustrated in FIG. 9B, a pixel 703(*i, j*) illustrated in FIG. 9A and a pixel 703(*i*+1, j) are adjacent to each other.

Furthermore, in the example of the apparatus 720 illustrated in FIG. 9A, the substrate 710 is provided with an integrated circuit (IC) 712 by a chip on glass (COG) method, a chip on film (COF) method, or the like. As the IC 712, an IC including a scan line driver circuit, a signal line driver circuit, or the like can be used, for example. In the example illustrated in FIG. 9A, an IC including a signal line driver circuit is used as the IC 712, and a scan line driver circuit is used as the circuit 704.

The wiring 706 has a function of supplying signals and power to the display region 701 and the circuit 704. The signals and power are input to the wiring 706 from the outside through a flexible printed circuit (FPC) 713 or to the wiring 706 from the IC 712. Note that the apparatus 720 is not necessarily provided with the IC. The IC may be mounted on the FPC by a COF method or the like.

FIG. 9B illustrates the pixel 703(*i,j*) and the pixel 703(*i*+1, j) of the display region 701. A plurality of kinds of subpixels including light-emitting devices that emit different color light from each other can be included in the pixel 703(*i,j*). Alternatively, a plurality of subpixels including light-emitting devices that emit the same color light may be included in addition to those described above. For example, the pixel can include three kinds of subpixels. The three subpixels can be of three colors of red (R), green (G), and blue (B) or of three colors of yellow (Y), cyan (C), and magenta (M), for example. Alternatively, the pixel can include four kinds of subpixels. The four subpixels can be of four colors of R, G, B, and white (W) or of four colors of R, G, B, and Y, for example. Specifically, the pixel 703(*i,j*) can consist of a subpixel 702B(i,j) for blue display, a subpixel 702G(i,j) for green display, and a subpixel 702R(i,j) for red display.

Other than the subpixels including the light-emitting devices, a subpixel including a light-receiving device may also be provided. In the case where the subpixel includes a light-receiving device, the apparatus 720 is also referred to as a light-emitting and light-receiving apparatus.

Figure 9C:
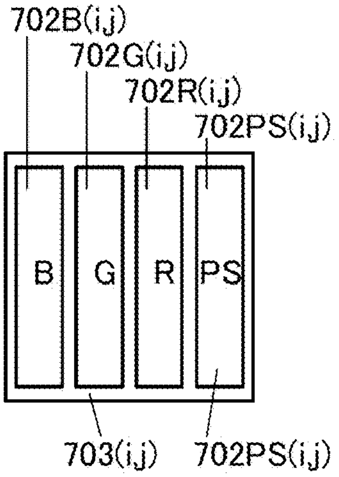
Figure 9D:
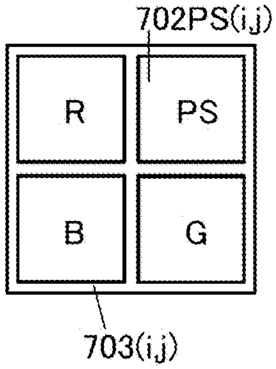
Figure 9E:
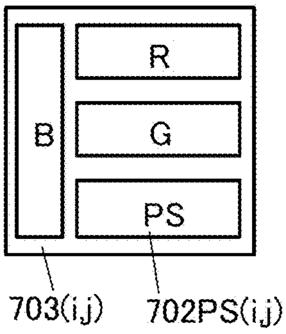

FIGS. 9C to 9F illustrate various layout examples of the pixel 703(*i,j*) including a subpixel 702PS(i,j) including a light-receiving device. The pixel arrangement in FIG. 9C is stripe arrangement, and the pixel arrangement in FIG. 9D is matrix arrangement. The pixel arrangement in FIG. 9E has a structure where three subpixels (the subpixels R, G, and PS) are vertically arranged next to one subpixel (the subpixel B). In the pixel arrangement in FIG. 9F, the vertically oriented three subpixels G, B, and R are arranged laterally, and the subpixel PS and the horizontally oriented subpixel IR are arranged laterally below the three subpixels. Note that the wavelength of light detected by the subpixel 702PS(i,j) is not particularly limited; however, the light-receiving device included in the subpixel 702PS(i,j) preferably has sensitivity to light emitted by the light-emitting device included in the subpixel 702R(i,j), the subpixel 702G(i,j), the subpixel 702B(i,j), or the subpixel 7021R(i,j). For example, the light-receiving device preferably detects one or more kinds of light in blue, violet, bluish violet, green, yellowish green, yellow, orange, red, and infrared wavelength ranges, for example.

Figure 9F:
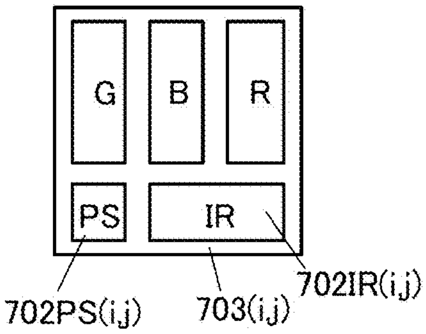

Furthermore, as illustrated in FIG. 9F, a subpixel 702IR (i,j) that emits infrared rays may be added to any of the above-described sets of subpixels in the pixel 703(*i,j*). Specifically, the subpixel 702IR(i,j) that emits light including light with a wavelength of higher than or equal to 650 nm and lower than or equal to 1000 nm may be used in the pixel 703(*i,j*).

Note that the arrangement of subpixels is not limited to the structures illustrated in FIGS. 9A to 9F and a variety of arrangement methods can be employed. The arrangement of subpixels may be stripe arrangement, S stripe arrangement, matrix arrangement, delta arrangement, Bayer arrangement, or pentile arrangement, for example.

Furthermore, top surfaces of the subpixels may have a triangular shape, a quadrangular shape (including a rectangular shape and a square shape), a polygonal shape such as a pentagonal shape, a polygonal shape with rounded corners, an elliptical shape, or a circular shape, for example. The top surface shape of a subpixel herein refers to a top surface shape of a light-emitting region of a light-emitting device.

Furthermore, in the case where not only a light-emitting device but also a light-receiving device is included in a pixel, the pixel has a light-receiving function and thus can detect a contact or approach of an object while displaying an image. For example, an image can be displayed by using all the subpixels included in a light-emitting apparatus; or light can be emitted by some of the subpixels as a light source and an image can be displayed by using the remaining subpixels.

Note that the light-receiving area of the subpixel 702PS (i,j) is preferably smaller than the light-emitting areas of the other subpixels. A smaller light-receiving area leads to a narrower image-capturing range, prevents a blur in a captured image, and improves the definition. Thus, by using the subpixel 702PS(i,j), high-resolution or high-definition image capturing is possible. For example, image capturing for personal authentication with the use of a fingerprint, a palm print, the iris, the shape of a blood vessel (including the shape of a vein and the shape of an artery), a face, or the like is possible by using the subpixel 702PS(i,j).

Moreover, the subpixel 702PS(i,j) can be used in a touch sensor (also referred to as a direct touch sensor), a near touch sensor (also referred to as a hover sensor, a hover touch sensor, a contactless sensor, or a touchless sensor), or the like. For example, the subpixel 702PS(i,j) preferably detects infrared light. Thus, touch sensing is possible even in a dark place.

Here, the touch sensor or the near touch sensor can detect an approach or contact of an object (e.g., a finger, a hand, or a pen). The touch sensor can detect the object when the light-emitting and light-receiving apparatus and the object come in direct contact with each other. Furthermore, the near touch sensor can detect the object even when the object is not in contact with the light-emitting and light-receiving apparatus. For example, the light-emitting and light-receiving apparatus can preferably detect the object when the distance between the light-emitting and light-receiving apparatus and the object is more than or equal to 0.1 mm and less than or equal to 300 nm, preferably more than or equal to 3 mm and less than or equal to 50 mm. With this structure, light-emitting and light-receiving apparatus can be controlled without the object directly contacting with the light-emitting and light-receiving apparatus. In other words, the light-emitting and light-receiving apparatus can be controlled in a contactless (touchless) manner. With the above-described structure, the light-emitting and light-receiving apparatus can be controlled with a reduced risk of making the light-emitting and light-receiving apparatus dirty or damaging the light-emitting and light-receiving apparatus or without the object directly touching a dirt (e.g., dust, bacteria, or a virus) attached to the display apparatus.

For high-resolution image capturing, the subpixel 702PS(i,j) is preferably provided in every pixel included in the light-emitting and light-receiving apparatus. Meanwhile, in the case where the subpixel 702PS(i,j) is used in a touch sensor, a near touch sensor, or the like, high accuracy is not required as compared to the case of capturing an image of a fingerprint or the like; accordingly, the subpixel 702PS(i,j) is provided in some subpixels in the light-emitting and light-receiving apparatus. When the number of subpixels 702PS(i,j) included in the light-emitting and light-receiving apparatus is smaller than the number of subpixels 702R(i,j) or the like, higher detection speed can be achieved.

Next, an example of a pixel circuit of a subpixel included in the light-emitting device is described with reference to FIG. 10A. A pixel circuit 530 illustrated in FIG. 10A includes a light-emitting device (EL) 550, a transistor M15, a transistor M16, a transistor M17, and a capacitor C3. Note that a light-emitting diode can be used as the light-emitting device 550. In particular, any of the light-emitting devices described in Embodiment 1 and Embodiment 2 is preferably used as the light-emitting device 550.

Figure 10A:
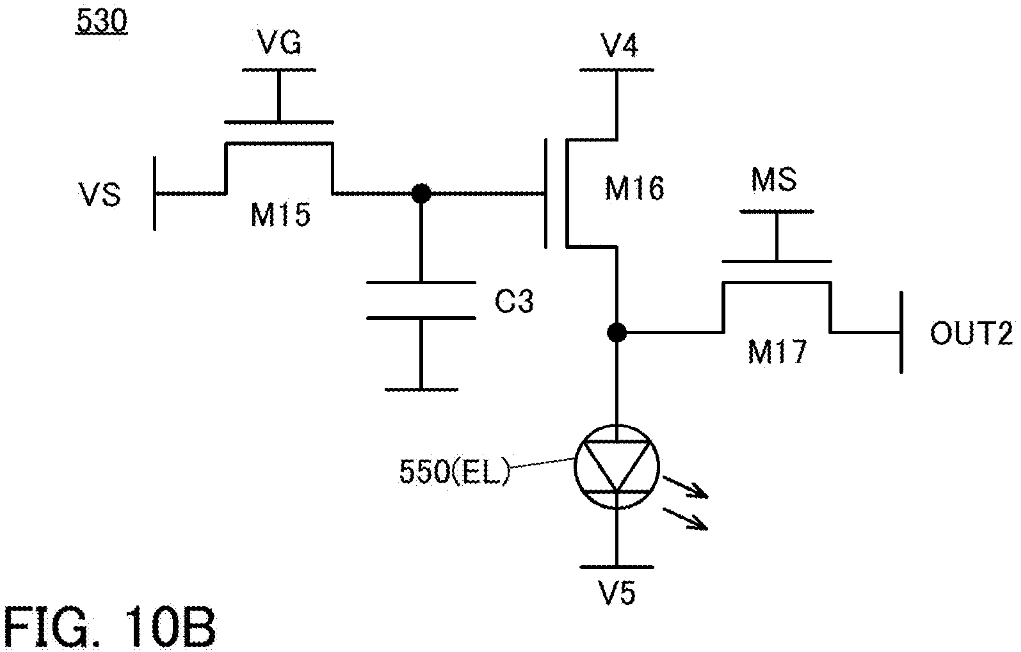
FIGS. 10A to 10C illustrate pixel circuits of an embodiment.

In FIG. 10A, a gate of the transistor M15 is electrically connected to a wiring VG, one of a source and a drain of the transistor M15 is electrically connected to a wiring VS, and the other of the source and the drain of the transistor M15 is electrically connected to one electrode of the capacitor C3 and a gate of the transistor M16. One of a source and a drain of the transistor M16 is electrically connected to a wiring V4, and the other is electrically connected to an anode of the light-emitting device 550 and one of a source and a drain of the transistor M17. A gate of the transistor M17 is electrically connected to a wiring MS, and the other of the source and the drain of the transistor M17 is electrically connected to a wiring OUT2. A cathode of the light-emitting device 550 is electrically connected to a wiring V5.

A constant potential is supplied to the wiring V4 and the wiring V5. In the light-emitting device 550, the anode side can have a high potential and the cathode side can have a lower potential than the anode side. The transistor M15 is controlled by a signal supplied to the wiring VG and functions as a selection transistor for controlling a selection state of the pixel circuit 530. The transistor M16 functions as a driving transistor that controls a current flowing through the light-emitting device 550 in accordance with a potential supplied to the gate of the transistor M16. When the transistor M15 is on, a potential supplied to the wiring VS is supplied to the gate of the transistor M16, and the luminance of the light-emitting device 550 can be controlled in accordance with the potential. The transistor M17 is controlled by a signal supplied to the wiring MS and has a function of outputting a potential between the transistor M16 and the light-emitting device 550 to the outside through the wiring OUT2.

Here, a transistor in which a metal oxide (an oxide semiconductor) is used in a semiconductor layer where a channel is formed is preferably used as transistors M11, M12, M13, and M14 included in a pixel circuit 530 in FIG. 10A and the transistors M15, M16, and M17 included in the pixel circuit 530.

A transistor using a metal oxide having a wider band gap and a lower carrier density than silicon can achieve an extremely low off-state current. Such a low off-state current enables retention of charges accumulated in a capacitor that is connected in series with the transistor for a long time. Therefore, it is particularly preferable to use a transistor including an oxide semiconductor as the transistors M11, M12, and M15 each of which is connected in series with a capacitor C2 or the capacitor C3. When each of the other transistors also includes an oxide semiconductor, manufacturing cost can be reduced.

Alternatively, transistors using silicon as a semiconductor in which a channel is formed can be used as the transistors M11 to M17. It is particularly preferable to use silicon with high crystallinity such as single crystal silicon or polycrystalline silicon because high field-effect mobility can be achieved and higher-speed operation can be performed.

Alternatively, a transistor including an oxide semiconductor may be used as at least one of the transistors M11 to M17, and transistors including silicon may be used as the other transistors.

Next, an example of a pixel circuit of a subpixel including a light-receiving device is described with reference to FIG. 10B. The pixel circuit 531 illustrated in FIG. 10B includes a light-receiving device (PD) 560, the transistor M11, the transistor M12, the transistor M13, the transistor M14, and the capacitor C2. In the example illustrated here, a photodiode is used as the light-receiving device (PD) 560.

Figure 10B:
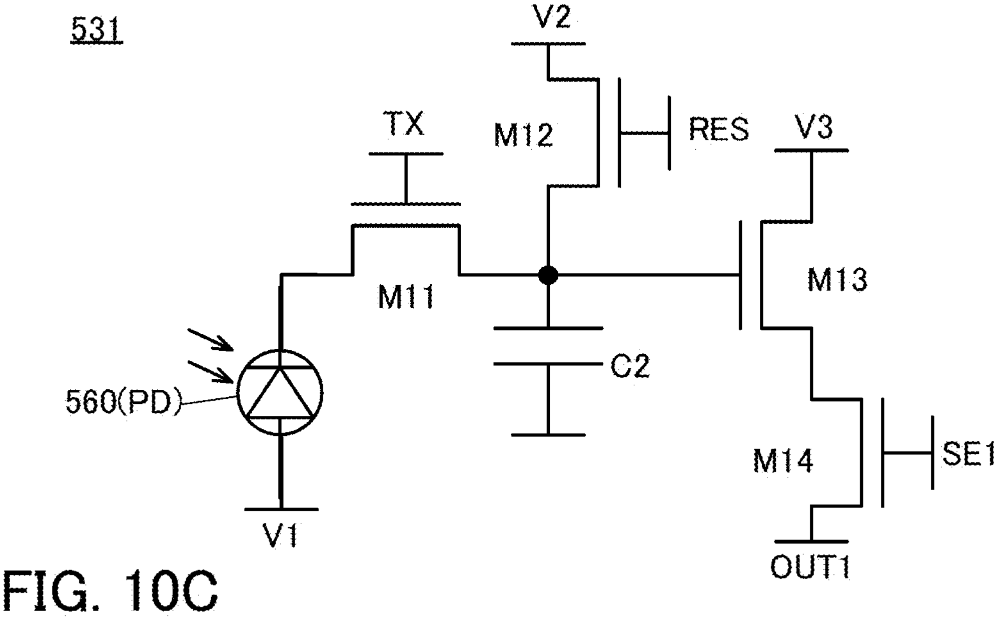

In FIG. 10B, an anode of the light-receiving device (PD) 560 is electrically connected to a wiring V1, and a cathode of the light-receiving device (PD) 560 is electrically connected to one of a source and a drain of the transistor M11. A gate of the transistor M11 is electrically connected to a wiring TX, and the other of the source and the drain of the transistor M11 is electrically connected to one electrode of the capacitor C2, one of a source and a drain of the transistor M12, and a gate of the transistor M13. A gate of the transistor M12 is electrically connected to a wiring RES, and the other of the source and the drain of the transistor M12 is electrically connected to a wiring V2. One of a source and a drain of the transistor M13 is electrically connected to a wiring V3, and the other of the source and the drain of the transistor M13 is electrically connected to one of a source and a drain of the transistor M14. A gate of the transistor M14 is electrically connected to a wiring SE1, and the other of the source and the drain of the transistor M14 is electrically connected to a wiring OUT1.

A constant potential is supplied to the wiring V1, the wiring V2, and the wiring V3. When the light-receiving device (PD) 560 is driven with a reverse bias, the wiring V2 is supplied with a potential higher than the potential of the wiring V1. The transistor M12 is controlled by a signal supplied to the wiring RES and has a function of resetting the potential of a node connected to the gate of the transistor M13 to a potential supplied to the wiring V2. The transistor M11 is controlled by a signal supplied to the wiring TX and has a function of controlling the timing at which the potential of the node changes, in accordance with a current flowing through the light-receiving device (PD) 560. The transistor M13 functions as an amplifier transistor for outputting a signal corresponding to the potential of the node. The transistor M14 is controlled by a signal supplied to the wiring SE and functions as a selection transistor for reading an output corresponding to the potential of the node by an external circuit connected to the wiring OUT1.

Although n-channel transistors are illustrated in FIGS. 10A and 10B, p-channel transistors can alternatively be used.

The transistors included in the pixel circuit 530 and the transistors included in the pixel circuit 531 are preferably formed side by side over the same substrate. It is particularly preferable that the transistors included in the pixel circuit 530 and the transistors included in the pixel circuit 531 be periodically arranged in one region.

One or more layers including the transistor and/or the capacitor are preferably provided to overlap with the light-receiving device (PD) 560 or the light-emitting device (EL) 550. Thus, the effective area of each pixel circuit can be reduced, and a high-resolution light-receiving portion or display portion can be achieved.

Figure 10C:
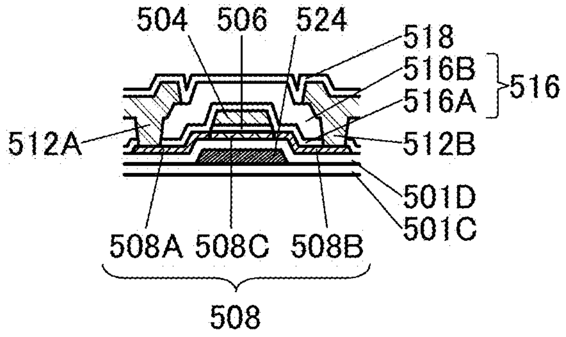

FIG. 10C illustrates an example of a specific structure of a transistor that can be used in the pixel circuit described with reference to FIGS. 10A and 10B. As the transistor, a bottom-gate transistor, a top-gate transistor, or the like can be used as appropriate.

The transistor illustrated in FIG. 10C includes a semiconductor film 508, a conductive film 504, an insulating film 506, a conductive film 512A, and a conductive film 512B. The transistor is formed over an insulating film 501C, for example. The transistor also includes an insulating film 516 (an insulating film 516A and an insulating film 516B) and an insulating film 518.

The semiconductor film 508 includes a region 508A electrically connected to the conductive film 512A and a region 508B electrically connected to the conductive film 512B. The semiconductor film 508 includes a region 508C between the region 508A and the region 508B.

The conductive film 504 includes a region overlapping with the region 508C and has a function of a gate electrode.

The insulating film 506 includes a region positioned between the semiconductor film 508 and the conductive film 504. The insulating film 506 has a function of a first gate insulating film.

The conductive film 512A has one of a function of a source electrode and a function of a drain electrode, and the conductive film 512B has the other.

A conductive film 524 can be used in the transistor. The semiconductor film 508 is sandwiched between the conductive film 504 and a region included in the conductive film 524. The conductive film 524 has a function of a second gate electrode. An insulating film 501D is positioned between the semiconductor film 508 and the conductive film 524 and has a function of a second gate insulating film.

The insulating film 516 functions as, for example, a protective film covering the semiconductor film 508. Specifically, a film including a silicon oxide film, a silicon oxynitride film, a silicon nitride oxide film, a silicon nitride film, an aluminum oxide film, a hafnium oxide film, an yttrium oxide film, a zirconium oxide film, a gallium oxide film, a tantalum oxide film, a magnesium oxide film, a lanthanum oxide film, a cerium oxide film, or a neodymium oxide film can be used as the insulating film 516, for example.

For the insulating film 518, a material that has a function of inhibiting diffusion of oxygen, hydrogen, water, an alkali metal, an alkaline earth metal, and the like is preferably used. Specifically, the insulating film 518 can be formed using silicon nitride, silicon oxynitride, aluminum nitride, or aluminum oxynitride, for example. In each of silicon oxynitride and aluminum oxynitride, the number of nitrogen atoms contained is preferably larger than the number of oxygen atoms contained.

Note that in a step of forming the semiconductor film used in the transistor of the pixel circuit, the semiconductor film used in the transistor of the driver circuit can be formed. A semiconductor film having the same composition as the semiconductor film used in the transistor of the pixel circuit can be used in the driver circuit, for example.

The semiconductor film 508 preferably contains indium, M (M is one or more of gallium, aluminum, silicon, boron, yttrium, tin, copper, vanadium, beryllium, titanium, iron, nickel, germanium, zirconium, molybdenum, lanthanum, cerium, neodymium, hafnium, tantalum, tungsten, and magnesium), and zinc, for example. Specifically, M is preferably one or more of aluminum, gallium, yttrium, and tin.

It is particularly preferable that an oxide containing indium (In), gallium (Ga), and zinc (Zn) (also referred to as IGZO) be used as the semiconductor film 508. Alternatively, it is preferable to use an oxide containing indium, tin, and zinc. Further alternatively, it is preferable to use an oxide containing indium, gallium, tin, and zinc. Further alternatively, it is preferable to use an oxide containing indium (In), aluminum (Al), and zinc (Zn) (also referred to as IAZO). Further alternatively, it is preferable to use an oxide containing indium (In), aluminum (Al), gallium (Ga), and zinc (Zn) (also referred to as IAGZO).

When the semiconductor film is an In-M-Zn oxide, the atomic ratio of In is preferably greater than or equal to the atomic ratio of M in the In-M-Zn oxide. Examples of the atomic ratio of the metal elements in such an In-M-Zn oxide are In:M:Zn=1:1:1, 1:1:1.2, 1:3:2, 1:3:4, 2:1:3, 3:1:2, 4:2:3, 4:2:4.1, 5:1:3, 5:1:6, 5:1:7, 5:1:8, 6:1:6, and 5:2:5 and a composition in the vicinity of any of the above atomic ratios. Note that the vicinity of the atomic ratio includes ±30% of an intended atomic ratio.

For example, in the case of describing an atomic ratio of In:Ga:Zn=4:2:3 or a composition in the vicinity thereof, the case is included in which with the atomic proportion of In being 4, the atomic proportion of Ga is greater than or equal to 1 and less than or equal to 3 and the atomic proportion of Zn is greater than or equal to 2 and less than or equal to 4. In the case of describing an atomic ratio of In:Ga:Zn=5:1:6 or a composition in the vicinity thereof, the case is included in which with the atomic proportion of In being 5, the atomic proportion of Ga is greater than 0.1 and less than or equal to 2 and the atomic proportion of Zn is greater than or equal to 5 and less than or equal to 7. In the case of describing an atomic ratio of In:Ga:Zn=1:1:1 or a composition in the vicinity thereof, the case is included in which with the atomic proportion of In being 1, the atomic proportion of Ga is greater than 0.1 and less than or equal to 2 and the atomic proportion of Zn is greater than 0.1 and less than or equal to 2.

There is no particular limitation on the crystallinity of a semiconductor material used in the transistor, and an amorphous semiconductor or a semiconductor having crystallinity (a microcrystalline semiconductor, a polycrystalline semiconductor, a single crystal semiconductor, or a semiconductor partly including crystal regions) can be used. It is preferable to use a semiconductor having crystallinity, in which case deterioration of transistor characteristics can be suppressed.

It is preferable that a semiconductor layer of a transistor contain a metal oxide (also referred to as an oxide semiconductor). As an oxide semiconductor having crystallinity, a c-axis aligned crystalline oxide semiconductor (CAAC-OS), a nanocrystalline oxide semiconductor (nc-OS), and the like are given.

Alternatively, a transistor using silicon in its channel formation region (a Si transistor) may be used. Examples of silicon include single crystal silicon (single crystal Si), polycrystalline silicon, and amorphous silicon. In particular, a transistor containing low-temperature polysilicon (LTPS) in its semiconductor layer (hereinafter also referred to as an LTPS transistor) can be used. The LTPS transistor has high field-effect mobility and excellent frequency characteristics.

With the use of Si transistors such as LTPS transistors, a circuit required to drive at a high frequency (e.g., a source driver circuit) can be formed on the same substrate as the display portion. This allows simplification of an external circuit mounted on the light-emitting apparatus and a reduction in costs of parts and mounting costs.

An OS transistor has much higher field-effect mobility than a transistor containing amorphous silicon. In addition, the OS transistor has an extremely low leakage current between a source and a drain in an off state (hereinafter also referred to as off-state current), and charge accumulated in a capacitor that is connected in series to the transistor can be held for a long period. Furthermore, the power consumption of the light-emitting apparatus can be reduced with the OS transistor.

The off-state current per micrometer of channel width of the OS transistor at room temperature can be lower than or equal to 1 aA ($1\times10^{-18}$ A), lower than or equal to 1 zA ($1\times10^{-21}$ A), or lower than or equal to 1 yA ($1\times10^{-24}$ A). Note that the off-state current per micrometer of channel width of a Si transistor at room temperature is higher than or equal to 1 fA ($1\times10'$ A) and lower than or equal to 1 pA ($1\times10^{-12}$ A). In other words, the off-state current of the OS transistor is lower than that of the Si transistor by approximately ten orders of magnitude.

To increase the luminance of the light-emitting device included in the pixel circuit, the amount of current fed through the light-emitting device needs to be increased. To increase the current amount, the source-drain voltage of a driving transistor included in the pixel circuit needs to be increased. An OS transistor has a higher withstand voltage between a source and a drain than a Si transistor; hence, high voltage can be applied between the source and the drain of the OS transistor. Thus, with use of an OS transistor as a driving transistor included in the pixel circuit, the amount of current flowing through the light-emitting device can be increased, resulting in an increase in emission luminance of the light-emitting device.

When transistors operate in a saturation region, a change in source-drain current relative to a change in gate-source voltage can be smaller in an OS transistor than in a Si transistor. Accordingly, when an OS transistor is used as the driving transistor in the pixel circuit, a current flowing between the source and the drain can be set minutely by a change in gate-source voltage; hence, the amount of current flowing through the light-emitting device can be controlled. Consequently, the number of gray levels expressed by the pixel circuit can be increased.

Regarding saturation characteristics of current flowing when transistors operates in a saturation region, even in the case where the source-drain voltage of an OS transistor increases gradually, a more stable current (saturation current) can be fed through the OS transistor than through a Si transistor. Thus, by using an OS transistor as the driving transistor, a stable current can be fed through light-emitting devices even when the current-voltage characteristics of the light-emitting devices vary, for example. In other words, when the OS transistor operates in the saturation region, the source-drain current hardly changes with an increase in the source-drain voltage; hence, the luminance of the light-emitting device can be stable.

As described above, by using an OS transistor as the driving transistor included in the pixel circuit, it is possible to prevent black-level degradation, increase the luminance, increase the number of gray levels, and suppress variations in characteristics of light-emitting devices, for example.

The semiconductor film used in the transistor of the driver circuit can be formed in the same step as the semiconductor film used in the transistor of the pixel circuit. The driver circuit can be formed over a substrate where the pixel circuit is formed. The number of components of an electronic appliance can be reduced.

Alternatively, silicon film be used for the semiconductor film 508. Examples of silicon include single crystal silicon, polycrystalline silicon, and amorphous silicon. In particular, a transistor containing low-temperature polysilicon (LTPS) in its semiconductor layer (hereinafter also referred to as an LTPS transistor) is preferably used. The LTPS transistor has high field-effect mobility and excellent frequency characteristics.

With the use of transistors using silicon such as LTPS transistors, a circuit required to drive at a high frequency (e.g., a source driver circuit) can be formed on the same substrate as the display portion. This allows simplification of an external circuit mounted on the light-emitting apparatus and a reduction in costs of parts and mounting costs.

It is preferable to use a transistor containing a metal oxide (hereinafter also referred to as an oxide semiconductor) in a semiconductor layer where a channel is formed (hereinafter such a transistor is also referred to as an OS transistor) as at least one of the transistors included in the pixel circuit. The OS transistor has much higher field-effect mobility than a transistor containing amorphous silicon. In addition, the OS transistor has an extremely low leakage current between a source and a drain in an off state (hereinafter also referred to as off-state current), and charge accumulated in a capacitor that is connected in series to the transistor can be held for a long period. Furthermore, the power consumption of the light-emitting apparatus can be reduced with the OS transistor.

When an LTPS transistor is used as one or more of the transistors included in the pixel circuit and an OS transistor is used as the rest, the light-emitting apparatus can have low power consumption and high driving capability. As a favorable example, it is preferable that an OS transistor be used as a transistor functioning as a switch for controlling electrical continuity between wirings and an LTPS transistor be used as a transistor for controlling current, for instance. A structure where an LTPS transistor and an OS transistor are used in combination may be referred to as LTPO. The use of LTPO enables the display panel to have low power consumption and high drive capability.

For example, one of the transistors included in the pixel circuit functions as a transistor for controlling a current flowing through the light-emitting device and can be referred to as a driving transistor. One of a source and a drain of the driving transistor is electrically connected to the pixel electrode of the light-emitting device. An LTPS transistor is preferably used as the driving transistor. Accordingly, the amount of current flowing through the light-emitting device can be increased in the pixel circuit.

Another transistor included in the pixel circuit functions as a switch for controlling selection and non-selection of the pixel and can be referred to as a selection transistor. A gate of the selection transistor is electrically connected to a gate line, and one of a source and a drain thereof is electrically connected to a source line (signal line). An OS transistor is preferably used as the selection transistor. Accordingly, the gray level of the pixel can be maintained even with an extremely low frame frequency (e.g., 1 fps or less); thus, power consumption can be reduced by stopping the driver in displaying a still image.

In the case of using an oxide semiconductor in a semiconductor film, the apparatus 720 includes a light-emitting device including an oxide semiconductor in its semiconductor film and having a metal maskless (MML). With this structure, the leakage current that might flow through the transistor and the leakage current that might flow between adjacent light-emitting elements (also referred to as a lateral leakage current, a side leakage current, or the like) can become extremely low. With the structure, a viewer can observe any one or more of the image clearness, the image sharpness, a high chroma, and a high contrast ratio in an image displayed on the display apparatus. When the leakage current that might flow through the transistor and the lateral leakage current that might flow between light-emitting elements are extremely low, display with little leakage of light at the time of black display (so-called black floating) (such display is also referred to as deep black display) can be achieved.

In particular, in the case where a light-emitting device having an MML structure employs the above-described SBS structure, a layer provided between light-emitting elements (for example, also referred to as an organic layer or a common layer which is commonly used between the light-emitting elements) is disconnected; accordingly, display with no or extremely small lateral leakage can be achieved.

The structure of the transistors used in the display panel may be selected as appropriate depending on the size of the screen of the display panel. For example, single crystal Si transistors can be used in the display panel with a screen diagonal of 0.1 to 3 inches inclusive. In addition, LTPS transistors can be used in the display panel with a screen diagonal of 0.1 to 30 inches inclusive, preferably 1 to 30 inches inclusive. In addition, LTPO transistors (where an LTPS transistor and an OS transistor are used in combination) can be used in the display panel with a screen diagonal of 0.1 to 50 inches inclusive, preferably 1 to 50 inches inclusive. In addition, OS transistors can be used in the display panel with a screen diagonal of 0.1 to 200 inches inclusive, preferably 50 to 100 inches inclusive.

With the use of single crystal Si transistors, an increase in screen size is extremely difficult due to the size of a single crystal Si substrate. Furthermore, since a laser crystallization apparatus is used in the fabrication process, LTPS transistors are unlikely to respond to an increase in screen size (typically to a screen diagonal greater than 30 inches). By contrast, since the fabrication process does not necessarily require a laser crystallization apparatus or the like or can be performed at a relatively low temperature (typically, lower than or equal to 450° C.), OS transistors can be applied to a display panel with a relatively large area (typically, a screen diagonal of 50 to 100 inches inclusive). In addition, LTPO can be applied to a display panel with a size (typically, a screen diagonal of 1 to 50 inches inclusive) midway between the structure using LTPS transistors and the structure using OS transistors.

Figure 11A:
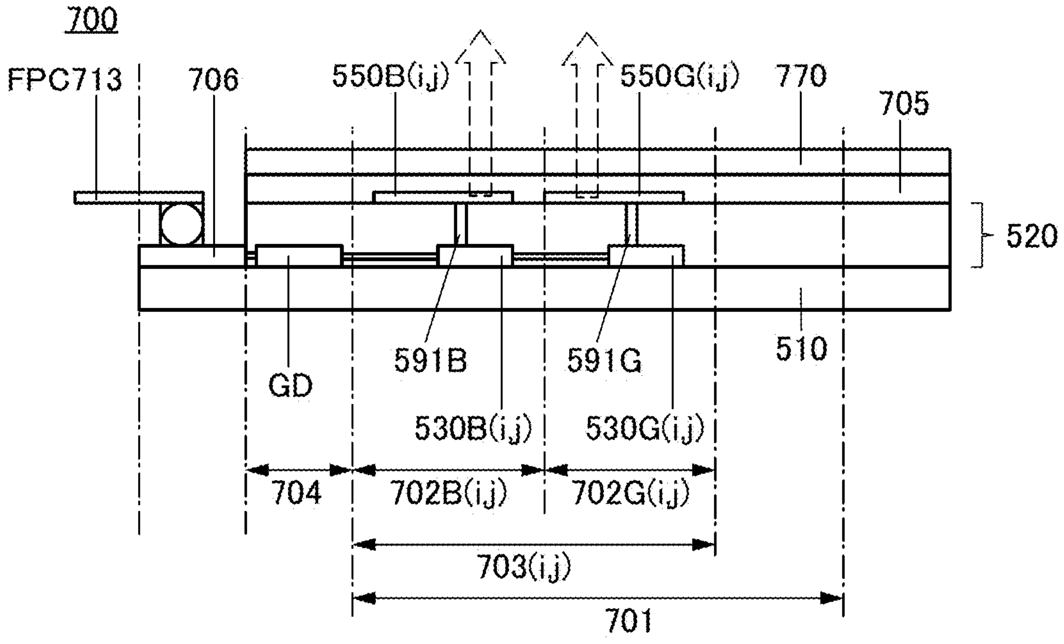
FIGS. 11A and 11B illustrate light-emitting apparatuses of an embodiment.
Figure 11B:
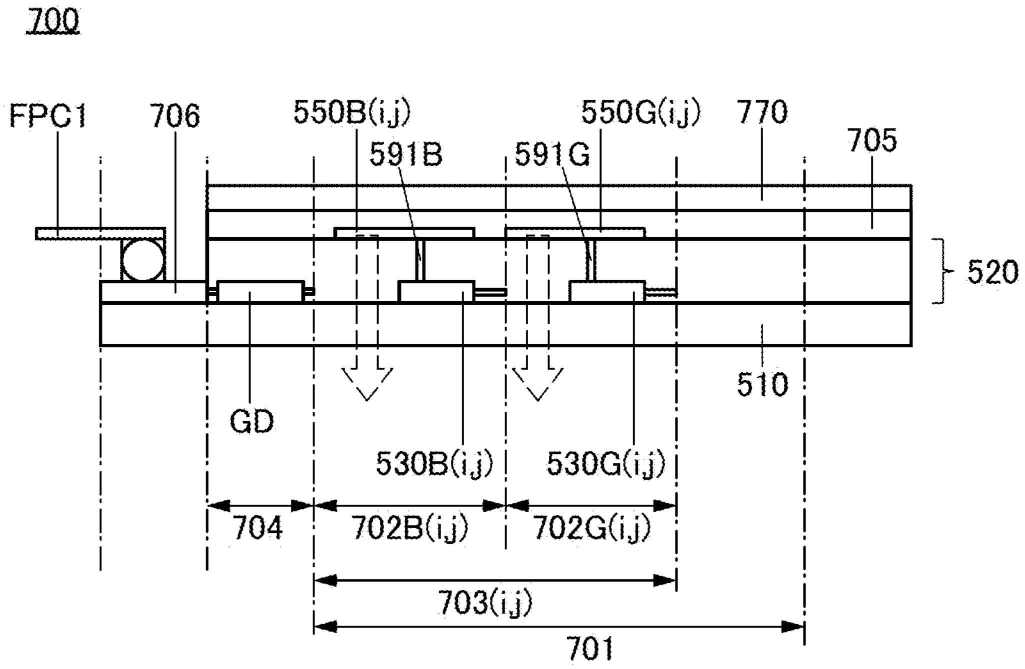

Next, FIGS. 11A and 11B are each a cross-sectional view of the apparatus.

FIGS. 11A and 11B are cross-sectional views of the apparatus illustrated in FIG. 9A of the case where the apparatus is a light-emitting apparatus. Specifically, FIGS. 11A and 11B are cross-sectional views of part of a region including the FPC 713 and the wiring 706 and part of the display region 701 including the pixel 703(*i,j*). FIG. 11A illustrates the light-emitting apparatus having a structure in which light is extracted in the upward direction of the drawing (to the second substrate 770 side) (the structure is referred to as a top emission structure), and FIG. 11B illustrates the light-emitting apparatus having a structure in which light is extracted in the downward direction of the drawing (to the first substrate 510 side) (the structure is referred to as a bottom emission structure).

In FIG. 11A, the apparatus (light-emitting apparatus) 700 includes the functional layer 520 between the first substrate 510 and the second substrate 770. The functional layer 520 includes, as well as the above-described transistors (M15, M16, and M17), the capacitor (C3), and the like, wirings electrically connected to these components (VS, VG, V4, and V5), for example. FIG. 11A illustrates the functional layer 520 including a pixel circuit 530B(i,j), a pixel circuit 530G(i,j), and the driver circuit GD, the functional layer 520 is not limited thereto.

Each pixel circuit (e.g., the pixel circuit 530B(i,j) and the pixel circuit 530G(i,j) in FIG. 11A) included in the functional layer 520 is electrically connected to a light-emitting device (e.g., a light-emitting device 550B(i,j) and a light-emitting device 550G(i,j) in FIG. 11A) formed over the functional layer 520. Specifically, the light-emitting device 550B(i,j) is electrically connected to the pixel circuit 530B(i,j) through a wiring 591B, and the light-emitting device 550G(i,j) is electrically connected to the pixel circuit 530G(i,j) through a wiring 591G. The insulating layer 705 is provided over the functional layer 520 and the light-emitting devices, and has a function of attaching the second substrate 770 and the functional layer 520.

As the second substrate 770, a substrate where touch sensors are arranged in a matrix can be used. For example, a substrate provided with capacitive touch sensors or optical touch sensors can be used as the second substrate 770. Thus, the light-emitting apparatus of one embodiment of the present invention can be used as a touch panel.

Although FIGS. 11A and 11B illustrate active-matrix light-emitting apparatuses, the structure of the light-emitting device described in Embodiments 1 and 2 may be applied to a passive-matrix light-emitting apparatus.

Embodiment 5

In this embodiment, structures of electronic appliances of embodiments of the present invention will be described with reference to FIGS. 12A to 12E, FIGS. 13A to 13E, and FIGS. 14A and 14B.

Figure 12A:
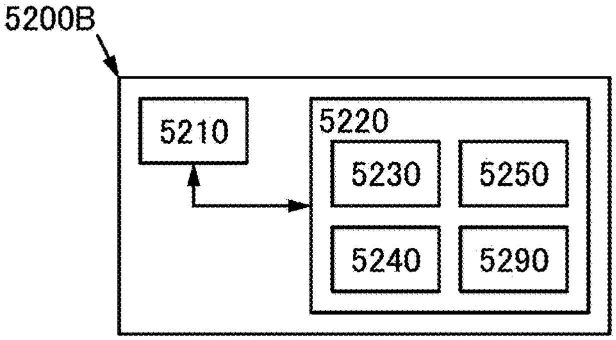
FIGS. 12A to 12E illustrate electronic appliances of an embodiment.
Figure 12B:
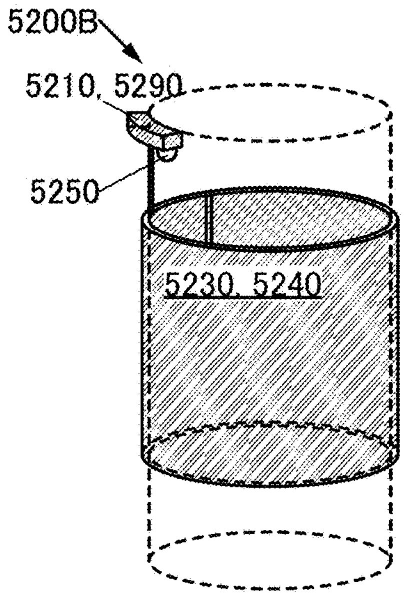
Figure 12C:
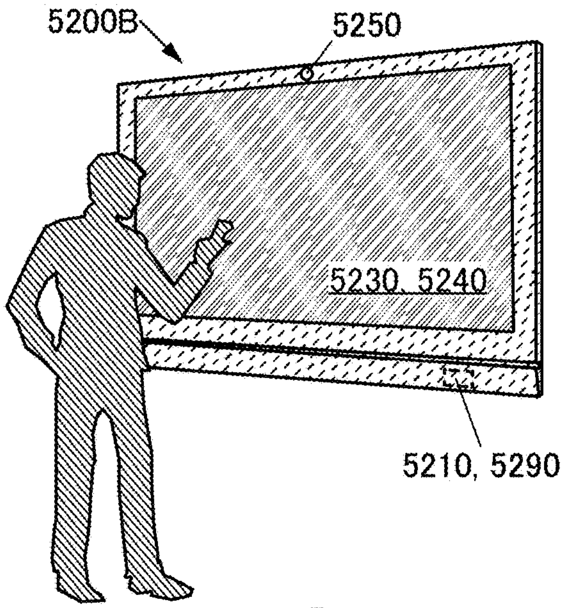
Figure 12D:
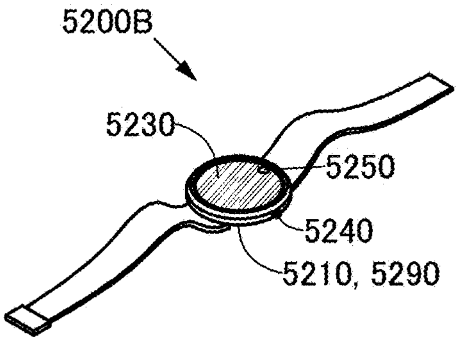
Figure 12E:
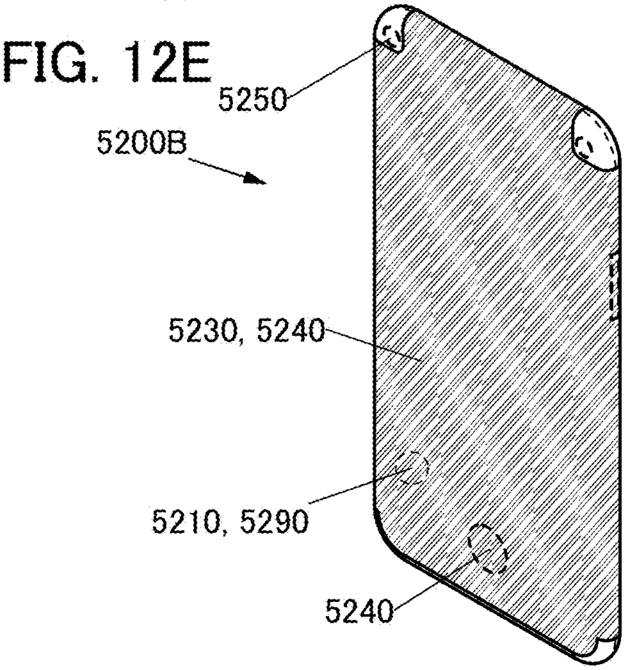
Figure 13A:
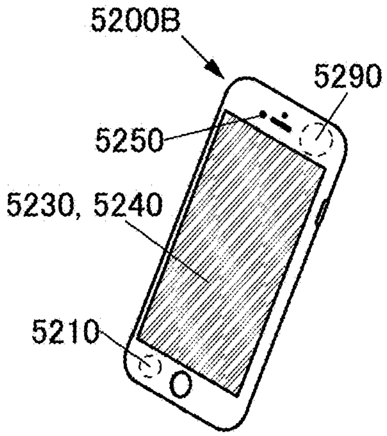
FIGS. 13A to 13E illustrate electronic appliances of embodiments.
Figure 13B:
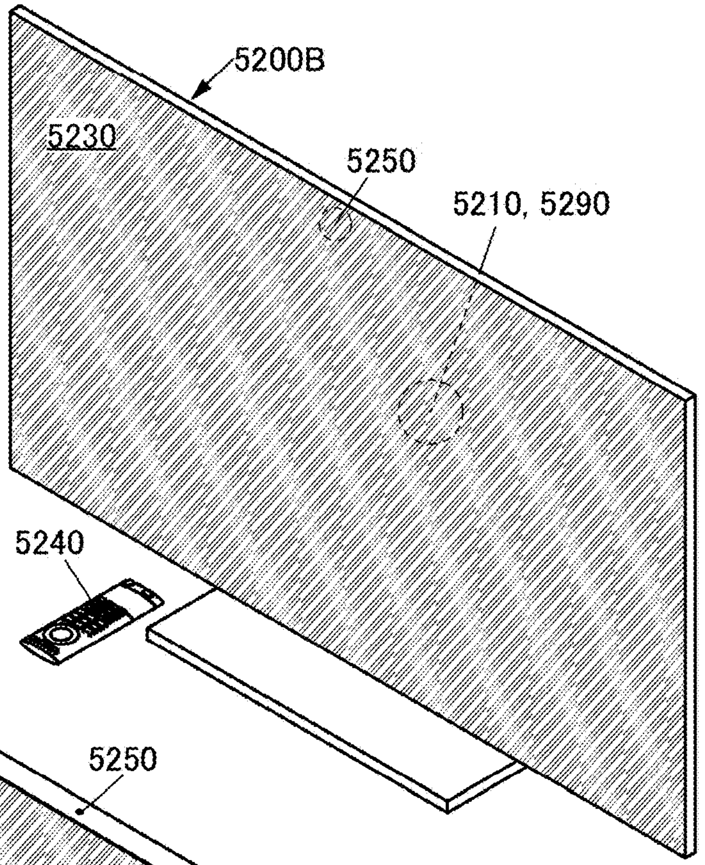
Figure 13C:
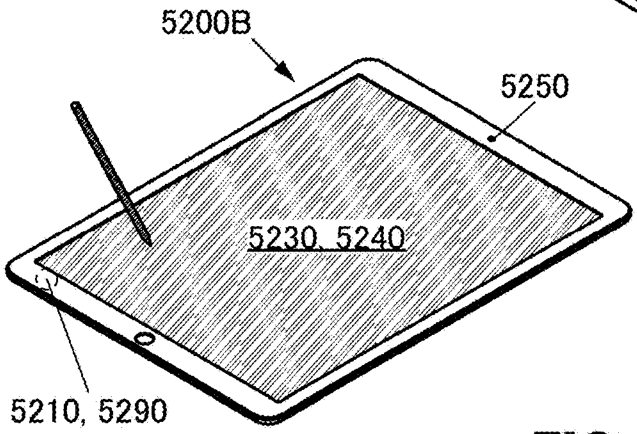
Figure 13D:
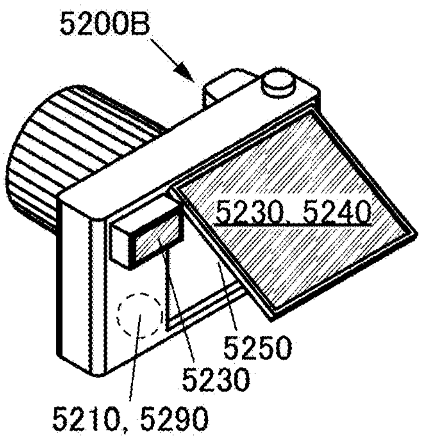
Figure 13E:
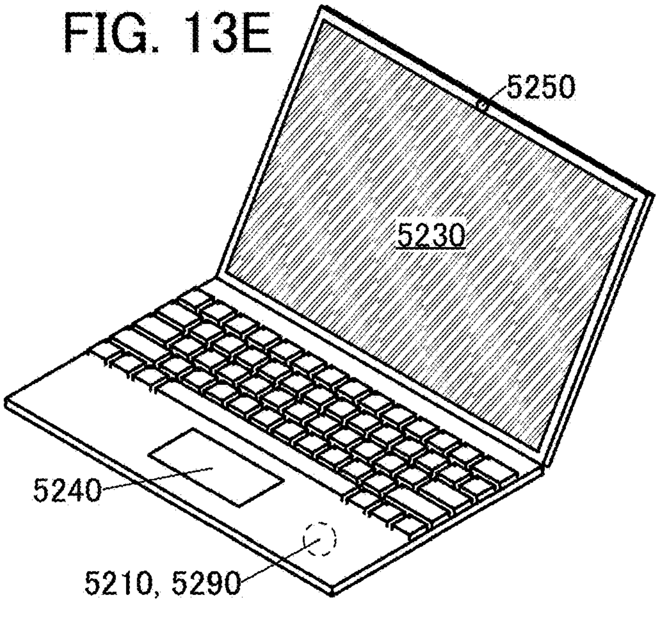
Figure 14A:
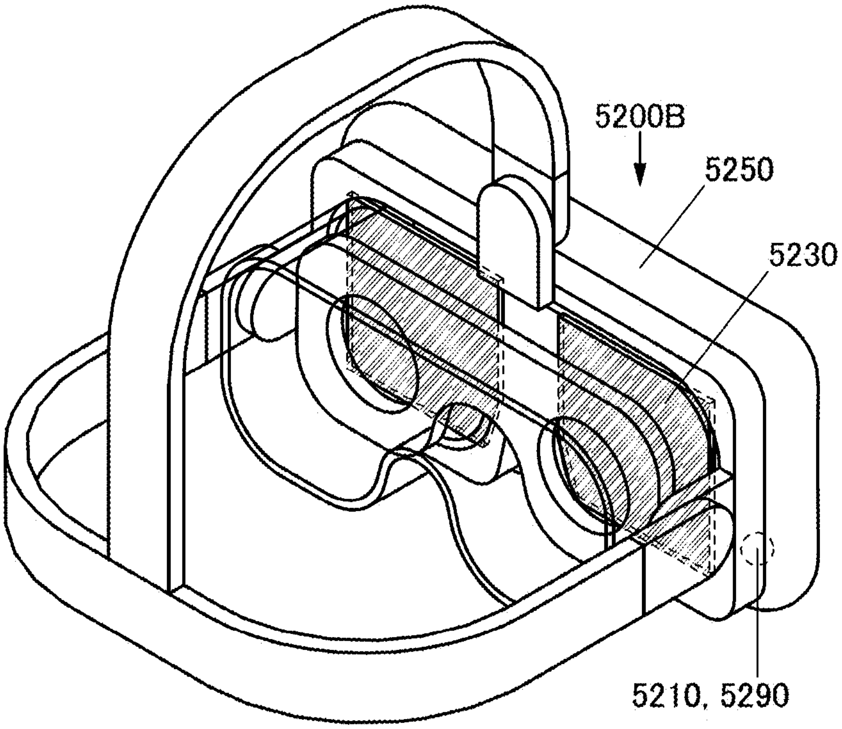
FIGS. 14A and 14B illustrate electronic appliances of an embodiment.
Figure 14B:
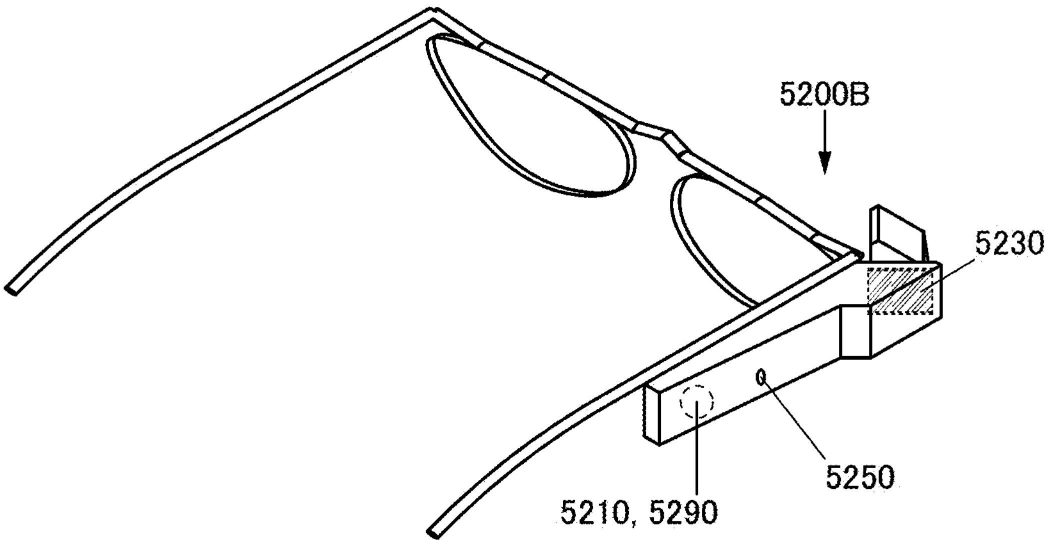

FIG. 12A to FIG. 14B each illustrate a structure of an electronic appliance of one embodiment of the present invention. FIG. 12A is a block diagram of an electronic appliance and FIGS. 12B to 12E are perspective views illustrating structures of electronic appliances. FIGS. 13A to 13E are perspective views illustrating structures of electronic appliances. FIGS. 14A and 14B are perspective views illustrating structures of electronic appliances.

An electronic appliance 5200B described in this embodiment includes an arithmetic device 5210 and an input/output device 5220 (see FIG. 12A).

The arithmetic device 5210 has a function of receiving handling data and a function of supplying image data on the basis of the handling data.

The input/output device 5220 includes a display unit 5230, an input unit 5240, a sensor unit 5250, and a communication unit 5290, and has a function of supplying handling data and a function of receiving image data. The input/output device 5220 also has a function of supplying sensing data, a function of supplying communication data, and a function of receiving communication data.

The input unit 5240 has a function of supplying handling data. For example, the input unit 5240 supplies handling data on the basis of handling by a user of the electronic appliance 5200B.

Specifically, a keyboard, a hardware button, a pointing device, a touch sensor, an illuminance sensor, an imaging device, an audio input device, an eye-gaze input device, an attitude sensing device, or the like can be used as the input unit 5240.

The display unit 5230 includes a display panel and has a function of displaying image data. For example, the display panel described in Embodiment 3 can be used for the display unit 5230.

The sensor unit 5250 has a function of supplying sensing data. For example, the sensor unit 5250 has a function of sensing a surrounding environment where the electronic appliance is used and supplying the sensing data.

Specifically, an illuminance sensor, an imaging device, an attitude sensing device, a pressure sensor, a human motion sensor, or the like can be used as the sensor unit 5250.

The communication unit 5290 has a function of receiving and supplying communication data. For example, the communication unit 5290 has a function of being connected to another electronic appliance or a communication network by wireless communication or wired communication. Specifically, the communication unit 5290 has a function of wireless local area network communication, telephone communication, near field communication, or the like.

FIG. 12B illustrates an electronic appliance having an outer shape along a cylindrical column or the like. An example of such an electronic appliance is digital signage. The display panel of one embodiment of the present invention can be used for the display unit 5230. The electronic appliance may have a function of changing its display method in accordance with the illuminance of a usage environment. The electronic appliance has a function of changing the displayed content when sensing the existence of a person. Thus, for example, the electronic appliance can be provided on a column of a building. The electronic appliance can display advertising, guidance, or the like.

FIG. 12C illustrates an electronic appliance having a function of generating image data on the basis of the path of a pointer used by the user. Examples of such an electronic appliance include an electronic blackboard, an electronic bulletin board, and digital signage. Specifically, a display panel with a diagonal size of 20 inches or longer, preferably 40 inches or longer, further preferably 55 inches or longer can be used. A plurality of display panels can be arranged and used as one display region. Alternatively, a plurality of display panels can be arranged and used as a multiscreen.

FIG. 12D illustrates an electronic appliance that is capable of receiving data from another device and displaying the data on the display unit 5230. An example of such an electronic appliance is a wearable electronic appliance. Specifically, the electronic appliance can display several options, and the user can choose some from the options and send a reply to the data transmitter. As another example, the electronic appliance has a function of changing its display method in accordance with the illuminance of a usage environment. Thus, for example, power consumption of the wearable electronic appliance can be reduced. As another example, the wearable electronic appliance can display an image so as to be suitably used even in an environment under strong external light, e.g., outdoors in fine weather.

FIG. 12E illustrates an electronic appliance including the display unit 5230 having a surface gently curved along a side surface of a housing. An example of such an electronic appliance is a mobile phone. The display unit 5230 includes a display panel that has a function of displaying images on the front surface, the side surfaces, the top surface, and the rear surface, for example. Thus, a mobile phone can display data on not only its front surface but also its side surfaces, top surface, and rear surface, for example.

FIG. 13A illustrates an electronic appliance that is capable of receiving data via the Internet and displaying the data on the display unit 5230. An example of such an electronic appliance is a smartphone. For example, the user can check a created message on the display unit 5230 and send the created message to another device. As another example, the electronic appliance has a function of changing its display method in accordance with the illuminance of a usage environment. Thus, power consumption of the smartphone can be reduced. As another example, it is possible to obtain a smartphone which can display an image such that the smartphone can be suitably used in an environment under strong external light, e.g., outdoors in fine weather.

FIG. 13B illustrates an electronic appliance that can use a remote controller as the input unit 5240. An example of such an electronic appliance is a television system. For example, data received from a broadcast station or via the Internet can be displayed on the display unit 5230. The electronic appliance can take an image of the user with the sensor unit 5250 and transmit the image of the user. The electronic appliance can acquire a viewing history of the user and provide it to a cloud service. The electronic appliance can acquire recommendation data from a cloud service and display the data on the display unit 5230. A program or a moving image can be displayed on the basis of the recommendation data. As another example, the electronic appliance has a function of changing its display method in accordance with the illuminance of a usage environment. Accordingly, for example, it is possible to obtain a television system which can display an image such that the television system can be suitably used even under strong external light entering the room from the outside in fine weather.

FIG. 13C illustrates an electronic appliance that is capable of receiving an educational material via the Internet and displaying it on the display unit 5230. An example of such an electronic appliance is a tablet computer. The user can input an assignment with the input unit 5240 and send it via the Internet. The user can obtain a corrected assignment or the evaluation from a cloud service and have it displayed on the display unit 5230. The user can select a suitable educational material on the basis of the evaluation and have it displayed.

For example, an image signal can be received from another electronic appliance and displayed on the display unit 5230. When the electronic appliance is placed on a stand or the like, the display unit 5230 can be used as a sub-display. Thus, for example, it is possible to obtain a tablet computer which can display an image such that the tablet computer is favorably used even in an environment under strong external light, e.g., outdoors in fine weather.

FIG. 13D illustrates an electronic appliance including a plurality of display units 5230. An example of such an electronic appliance is a digital camera. For example, the display unit 5230 can display an image that the sensor unit 5250 is capturing. A captured image can be displayed on the sensor unit. A captured image can be decorated using the input unit 5240. A message can be attached to a captured image. A captured image can be transmitted via the Internet. The electronic appliance has a function of changing shooting conditions in accordance with the illuminance of a usage environment. Accordingly, for example, it is possible to obtain a digital camera that can display a subject such that an image is favorably viewed even in an environment under strong external light, e.g., outdoors in fine weather.

FIG. 13E illustrates an electronic appliance in which the electronic appliance of this embodiment is used as a master to control another electronic appliance used as a slave. An example of such an electronic appliance is a portable personal computer. For example, part of image data can be displayed on the display unit 5230 and another part of the image data can be displayed on a display unit of another electronic appliance. Image signals can be supplied. Data written from an input unit of another electronic appliance can be obtained with the communication unit 5290. Thus, a large display region can be utilized in the case of using a portable personal computer, for example.

FIG. 14A illustrates an electronic appliance including the sensing unit 5250 that senses an acceleration or a direction. An example of such an electronic appliance is a goggles-type electronic appliance. The sensor unit 5250 can supply data on the position of the user or the direction in which the user faces. The electronic appliance can generate image data for the right eye and image data for the left eye in accordance with the position of the user or the direction in which the user faces. The display unit 5230 includes a display region for the right eye and a display region for the left eye. Thus, a virtual reality image that gives the user a sense of immersion can be displayed on the goggles-type electronic appliance, for example.

FIG. 14B illustrates an electronic appliance including an imaging device and the sensing unit 5250 that senses an acceleration or a direction. An example of such an electronic appliance is a glasses-type electronic appliance. The sensor unit 5250 can supply data on the position of the user or the direction in which the user faces. The electronic appliance can generate image data in accordance with the position of the user or the direction in which the user faces. Accordingly, the data can be shown together with a real-world scene, for example. Alternatively, an augmented reality image can be displayed on the glasses-type electronic appliance.

Note that this embodiment can be combined with any of the other embodiments in this specification as appropriate.

Embodiment 6

Figure 15A:
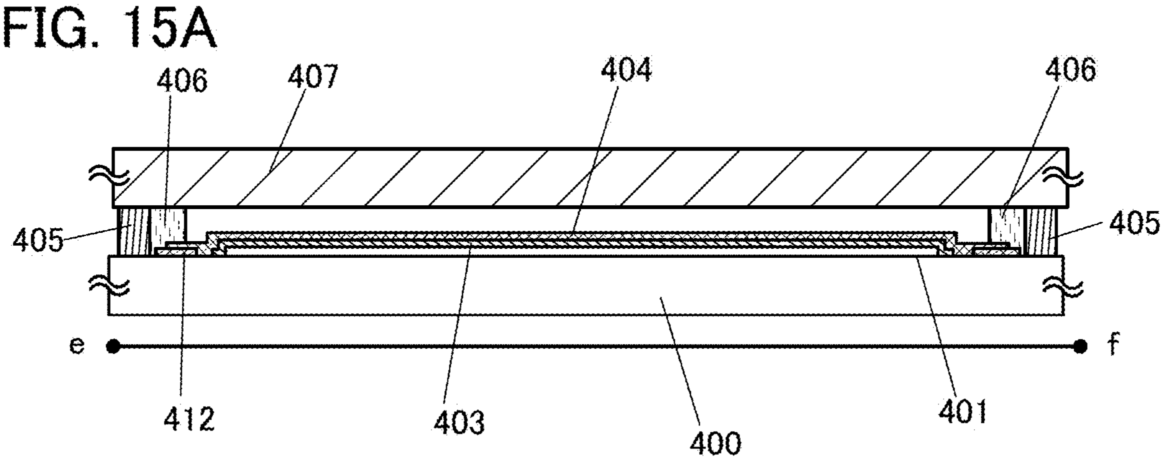
FIGS. 15A and 15B illustrate a lighting device of an embodiment.
Figure 15B:
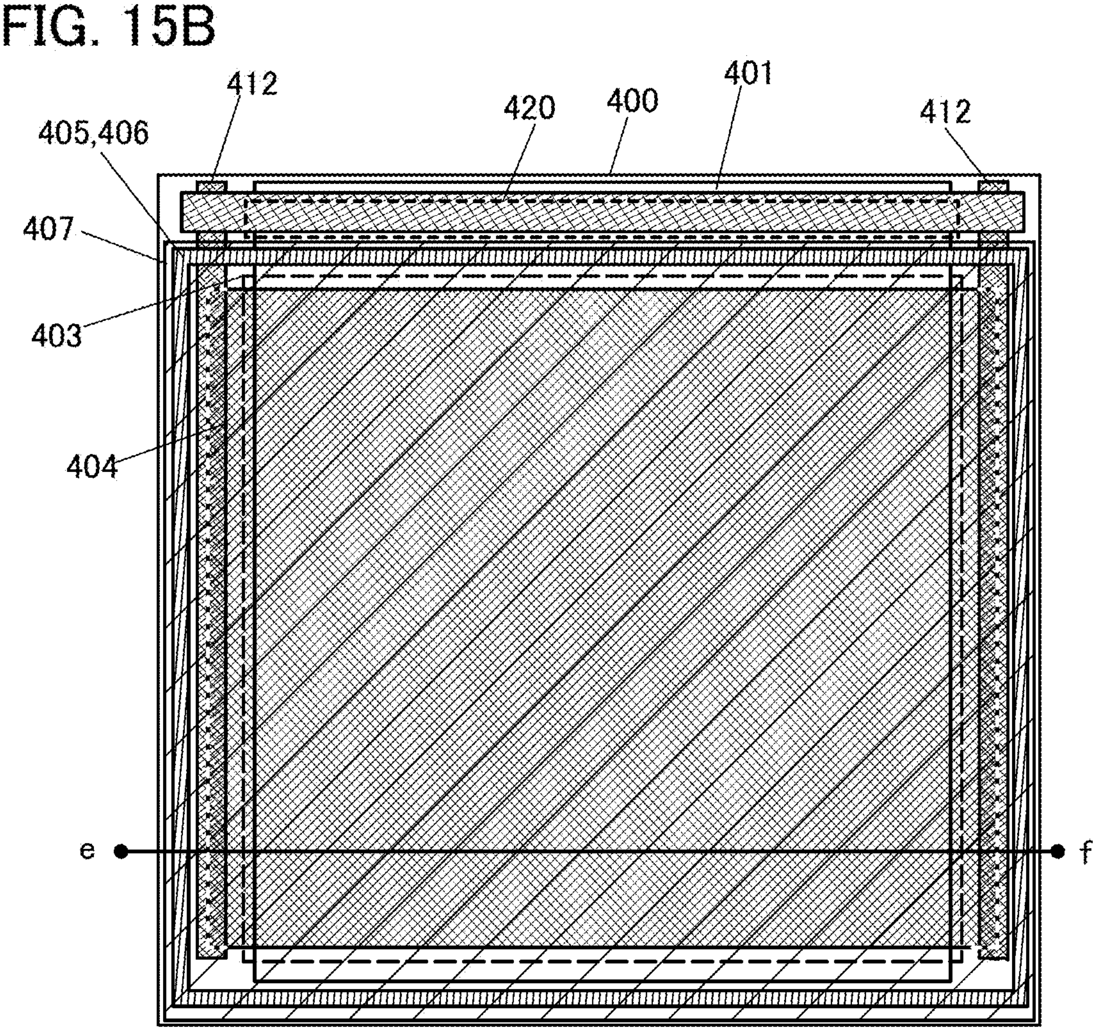

In this embodiment, a structure in which the light-emitting device described in Embodiments 1 and 2 is used in a lighting device will be described with reference to FIGS. 15A and 15B. FIG. 15A shows a cross section taken along the line e-f in a top view of the lighting device in FIG. 15B.

In the lighting device in this embodiment, a first electrode 401 is formed over a substrate 400 that is a support and has a light-transmitting property. The first electrode 401 corresponds to the first electrode 101 in Embodiments 1 and 2. When light is extracted from the first electrode 401 side, the first electrode 401 is formed using a material having a light-transmitting property.

A pad 412 for applying voltage to a second electrode 404 is provided over the substrate 400.

An EL layer 403 is formed over the first electrode 401. The structure of the EL layer 403 corresponds to, for example, the structure of the EL layer 103 in Embodiments 1 and 2. Refer to the corresponding description for these structures.

The second electrode 404 is formed to cover the EL layer 403. The second electrode 404 corresponds to the second electrode 102 in Embodiments 1 and 2. The second electrode 404 is formed using a material having high reflectance when light is extracted from the first electrode 401 side. The second electrode 404 is connected to the pad 412 so that voltage is applied to the second electrode 404.

As described above, the lighting device described in this embodiment includes a light-emitting device including the first electrode 401, the EL layer 403, and the second electrode 404. Since the light-emitting device has high emission efficiency, the lighting device in this embodiment can have low power consumption.

The substrate 400 provided with the light-emitting device having the above structure and a sealing substrate 407 are fixed and sealed with sealing materials 405 and 406, whereby the lighting device is completed. It is possible to use only either the sealing material 405 or the sealing material 406. In addition, the inner sealing material 406 (not illustrated in FIG. 15B) can be mixed with a desiccant that enables moisture to be adsorbed, increasing the reliability.

When parts of the pad 412 and the first electrode 401 are extended to the outside of the sealing materials 405 and 406, the extended parts can serve as external input terminals. An IC chip 420 mounted with a converter or the like may be provided over the external input terminals.

Embodiment 7

Figure 16:
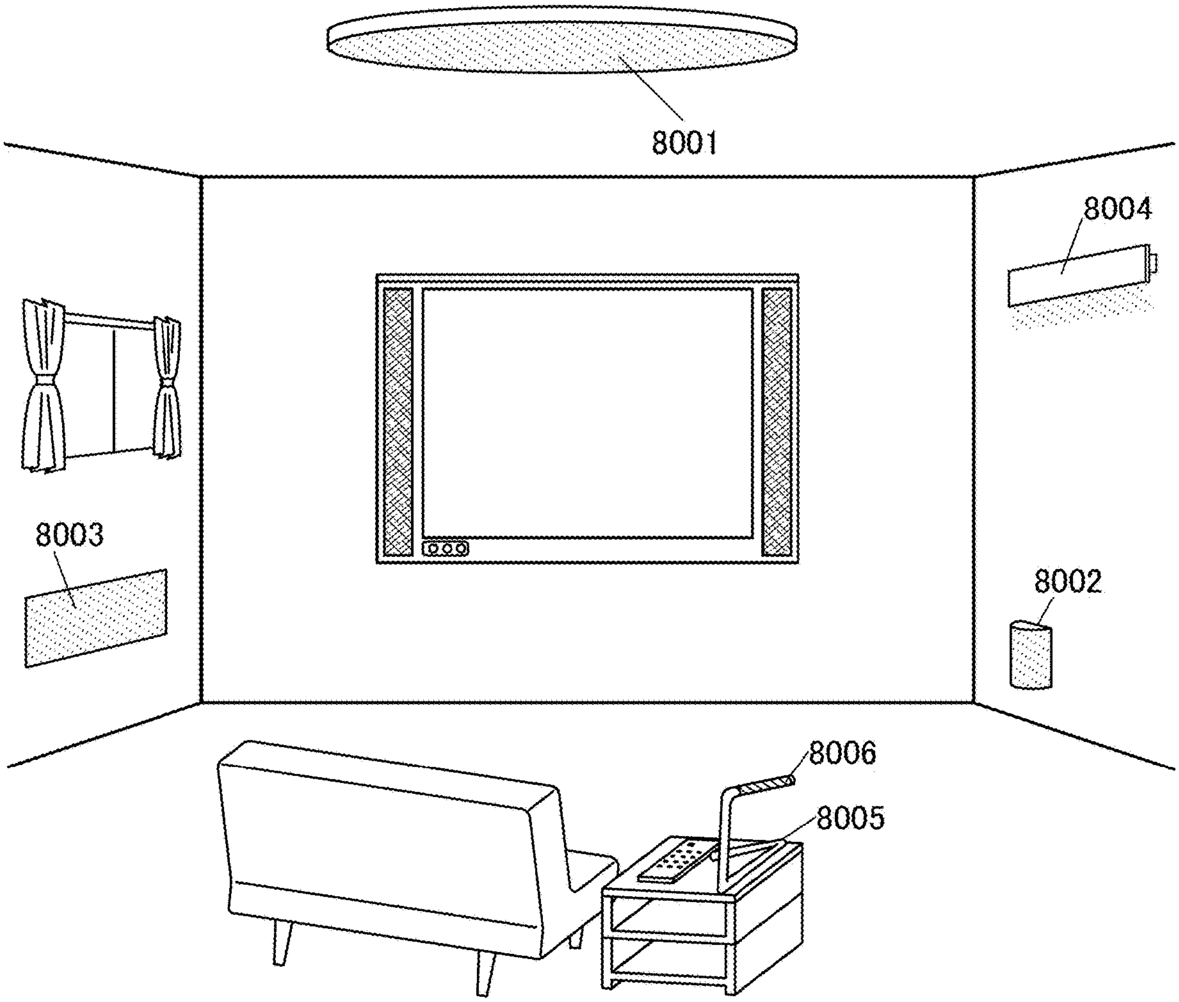
FIG. 16 illustrates lighting devices of an embodiment.

In this embodiment, application examples of lighting devices fabricated using the light-emitting apparatus of one embodiment of the present invention or the light-emitting device, which is part of the light-emitting apparatus, will be described with reference to FIG. 16.

A ceiling light 8001 can be used as an indoor lighting device. Examples of the ceiling light 8001 include a direct-mount light and an embedded light. Such lighting devices are fabricated using the light-emitting apparatus and a housing and a cover in combination. Application to a cord pendant light (light that is suspended from a ceiling by a cord) is also possible.

A foot light 8002 lights a floor so that safety on the floor can be improved. For example, it can be effectively used in a bedroom, on a staircase, and on a passage. In such cases, the size and shape of the foot light can be changed in accordance with the dimensions and structure of a room. The foot light can be a stationary lighting device using the light-emitting apparatus and a support in combination.

A sheet-like lighting 8003 is a thin sheet-like lighting device. The sheet-like lighting, which is attached to a wall when used, is space-saving and thus can be used for a wide variety of uses. Furthermore, the area of the sheet-like lighting can be easily increased. The sheet-like lighting can also be used on a wall or a housing that has a curved surface.

A lighting device 8004 in which the direction of light from a light source is controlled to be only a desired direction can be used.

A desk lamp 8005 includes a light source 8006. As the light source 8006, the light-emitting apparatus of one embodiment of the present invention or the light-emitting device, which is part of the light-emitting apparatus, can be used.

Besides the above examples, when the light-emitting apparatus of one embodiment of the present invention or the light-emitting device, which is part of the light-emitting apparatus, is used as part of furniture in a room, a lighting device that functions as the furniture can be obtained.

As described above, a variety of lighting devices that include the light-emitting apparatus can be obtained. Note that these lighting devices are also embodiments of the present invention.

The structures described in this embodiment can be used in appropriate combination with any of the structures described in the other embodiments.

Embodiment 8

In this embodiment, a light-emitting device and a light-receiving device that can be used in a display device of one embodiment of the present invention are described with reference to FIGS. 17A to 17C.

Figure 17A:
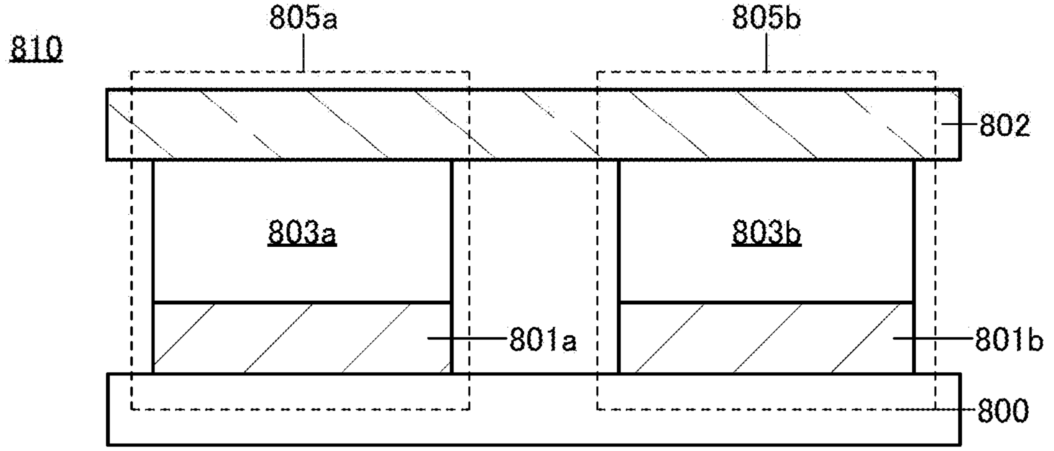
FIGS. 17A to 17C illustrate a light-emitting device and a light-receiving device of an embodiment.

FIG. 17A is a schematic cross-sectional view of a light-emitting device 805*a* and a light-receiving device 805*b* included in a display device 810 of one embodiment of the present invention.

The light-emitting device 805*a* has a function of emitting light (hereinafter, also referred to as a light-emitting function). The light-emitting device 805*a* includes an electrode 801*a*, an EL layer 803*a*, and an electrode 802. The light-emitting device 805*a* is preferably a light-emitting device utilizing organic EL (an organic EL device) described in Embodiment 2. Thus, the EL layer 803*a* interposed between the electrode 801*a* and the electrode 802 at least includes a light-emitting layer. The light-emitting layer includes a light-emitting substance. The EL layer 803*a* emits light when voltage is applied between the electrode 801*a* and the electrode 802. The EL layer 803*a* may include any of a variety of layers such as a hole-injection layer, a hole-transport layer, an electron-transport layer, an electron-injection layer, a carrier-blocking (hole-blocking or electron-blocking) layer, and a charge generation layer, in addition to the light-emitting layer.

The light-receiving device 805*b* has a function of sensing light (hereinafter, also referred to as a light-receiving function). As the light-receiving device 805*b*, a PN photodiode or a PIN photodiode can be used, for example. The light-emitting device 805*b* includes an electrode 801*b*, a light-receiving layer 803*b*, and the electrode 802. Thus, the light-receiving layer 803*b* interposed between the electrode 801*b* and the electrode 802 at least includes an active layer. Note that for the light-receiving layer 803*b*, any of materials that are used for the variety of layers (e.g., the hole-injection layer, the hole-transport layer, the light-emitting layer, the electron-transport layer, the electron-injection layer, the carrier-blocking (hole-blocking or electron-blocking) layer, and the charge generation layer) included in the above-described EL layer 803*a* can be used. The light-receiving device 805*b* functions as a photoelectric conversion device. When light is incident on the light-receiving layer 803*b*, electric charge can be generated and extracted as a current. At this time, voltage may be applied between the electrode 801*b* and the electrode 802. The amount of generated electric charge depends on the amount of the light incident on the light-receiving layer 803*b*.

The light-receiving device 805*b* has a function of sensing visible light. The light-receiving device 805*b* has sensitivity to visible light. The light-receiving device 805*b* further preferably has a function of sensing visible light and infrared light. The light-receiving device 805*b* preferably has sensitivity to visible light and infrared light.

In this specification and the like, a blue (B) wavelength region ranges from 400 nm to less than 490 nm, and blue (B) light has at least one emission spectrum peak in the wavelength region. A green (G) wavelength region ranges from 490 nm to less than 580 nm, and green (G) light has at least one emission spectrum peak in the wavelength region. A red (R) wavelength region ranges from 580 nm to less than 700 nm, and red (R) light has at least one emission spectrum peak in the wavelength region. In this specification and the like, a visible wavelength region ranges from 400 nm to less than 700 nm, and visible light has at least one emission spectrum peak in the wavelength region. An infrared (IR) wavelength region ranges from 700 nm to less than 900 nm, and infrared (IR) light has at least one emission spectrum peak in the wavelength region.

The active layer in the light-receiving device 805*b* includes a semiconductor. Examples of the semiconductor are inorganic semiconductors such as silicon, organic semiconductors such as organic compounds, and the like. As the light-receiving device 805*b*, an organic semiconductor device (or an organic photodiode) including an organic semiconductor in the active layer is preferably used. An organic photodiode, which is easily made thin, lightweight, and large in area and has a high degree of freedom for shape and design, can be used in a variety of display devices. An organic semiconductor is preferably used, in which case the EL layer 803*a* included in the light-emitting device 805*a* and the light-receiving layer 803*b* included in the light-receiving device 805*b* can be formed by the same method (e.g., a vacuum evaporation method) with the same manufacturing apparatus. Note that any of the organic compounds of one embodiment of the present invention can be used for the light-receiving layer 803*b* in the light-receiving device 805*b*.

In the display device of one embodiment of the present invention, an organic EL device and an organic photodiode can be suitably used as the light-emitting device 805*a* and the light-receiving device 805*b*, respectively. The organic EL device and the organic photodiode can be formed over one substrate. Thus, the organic photodiode can be incorporated into the display device including the organic EL device. A display device of one embodiment of the present invention has one or both of an image capturing function and a sensing function in addition to a function of displaying an image.

The electrode 801*a* and the electrode 801*b* are provided on the same plane. In FIG. 17A, the electrodes 801*a* and 801*b* are provided over a substrate 800. The electrodes 801*a* and 801*b* can be formed by processing a conductive film formed over the substrate 800 into island shapes, for example. In other words, the electrodes 801*a* and 801*b* can be formed through the same process.

As the substrate 800, a substrate having heat resistance high enough to withstand the formation of the light-emitting device 805*a* and the light-receiving device 805*b* can be used. When an insulating substrate is used, a glass substrate, a quartz substrate, a sapphire substrate, a ceramic substrate, an organic resin substrate or the like can be used as the substrate 800. Alternatively, a semiconductor substrate can be used. For example, a single crystal semiconductor substrate or a polycrystalline semiconductor substrate of silicon, silicon carbide, or the like; a compound semiconductor substrate of silicon germanium or the like; an SOI substrate; or the like can be used.

As the substrate 800, it is preferable to use the insulating substrate or the semiconductor substrate over which a semiconductor circuit including a semiconductor element such as a transistor is formed, in particular. The semiconductor circuit preferably forms a pixel circuit, a gate line driver circuit (a gate driver), a source line driver circuit (a source driver), or the like. In addition to the above, an arithmetic circuit, a memory circuit, or the like may be formed.

The electrode 802 is formed of a layer shared by the light-emitting device 805*a* and the light-receiving device 805*b*. As the electrode through which light enters or exits, a conductive film that transmits visible light and infrared light is used. As the electrode through which light neither enters nor exits, a conductive film that reflects visible light and infrared light is preferably used.

The electrode 802 in the display device of one embodiment of the present invention functions as one of the electrodes in each of the light-emitting device 805*a* and the light-receiving device 805*b*.

Figure 17B:
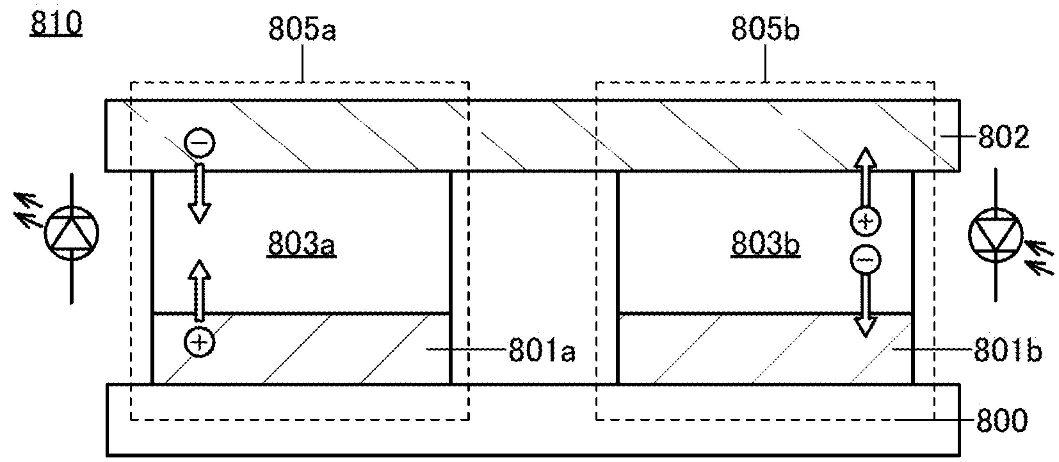

In FIG. 17B, the electrode 801*a* of the light-emitting device 805*a* has a potential higher than the electrode 802. In this case, the electrode 801*a* and the electrode 802 function as an anode and a cathode, respectively, in the light-emitting device 805*a*. The electrode 801*b* of the light-receiving device 805*b* has a potential lower than the electrode 802. For easy understanding of the direction of current flow, FIG. 17B illustrates a circuit symbol of a light-emitting diode on the left in the light-emitting device 805*a* and a circuit symbol of a photodiode on the right in the light-receiving device 805*b*. The flow directions of carriers (electrons and holes) in each device are also schematically indicated by arrows.

In the structure illustrated in FIG. 17B, when a first potential is supplied to the electrode 801*a* through a first wiring, a second potential is supplied to the electrode 802 through a second wiring, and a third potential is supplied to the electrode 801*a* through a third wiring in the light-emitting device 805*a*, the following relationship is satisfied: the first potential>the second potential>the third potential.

Figure 17C:
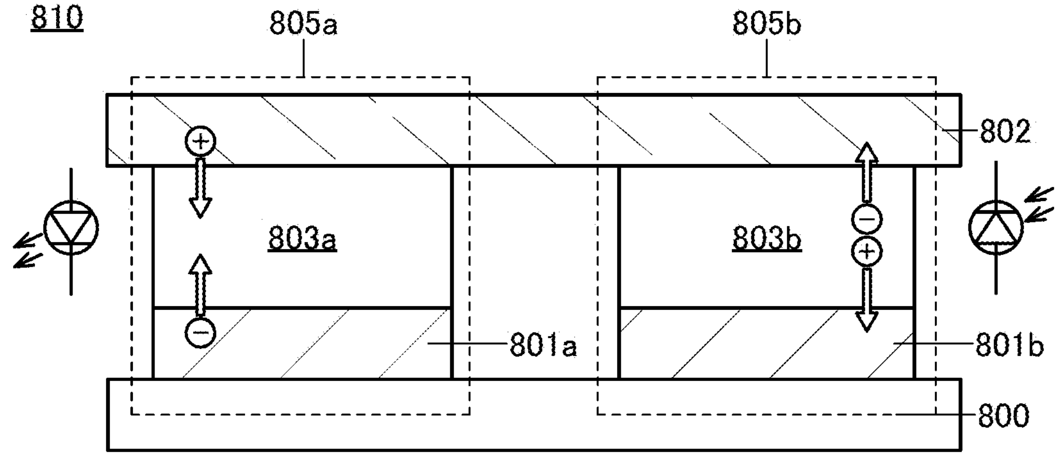
Figure 18A:
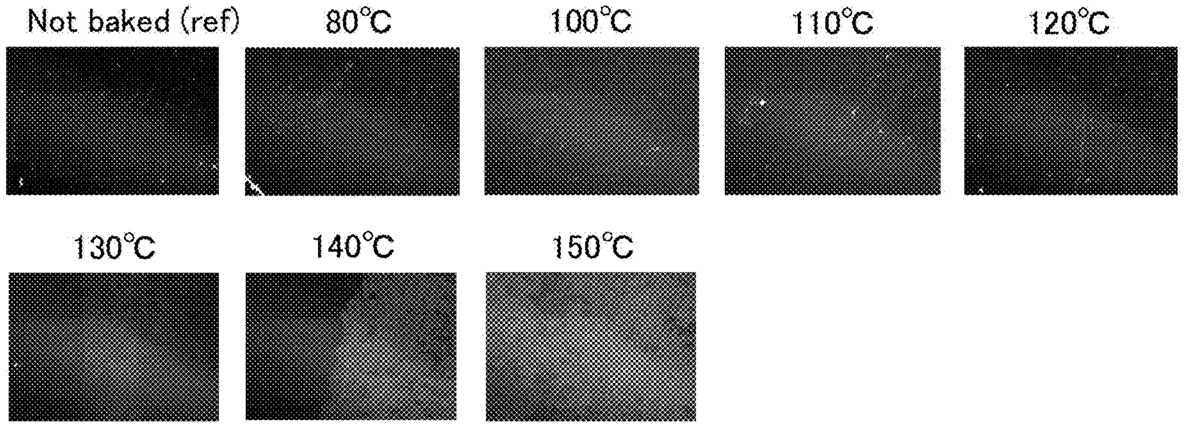
FIGS. 18A to 18C show photographs according to an example.
Figure 18B:
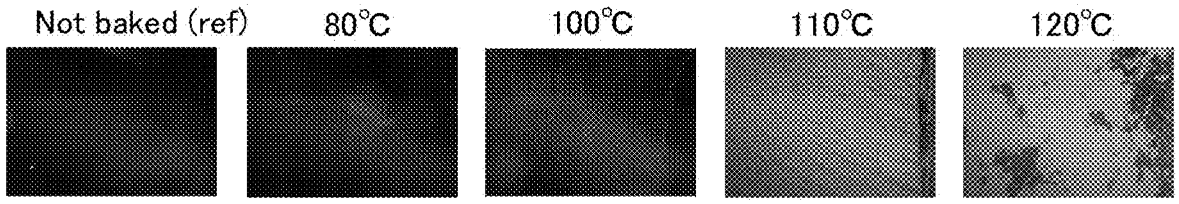
Figure 18C:
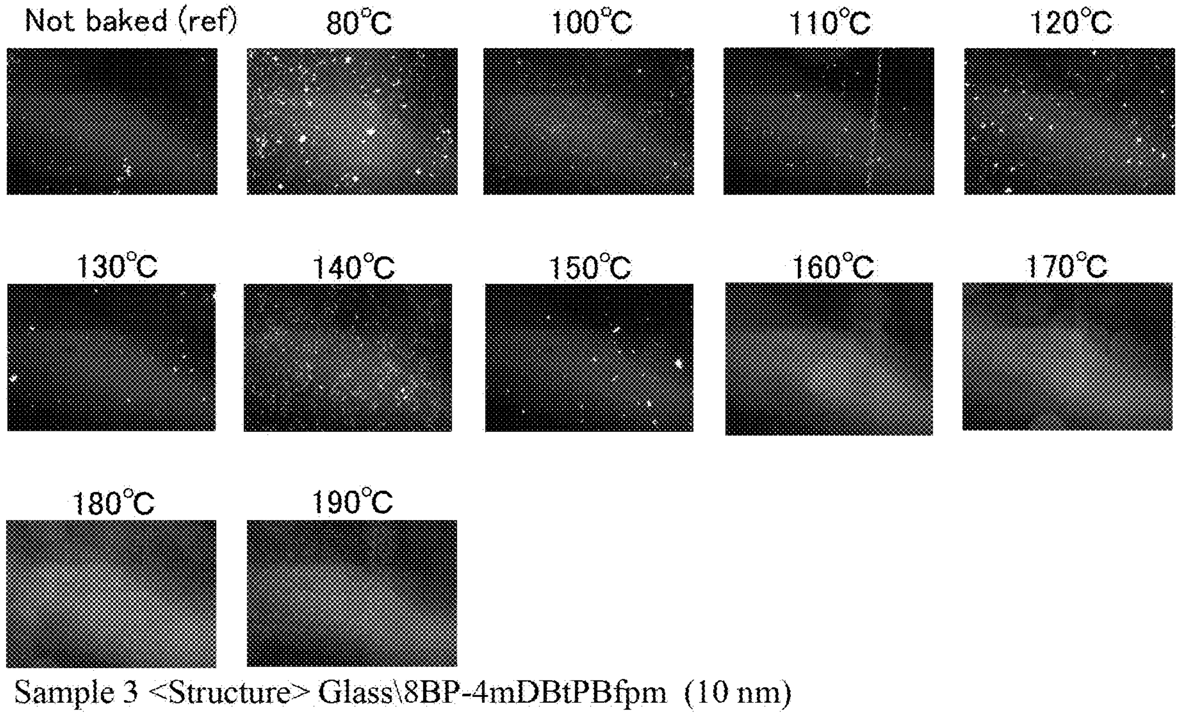
Figure 19A:
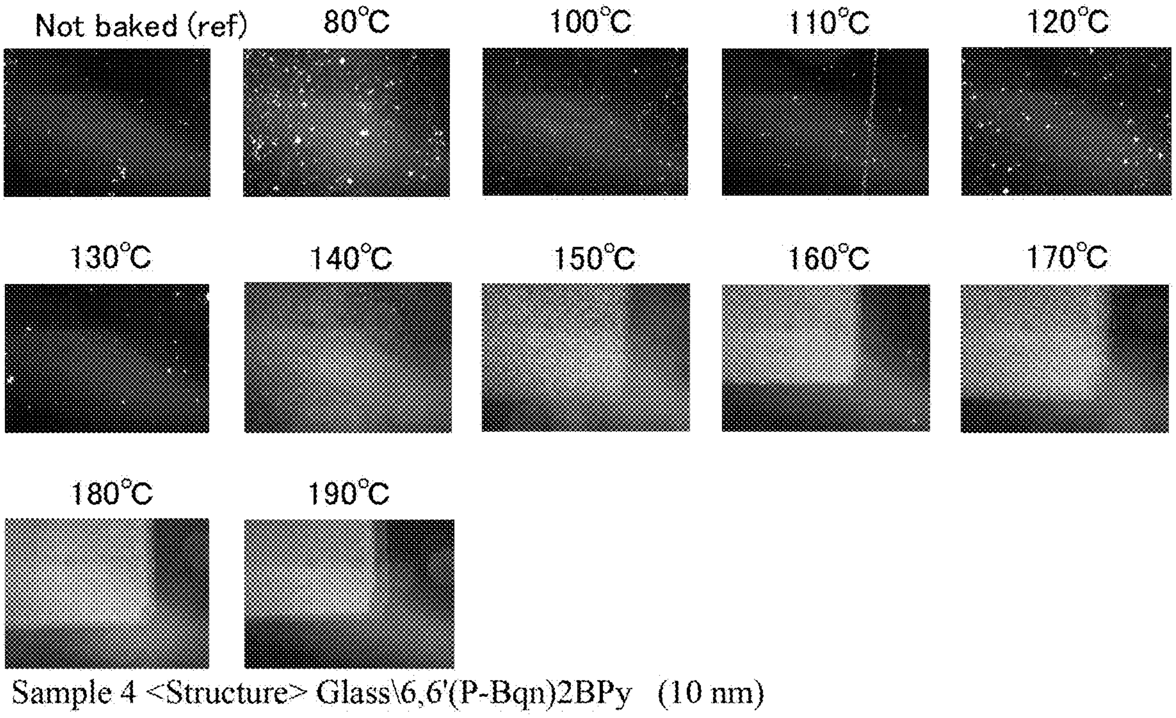
FIGS. 19A and 19B show photographs according to an example.
Figure 19B:
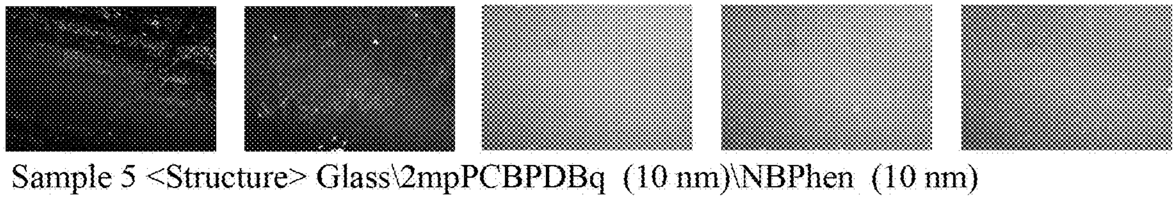
Figure 20A:
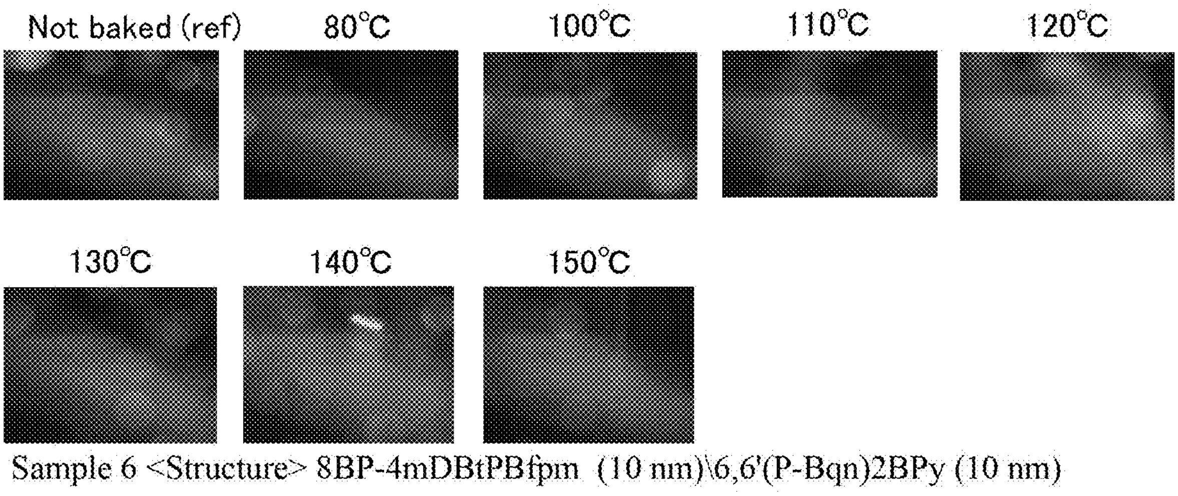
FIGS. 20A and 20B show photographs according to an example.
Figure 20B:
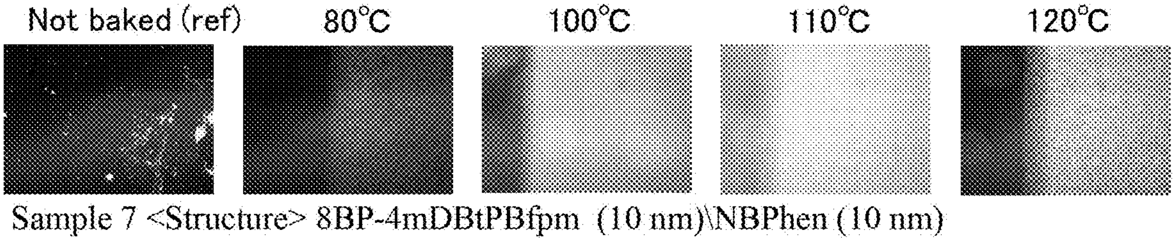

In FIG. 17C, the electrode 801*a* of the light-emitting device 805*a* has a potential lower than the electrode 802. In this case, the electrode 801*a* and the electrode 802 function as a cathode and an anode, respectively, in the light-emitting device 805*a*. The electrode 801*b* of the light-receiving device 805*b* has a potential lower than the electrode 802 and a potential higher than the potential of the electrode 801*a*. For easy understanding of the direction of current flow, FIG. 17C illustrates a circuit symbol of a light-emitting diode on the left in the light-emitting device 805*a* and a circuit symbol of a photodiode on the right in the light-receiving device 805*b*. The flow directions of carriers (electrons and holes) in each device are also schematically indicated by arrows.

In the structure illustrated in FIG. 17C, when a first potential is supplied to the electrode 801*a* through a first wiring, a second potential is supplied to the electrode 802 through a second wiring, and a third potential is supplied to the electrode 801*a* through a third wiring in the light-emitting device 805*a*, the following relationship is satisfied: the second potential>the third potential>the first potential.

The resolution of the light-receiving device 805*b* described in this embodiment can be 100 ppi or higher, preferably 200 ppi or higher, further preferably 300 ppi or higher, still further preferably 400 ppi or higher, and still further preferably 500 ppi or higher, and 2000 ppi or lower, 1000 ppi or lower, or 600 ppi or lower, for example. In particular, when the resolution of the light-receiving device 805*b* is 200 ppi or higher and 600 ppi or lower, preferably 300 ppi or higher and 600 ppi or lower, the display device of one embodiment of the present invention can be suitably applied to image capturing of fingerprints. In fingerprint authentication with the display device of one embodiment of the present invention, the increased resolution of the light-receiving device 805*b* enables, for example, high accuracy extraction of the minutiae of fingerprints; thus, the accuracy of the fingerprint authentication can be increased. The resolution is preferably 500 ppi or higher, in which case the authentication conforms to the standard by the National Institute of Standards and Technology (NIST) or the like. On the assumption that the resolution of the light-receiving device is 500 ppi, the size of each pixel is 50.8 μm, which is adequate for image capturing of a fingerprint ridge distance (typically, from 300 μm to 500 μm, inclusive).

The structures described in this embodiment can be used in appropriate combination with any of the structures described in the other embodiments.

Example 1

In this example, four kinds of materials were used and one or two of the materials was/were deposited over a glass substrate to form thin films, whereby samples with different film structures (e.g., a single-layer film, a stacked-layer film, and a mixed film) were formed. The samples were subjected to heat resistance test. Thermophysical properties of the materials used in this example are listed in Table 1, and the structural formulae thereof are shown below. For the thermophysical properties, differential scanning calorimetry (DSC measurement) was performed by Pyris1DSC manufactured by PerkinElmer, Inc. Note that in this specification, the result (Tpc) in Table 1 is referred to as a crystallization temperature of a powered state.

TABLE 1

| Material | Tg (° C.) | Tc (° C.) | Tm (° C.) |
|---|---|---|---|
| NBPhen | 165 | 323 (in decreasing temperature) | 354 |
| 2mpPCBPDBq | 125 | N.D. | N.D. |
| 8BP-4mDBtPBfpm | 111 | 163 | 266 |
| 6,6'(P-Bqn)$_2$BPy | N.D. | 198 | 356 |

*Tg: glass transition temperature (° C.),

Tpc: crystallization temperature (° C.) (powder state),

Tm: melting point (° C.), N.D.: undetectable

[Chemical Formula 5]

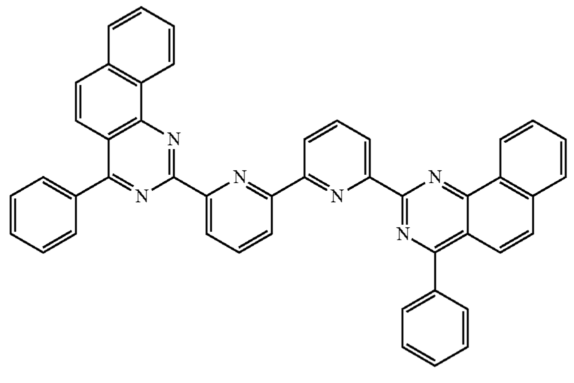

6,6'(P-Bqn)$_2$BPy

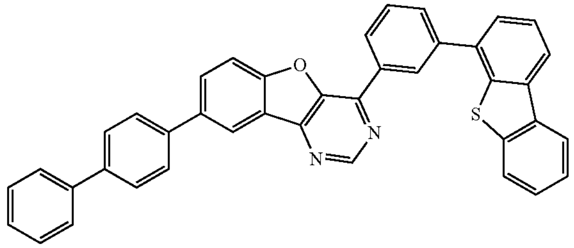

8BP-4mDBtPBfpm

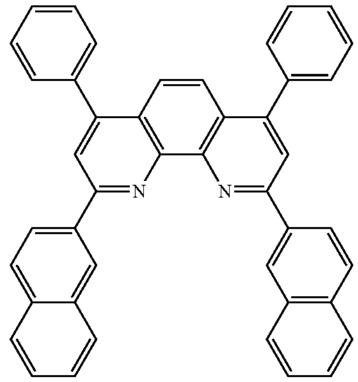

NBPhen

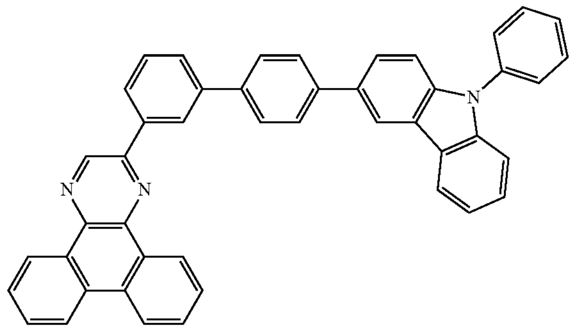

2mpPCBPDBq

Samples 1 to 7 were formed as described below.

First, a sample layer was formed over a glass substrate with a vacuum oven, and cut into square shapes of 2 cm×2 cm to form the samples. Next, the samples were introduced into a bell jar type vacuum oven (BV-001, SHIBATA SCIENTIFIC TECHNOLOGY LTD.), and the pressure was reduced to approximately 10 hPa, followed by one-hour baking at temperatures in the range of 80° C. to 190° C. After one hour passed, the substrate was cooled down to 40° C. and placed in the air, then the samples were taken out with tweezers.

The sample layer of Sample 1 was a single-layer film of one kind of heteroaromatic compound, which was formed by evaporation of 2,9-di(2-naphthyl)-4,7-diphenyl-1,10-phenanthroline (abbreviation: NBPhen) to a thickness of 10 nm over the glass substrate.

The sample layer of Sample 2 was a single-layer film of one kind of heteroaromatic compound, which was formed by evaporation of 2-[4'-(9-phenyl-9H-carbazol-3-yl)-3,1'-biphenyl-1-yl]dibenzo[f,h]quinoxaline (abbreviation: 2mpPCBPDBq) to a thickness of 10 nm over the glass substrate.

The sample layer of Sample 3 was a single-layer film of one kind of heteroaromatic compound, which was formed by evaporation of 8-(1,1'-biphenyl-4-yl)-4-[3-(dibenzothiophen-4-yl)phenyl]-[1]benzofuro[3,2-d]pyrimidine (abbreviation: 8BP-4mDBtPBfpm) to a thickness of 10 nm over the glass substrate.

The sample layer of Sample 4 was a single-layer film of one kind of heteroaromatic compound, which was formed by evaporation of 2,2'-(2,2'-bipyridine-6,6'-diyl)bis(4-phenylbenzo[h]quinazoline) (abbreviation: 6,6'(P-Bqn)2BPy) to a thickness of 10 nm over the glass substrate.

The sample layer of Sample 5 was a stacked-layer film of a plurality of heteroaromatic compounds, which was formed by evaporation of 2mpPCBPDBq to a thickness of 10 nm and then evaporation of NBPhen to a thickness of 10 nm over the glass substrate.

The sample layer of Sample 6 was a stacked-layer film of a plurality of heteroaromatic compounds, which was formed by evaporation of 8BP-4mDBtPBfpm to a thickness of 10 nm and then evaporation of 6,6'(P-Bqn)2BPy to a thickness of 10 nm over the glass substrate.

The sample layer of Sample 7 was a stacked-layer film of a plurality of heteroaromatic compounds, which was formed by evaporation of 8BP-4mDBtPBfpm to a thickness of 10 nm and then evaporation of NBPhen to a thickness of 10 nm over the glass substrate.

The samples formed by such a method were observed visually and with an optical microscope (MX61L semiconductor/FPD inspection microscope, Olympus Corporation).

FIGS. 18A to 18C, FIGS. 19A and 19B, and FIGS. 20A and 20B show photographs of the samples formed in this example (dark field observation at a magnification of 100 times).

The structures of the samples and the results of the crystallization based on FIG. 18A to FIG. 20B are shown in Table 2. In Table 2, the circle mark represents no crystal generation (not crystallized), the triangle mark represents slight crystal generation (slightly crystallized), and the cross mark represents crystal generation (crystallized). Specifically, the triangle mark is assigned to the result where a white line is only seen on the edge portion of the thin film and the edge portion has a width of approximately 20 μm. When such an edge portion has a width greater than approximately 20 μm, the cross mark is assigned to the result.

TABLE 2

| Sample NO. | Structure | rt | 80° C. | 100° C. | 110° C. | 120° C. | 130° C. | 140° C. | 150° C. | 160° C. | 170° C. | 180° C. | 190° C. |
|---|---|---|---|---|---|---|---|---|---|---|---|---|---|
| 1 | NBPhen (10 nm) | o | o | o | o | o | o | Δ | Δ | — | — | — | — |
| 2 | 2mpPCBPDBq (10 nm) | o | o | o | Δ or x | Δ or x | — | — | — | — | — | — | — |
| 3 | 8BP-4mDBtPBfpm (10 nm) | o | o | o | o | o | o | o | o | o | x | x | x |
| 4 | 6,6'(P-Bqn)$_2$BPy (10 nm) | o | o | o | o | o | o | x | x | x | x | x | x |
| 5 | 2mpPCBPDBq (10 nm)\ NBPhen (10 nm) | o | o | x | x | x | — | — | — | — | — | — | — |
| 6 | 8BP-4mDBtPBfpm(10 nm)\6,6'(P-Bqn)$_2$BPy (10 nm) | o | o | o | o | o | o | Δ | x | — | — | — | — |
| 7 | 8BP-4mDBtPBfpm(10 nm)\ NBPhen (10 nm) | o | Δ | x | x | x | — | — | — | — | — | — | — |

*rt: room temperature
o: not crystallized,
Δ: slightly crystallized,
x: crystallized (turbid),
—: not measured As shown with the above results, Sample 1 (NBPhen), the single film of one kind of heteroaromatic compound is formed as a thin film that is not crystallized up to high temperature (crystallized at around 140° C. or 150° C.) and has relatively high heat resistance. However, Sample 5 (2mpPCBPDBq\NBPhen), in which a material of Sample 2 (2mpPCBPDBq) having not high heat resistance and the material of Sample 1 (NBPhen) are stacked, has significantly low heat resistance. In addition, Sample 7 (8BP-4mDBtPBfpm\NBPhen), in which a material of Sample 3 (8BP-4mDBtPBfpm) and the material of Sample 1 (NBPhen) having sufficient heat resistance are stacked, also has significantly low heat resistance.

As shown with the above results, Sample 6 (8BP-4mDBtPBfpm\6,6'(P-Bqn)2BPy), the stacked-layer film of the material of Sample 3 (8BP-4mDBtPBfpm) having relatively high heat resistance and a material of Sample 4 (6,6'(P-Bqn)2BPy) having high heat resistance, has high heat resistance.

According to the above results, the difference between the crystallization temperature (Tpc) of the powder state and the crystallization temperature (Ttc) of the thin film state was substantially 0° C. in 8BP-4mDBtPBfpm of Sample 3, approximately 170° C. in NBPhen of Sample 1, approximately 20° C. in 2mpPCBPDBq of Sample 2, and approximately 50° C. in 6,6'(P-Bqn)2BPy of Sample 4. As long as the material that has the smaller difference between the crystallization temperature (Tpc) of the powder state and the crystallization temperature (Ttc) of the thin film state (8BP-4mDBtPBfpm used in Sample 3 in the case of this example) is formed first, a stacked-layer film as well as a single film can be a film (stacked-layer film) insusceptible to heat.

In other words, a material that has a small difference between the crystallization temperature (Tpc) of the powder state and the crystallization temperature (Ttc) of the thin film state (specifically, the difference is preferably less than or equal to 20° C.) is less affected by heat in the thin film state, and accordingly, it can be said that the thermally stable film surface can be maintained.

Table 3 lists specific physical properties of Samples 5, 6, and 7 in Table 2.

TABLE 3

| | First layer | Second layer |
|---|---|---|
| Sample 5 | 2mpPCBPDBq<br>(Tpc: N.D., Note: Tg: 125° C.<br>Ttc: 100-110° C.)<br>$\mid Tpc - Ttc \mid \approx 20°$ C. | NBPhen<br>(Tpc: 323° C. (in decreasing temperature)/<br>Ttc: 130-140° C.)<br>$\mid Tpc - Ttc \mid \approx 170°$ C. |
| Sample 6 | 8BP-4mDBtPBfpm<br>(Tpc: 163° C./Ttc: 160-170° C.)<br>$\mid Tpc - Ttc \mid \approx 0°$ C. | 6.6'(P-Bqn)2BPy<br>(Tpc: 198° C./Ttc: 130-140° C.)<br>$\mid Tpc - Ttc \mid \approx 50°$ C. |
| Sample 7 | 8BP-4mDBtPBfpm<br>(Tpc: 163° C./Ttc: 160-170° C.)<br>$\mid Tpc - Ttc \mid \approx 0°$ C. | NBPhen<br>(Tpc: 323° C. (in decreasing temperature)/<br>Ttc: 130-140° C.)<br>$\mid Tpc - Ttc \mid \approx 170°$ C. |

*Tg: glass transition temperature (° C.), Ttc: crystallization temperature (° C.) of thin film state, Tpc: crystallization temperature (° C.) of powder state From the results in Table 2, Sample 6 is the most suitable for a device formed in the process including a thermal step, among the samples in Table 3. Specifically, when compared with Samples 5 and 7, Sample 6 is preferably formed in such a manner that the first layer of the stacked-layer film is formed using a material having a difference less than or equal to 20° C. between the crystallization temperature (Tpc) of the powder state and the crystallization temperature (Ttc) of the thin film state ($|Tpc-Ttc|$) and the second layer of the stacked-layer film is formed using a material having a $|Tpc-Ttc|$ of 100° C. or less, preferably 50° C. or less. When the first layer and the second layer are used for the electron-transport layer of the light-emitting device, the first layer is formed in contact with the light-emitting layer and the second layer is formed in contact with the first layer.

With the use of such a material that can maintain a thermally stable film surface, a light-emitting device (preferably, the EL layer, further preferably the light-emitting layer, the electron-transport layer, or the electron-injection layer), a light-emitting device or an organic semiconductor device having high heat resistance and device characteristics that are hardly affected by thermal treatment in the fabrication process can be provided.

Example 2

According to the results in Example 1, heat resistance is found to be improved with stacked layers of a first heteroaromatic compound having a difference less than or equal to 20° C. between the crystallization temperature (Tpc) of the powder state and the crystallization temperature (Ttc) of the thin film state and a second heteroaromatic compound having a difference less than or equal to 100° C. between the crystallization temperature (Tpc) of the powder state and the crystallization temperature (Ttc) of the thin film state. This example shows results of fabrication of light-emitting devices including these materials in the electron-transport layer and verification of the relationship between heat resistance and device characteristics.

In the structure of the light-emitting devices fabricated in this example, the electron-transport layer has a stacked-layer structure. The first electron-transport layer in contact with the light-emitting layer includes the first heteroaromatic compound having a difference less than or equal to 20° C. between the crystallization temperature (Tpc) of the powder state and the crystallization temperature (Ttc) of the thin film state. The second electron-transport layer in contact with the first electron-transport layer includes the second heteroaromatic compound having a difference less than or equal to 100° C. between the crystallization temperature (Tpc) of the powder state and the crystallization temperature (Ttc) of the thin film state.

Specifically, Light-emitting device 1 having the above structure and Comparative light-emitting device 3 not having the above structure were fabricated, and the characteristics of the light-emitting devices were compared. The element structures and their characteristics are described below. Light-emitting device 1 used in this example, whose device characteristics (voltage, current, luminance, chromaticity, and an EL spectrum) have been measured, was baked over a hot plate set at a temperature of 120° C. for one hour; the resulting element was referred to as Light-emitting device 2. In a similar manner, Comparative light-emitting device 3, whose device characteristics (voltage, current, luminance, chromaticity, and an EL spectrum) have been measured, was baked over a hot plate set at a temperature of 120° C. for one hour; the resulting element was referred to as Comparative light-emitting device 4. Specific structures of Light-emitting devices 1 and 2 and Comparative light-emitting devices 3 and 4 are shown in Table 4. The chemical formulae of materials used in this example are shown below.

[Chemical Formula 6]

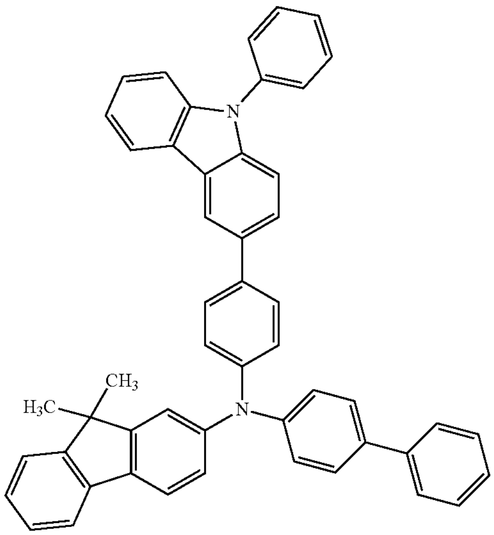

PCBBiF

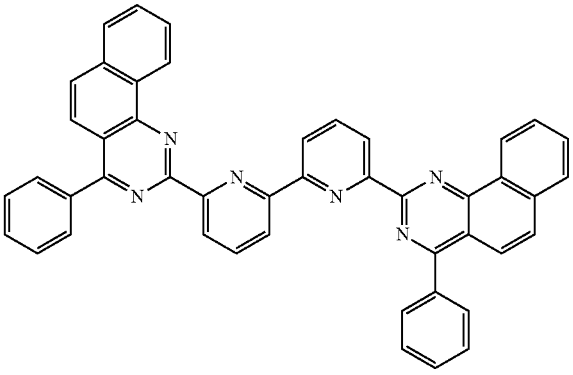

6,6'(P-Bqn)$_2$BPy

TABLE 4

| | First electrode | Hole-injection layer | Hole-transport layer | Light-emitting layer | Electron-transport layer | | Electron-injection layer | Second electrode | Cap layer |
|---|---|---|---|---|---|---|---|---|---|
| Light-emitting device 1 | Ag\ITSO (10 nm) | PCBBiF:OCHD-003 (1:0.03 10 nm) | PCBBiF (135 nm) | * | 8BP-4mDBtPBfpm (20 nm) | 6,6'(P-Bqn)$_2$BPy (10 nm) | LiF (1 nm) | Ag:Mg (1:0.1 15 nm) | DBT3P-II (80 nm) |
| Light-emitting device 2** | | | | | | | | | |
| Comparative light-emitting device 3 | | | | | | NBphen (10 nm) | | | |
| Comparative light-emitting device 4** | | | | | | | | | |

*8BP-4mDBtPBfpm:βNCCP:[Ir(ppy)2(mbfpypy-d3)] (0.6:0.4:0.05, 55 nm)

**subjected to thermal treatment at 120° C. for one hour after formed

-continued

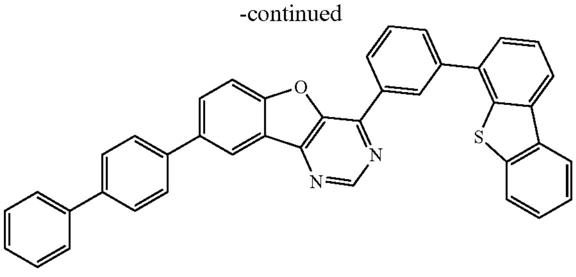

8BP-4mDBtPBfpm

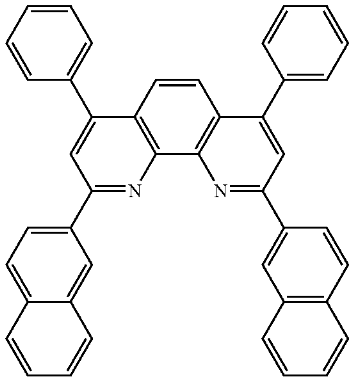

NBPhen

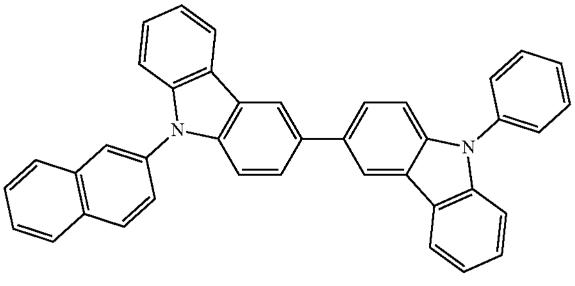

βNCCP

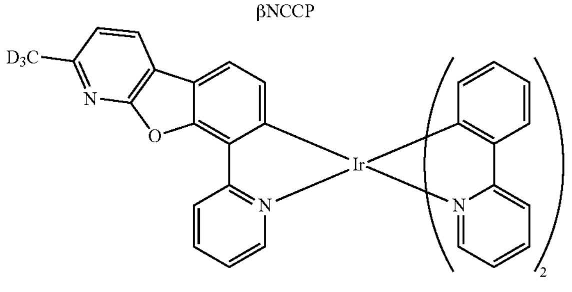

$[Ir(ppy)_2(mbfpypy\text{-}d3)]$

<<Fabrication of Light-Emitting Devices>>

Figure 21:
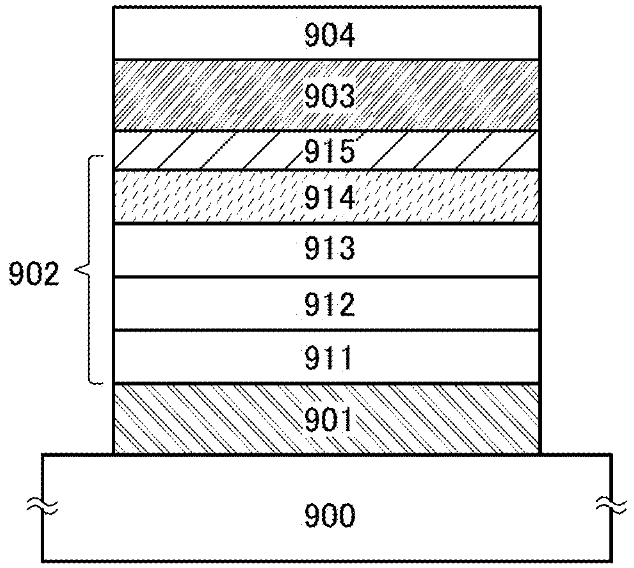
FIG. 21 illustrates a structure of a light-emitting device of an example.

In the light-emitting devices described in this example, as illustrated in FIG. 21, a hole-injection layer 911, a hole-transport layer 912, a light-emitting layer 913, an electron-transport layer 914 (a first electron-transport layer 914-1 and a second electron-transport layer 914-2), and an electron-injection layer 915 are stacked in this order over a first electrode 901 formed over a substrate 900, and a second electrode 903 is stacked over the electron-injection layer 915. Over the second electrode 903, a cap layer 904 is stacked.

First, the first electrode 901 was formed over the substrate 900. The electrode area was set to 4 $mm^2$ (2 mm×2 mm). A glass substrate was used as the substrate 900. The first electrode 901 was formed in such a manner that 100-nm-thick silver (Ag) and 10-nm-thick indium tin oxide containing silicon oxide (ITSO) were subsequently deposited by a sputtering method and stacked.

For pretreatment, a surface of the substrate was washed with water, baking was performed at 200° C. for one hour, and then UV ozone treatment was performed for 370 seconds. After that, the substrate was transferred into a vacuum evaporation apparatus where the pressure was reduced to approximately $1\times10^{-4}$ Pa, and was subjected to vacuum baking at 170° C. for 60 minutes in a heating chamber of the vacuum evaporation apparatus, and then the substrate was cooled down for approximately 30 minutes.

Next, the hole-injection layer 911 was formed over the first electrode 901. The hole-injection layer 911 was formed in such a manner that the pressure in the vacuum evaporation apparatus was reduced to $1\times10^{-4}$ Pa, and then N-(1,1'-biphenyl-4-yl)-N-[4-(9-phenyl-9H-carbazol-3-yl)phenyl]-9,9-dimethyl-9H-fluoren-2-amine (abbreviation: PCBBiF) represented by Structural Formula (i) and an electron acceptor material (OCHD-003) that contains fluorine and has a molecular weight of 672 were deposited by co-evaporation to a thickness of 10 nm in a weight ratio of PCBBiF:OCHD-003=1:0.03.

Then, the hole-transport layer 912 was formed over the hole-injection layer 911. The hole-transport layer 912 was formed to a thickness of 135 nm by evaporation of PCBBiF.

Next, the light-emitting layer 913 was formed over the hole-transport layer 912.

The light-emitting layer 913 was formed to a thickness of 55 nm by co-evaporation of 8-(1,1'-biphenyl-4-yl)-4-[3-(dibenzothiophen-4-yl)phenyl]-[1]benzofuro[3,2-d]pyrimidine (abbreviation: 8BP-4mDBtPBfpm), 9-(2-naphthyl)-9'-phenyl-9H,9'H-3,3'-bicarbazole (abbreviation: βNCCP), and [2-d3-methyl-(2-pyridinyl-κN)benzofuro[2,3-b]pyridine-κC]bis[2-(2-pyridinyl-κN)phenyl-κC]iridium(III) (abbreviation: $[Ir(ppy)_2(mbfpypy\text{-}d_3)]$) such that the weight ratio of 8BP-4mDBtPBfpm to βNCCP and $[Ir(ppy)_2(mbfpypy\text{-}d_3)]$ was 0.6:0.4:0.05.

Next, the electron-transport layer 914 was formed over the light-emitting layer 913. Note that in this example, the electron-transport layer 914 has a stacked-layer structure of the first electron-transport layer 914-1 and the second electron-transport layer 914-2.

In Light-emitting devices 1 and 2, the first electron-transport layer 914-1 was formed to a thickness of 20 nm by evaporation of 8BP-4mDBtPBfpm. Then, the second electron-transport layer 914-2 was formed to a thickness of 10 nm by evaporation of 2,2'-(2,2'-bipyridine-6,6'-diyl)bis(4-phenylbenzo[h]quinazoline) (abbreviation: 6,6'(P-Bqn)2BPy). Note that 8BP-4mDBtPBfpm used for the first electron-transport layer 914-1 in Light-emitting devices 1 and 2 has a difference less than or equal to 20° C. between the crystallization temperature (Tpc) of the powder state and the crystallization temperature (Ttc) of the thin film state. In addition, 6,6'(P-Bqn)2BPy used for the second electron-transport layer 914-2 in Light-emitting devices 1 and 2 has a difference less than or equal to 100° C. between the crystallization temperature (Tpc) of the powder state and the crystallization temperature (Ttc) of the thin film state.

In Comparative light-emitting devices 3 and 4, the first electron-transport layer 914-1 was formed to a thickness of 20 nm by evaporation of 8BP-4mDBtPBfpm. Then, the second electron-transport layer 914-2 was formed using 2,9-di(2-naphthyl)-4,7-diphenyl-1,10-phenanthroline (abbreviation: NBPhen) to a thickness of 10 nm. Note that 8BP-4mDBtPBfpm used for the first electron-transport layer 914-1 in Comparative light-emitting devices 3 and 4 has a difference less than or equal to 20° C. between the crystallization temperature (Tpc) of the powder state and the crystallization temperature (Ttc) of the thin film state. In addition, NBphen used for the second electron-transport layer 914-2 in Comparative light-emitting devices 3 and 4 has a difference of substantially 170° C. between the crystallization temperature (Tpc) of the powder state and the crystallization temperature (Ttc) of the thin film state.

The electron-injection layer 915 was formed over the electron-transport layer 914. The electron-injection layer 915 was formed to a thickness of 1 nm by evaporation of lithium fluoride (LiF).

After that, the second electrode 903 was formed over the electron-injection layer 915. The second electrode 903 was formed to a thickness of 15 nm by co-evaporation of Ag and Mg n a weight ratio of Ag:Mg=1:0.1. In this example, the second electrode 903 functions as a cathode.

Next, the cap layer 904 was formed over the second electrode 903. The cap layer 904 was formed to a thickness of 80 nm by evaporation of 4,4',4"-(benzene-1,3,5-triyl)tri(dibenzothiophene) (abbreviation: DBT3P-II).

Through the above steps, Light-emitting devices 1 and 2 and Comparative light-emitting devices 3 and 4 were fabricated. Note that the hole-injection layer 911, the hole-transport layer 912, the light-emitting layer 913, the electron-transport layer 914, and the electron-injection layer 915 described above are functional layers forming the EL layer in one embodiment of the present invention. Furthermore, in all the evaporation steps in the above fabrication method, evaporation was performed by a resistance-heating method.

The fabricated light-emitting devices were each sealed in a glove box with a nitrogen atmosphere so as not to be exposed to the air (specifically, a sealant was applied to surround each element, and at the time of sealing, UV treatment was performed and then heat treatment was performed at 80° C. for one hour).

As described above, Light-emitting device 2 and Comparative light-emitting device 4 are devices that have been subjected to one-hour heat treatment over a hot plate set at a temperature of 120° C. after the device characteristics of Light-emitting device 1 and Comparative light-emitting device 3 were measured.

Figure 22:
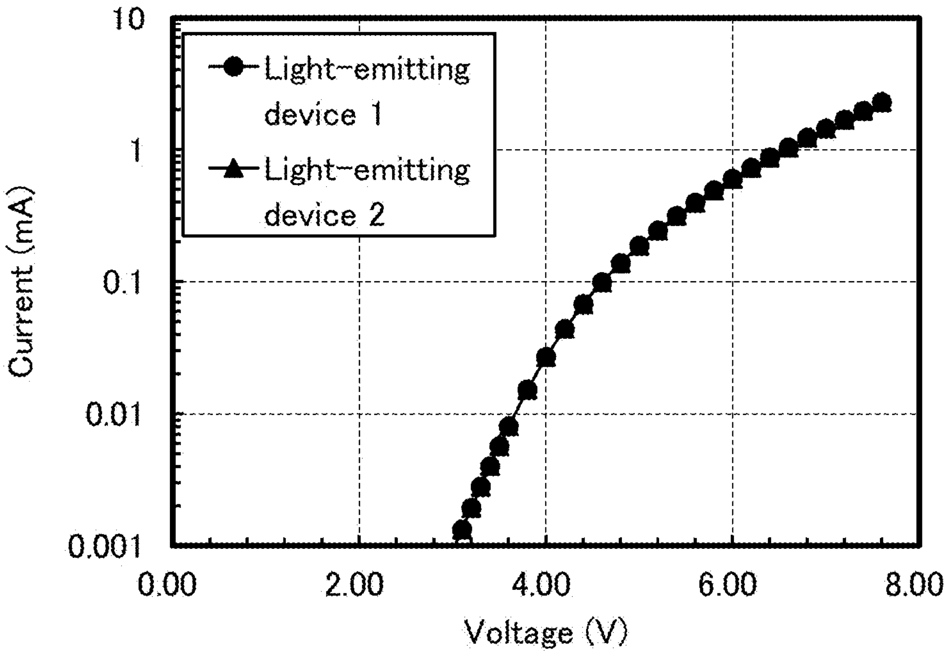
FIG. 22 shows current-voltage characteristics of Light-emitting device 1 and Light-emitting device 2.
Figure 23:
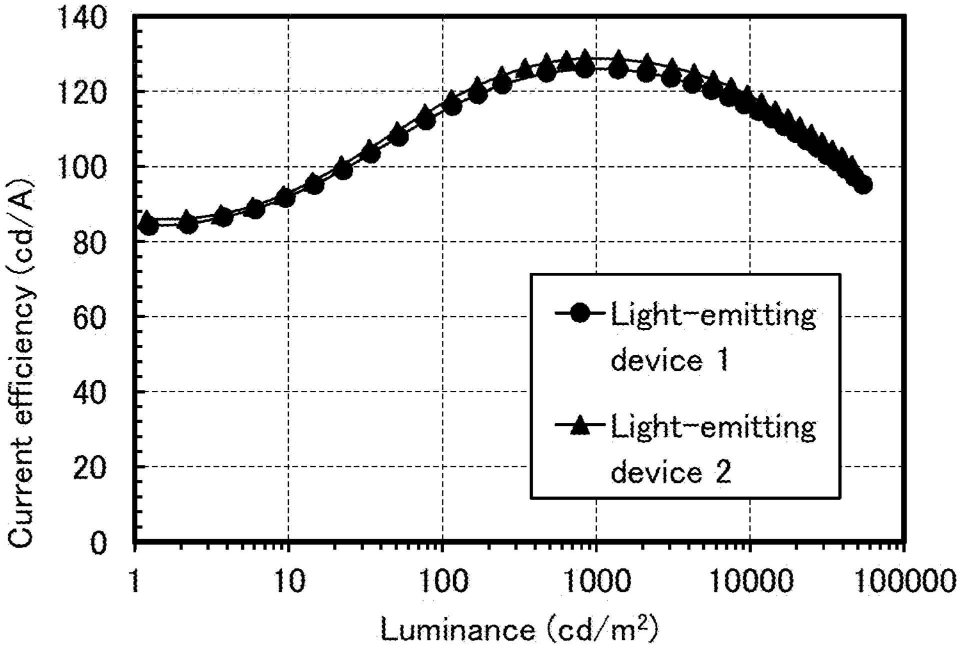
FIG. 23 shows current efficiency-luminance characteristics of Light-emitting device 1 and Light-emitting device 2.
Figure 24:
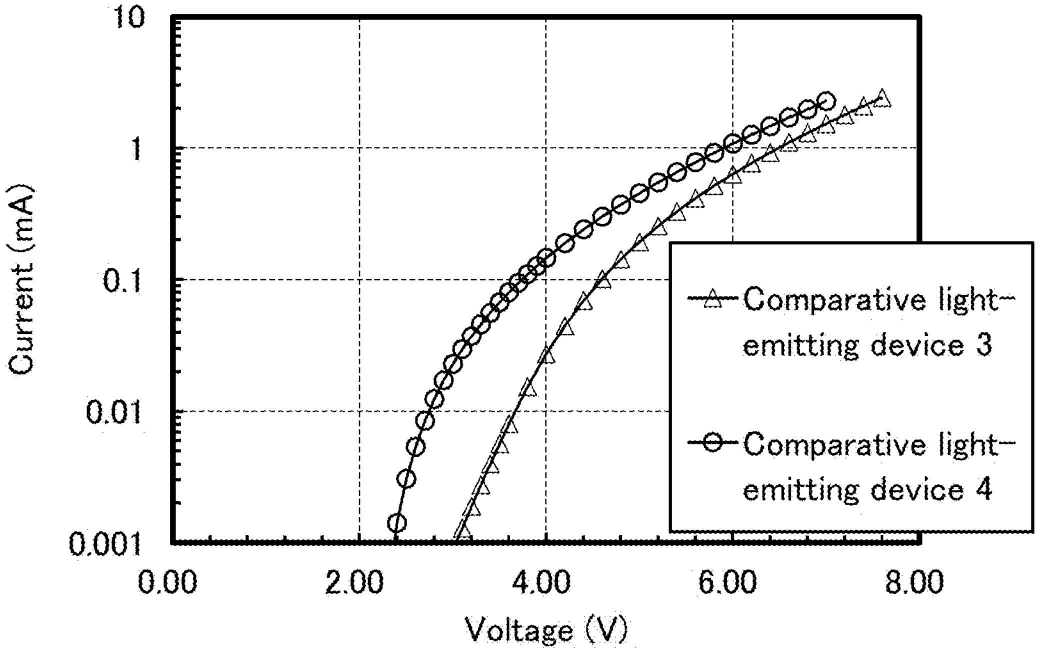
FIG. 24 shows current-voltage characteristics of Comparative light-emitting device 3 and Comparative light-emitting device 4.
Figure 25:
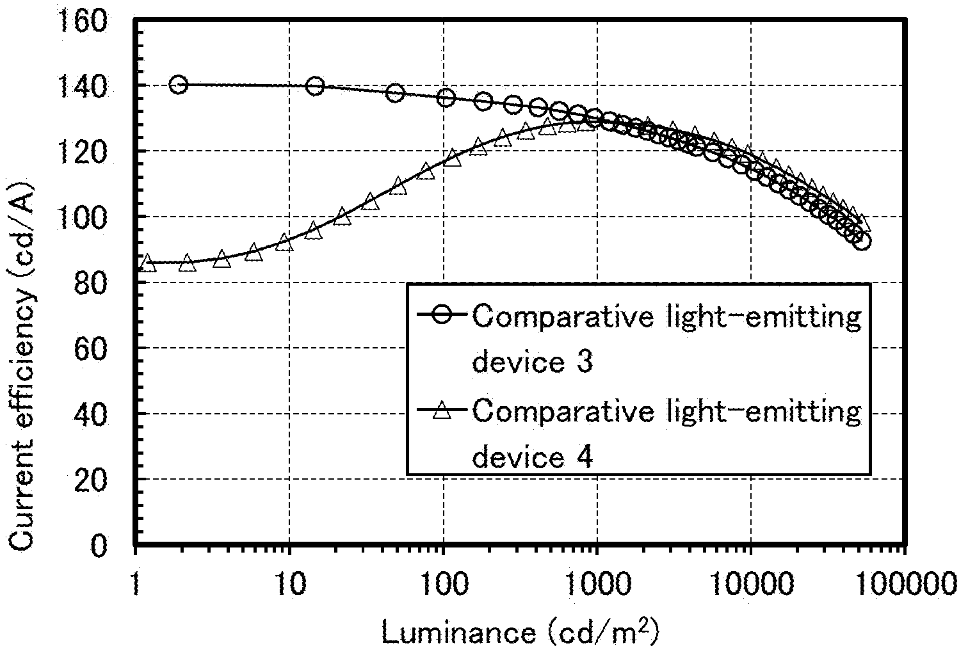
FIG. 25 shows current efficiency-luminance characteristics of Comparative light-emitting device 3 and Comparative light-emitting device 4.
Figure 26:
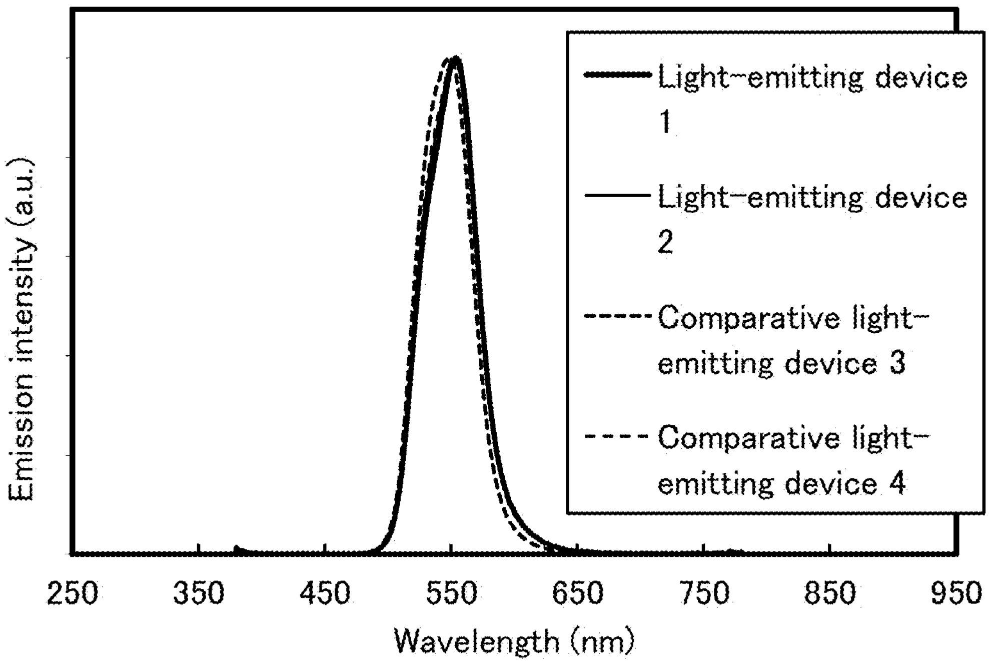
FIG. 26 shows the emission spectra of Light-emitting devices 1 and 2 and Comparative light-emitting devices 3 and 4.

FIG. 22 and FIG. 23 show the current-voltage characteristics and the current efficiency-luminance characteristics, respectively, of Light-emitting devices 1 and 2. FIG. 24 and FIG. 25 show the current-voltage characteristics and the current efficiency-luminance characteristics, respectively, of Comparative light-emitting devices 3 and 4. FIG. 26 shows the emission spectra of Light-emitting devices 1 and 2 and Comparative light-emitting devices 3 and 4. Table 5 shows the main characteristics of Light-emitting devices 1 and 2 and Comparative light-emitting devices 3 and 4 at a luminance of about 1000 cd/m$^2$. Luminance, CIE chromaticity, and emission spectra were measured at normal temperature with a spectroradiometer (SR-UL1R manufactured by TOPCON TECHNOHOUSE CORPORATION).

TABLE 5

| | Voltage (V) | Current (mA) | Current density (mA/cm$^2$) | Chromaticity (x, y) | Luminance (cd/m$^2$) | Current efficiency (cd/A) |
|---|---|---|---|---|---|---|
| Light-emitting device 1 | 4.0 | 0.027 | 0.67 | (0.33, 0.65) | 840 | 130 |
| Light-emitting device 2 | 4.0 | 0.026 | 0.66 | (0.33, 0.65) | 850 | 130 |
| Comparative light-emitting device 3 | 4.0 | 0.027 | 0.68 | (0.34, 0.65) | 850 | 130 |
| Comparative light-emitting device 4 | 3.1 | 0.030 | 0.74 | (0.31, 0.67) | 960 | 130 |

The results in FIG. 22 indicate that the thermal treatment hardly affects the current-voltage characteristics of the light-emitting device that has the structure of Light-emitting devices 1 and 2. By contrast, it is found that the thermal treatment changes the carrier-injection/transport properties and affects the current-voltage characteristics of the light-emitting device that has the structure of Comparative light-emitting devices 3 and 4 according to FIG. 24.

Furthermore, the results in FIG. 23 indicate that the thermal treatment hardly affects the current efficiency-luminance characteristics of the light-emitting device that has the structure of Light-emitting devices 1 and 2. By contrast, it is found that the thermal treatment changes the carrier balance to make carrier recombination more likely to occur and has the effect of increasing efficiency on the low luminance side of the current efficiency-luminance characteristics of the light-emitting device that has the structure of Comparative light-emitting devices 3 and 4 according to FIG. 25. The EL spectra in FIG. 26 also show that the light-emitting device that has the structure of Light-emitting devices 1 and 2 does not show any change in EL spectrum. By contrast, the EL spectra show that the light-emitting device that has the structure of Comparative light-emitting devices 3 and 4 changes in EL spectrum.

In general, a device that does not change in device properties by heating is desired. Thus, since the light-emitting device of one embodiment of the present invention does not exhibit any change in properties due to heating, the light-emitting device can be considered to have heat resistance to heat in the fabrication process.

This application is based on Japanese Patent Application Serial No. 2021-109302 filed with Japan Patent Office on Jun. 30, 2021, the entire contents of which are hereby incorporated by reference.

What is claimed is:

1. A light-emitting device comprising:

an EL layer between a first electrode and a second electrode provided over the first electrode, wherein the EL layer comprises at least a light-emitting layer, an electron-transport layer over the light-emitting layer, and a first electron-injection layer, wherein the electron-transport layer comprises a first electron-transport layer in contact with the light-emitting layer and a second electron-transport layer over and in contact with the first electron-transport layer, wherein a first insulating layer includes a part in contact with at least a side surface of the light-emitting layer, a side surface of the first electron-transport layer, and a side surface of the second electron-transport layer, wherein the first electron-injection layer is provided over the first insulating layer and the second electron-transport layer and under the second electrode, wherein the first electron-transport layer comprises a first heteroaromatic compound, wherein the second electron-transport layer comprises a second heteroaromatic compound that is different from the first heteroaromatic compound, wherein each of the first heteroaromatic compound and the second heteroaromatic compound is represented by any one of Structural Formulae (102) to (116), and (102)

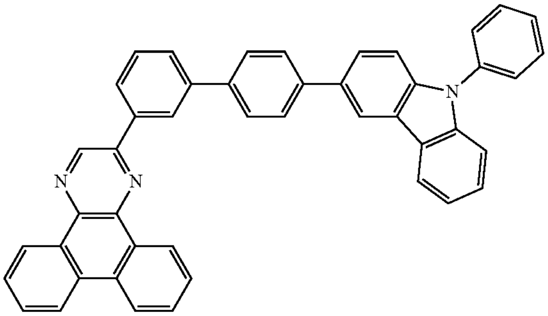

(103)

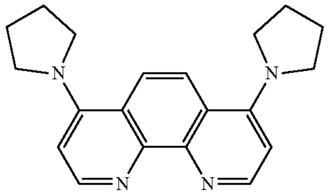

(104)

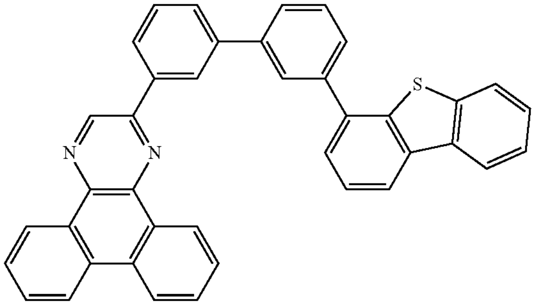

(105)

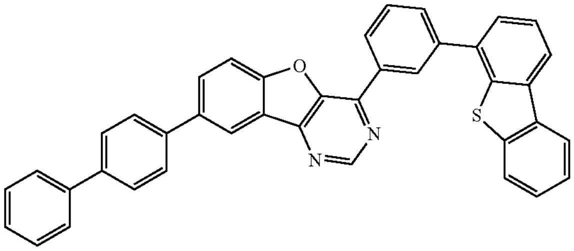

-continued (106)

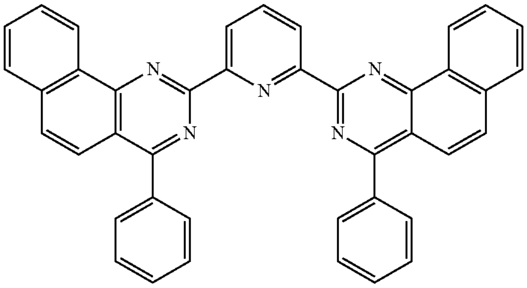

(107)

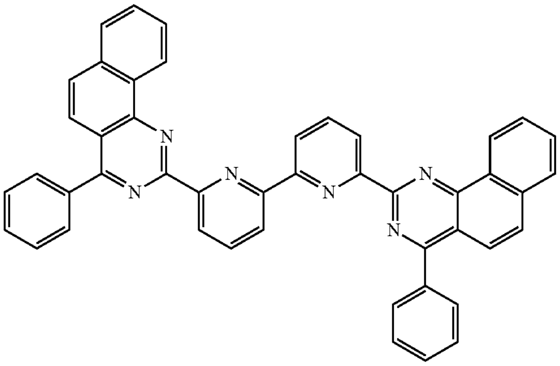

(108)

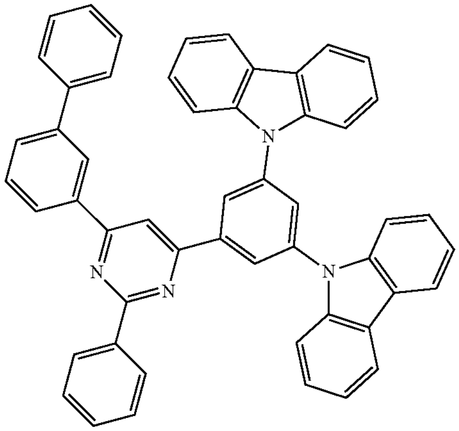

(109)

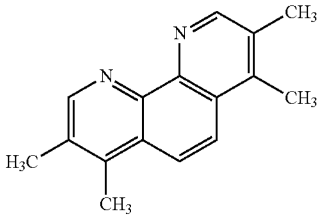

-continued (110)

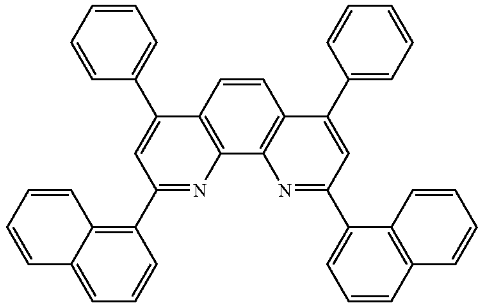

(111)

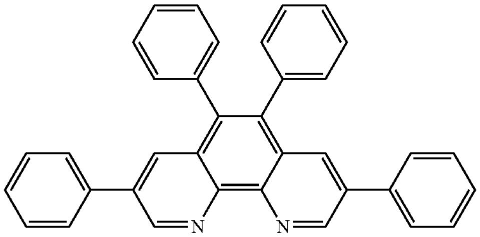

(112)

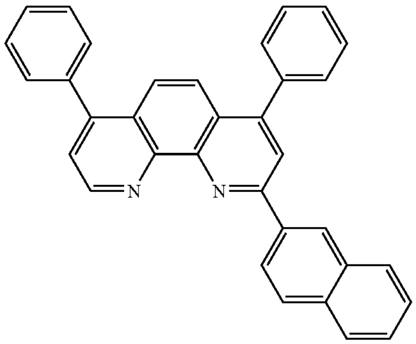

(113)

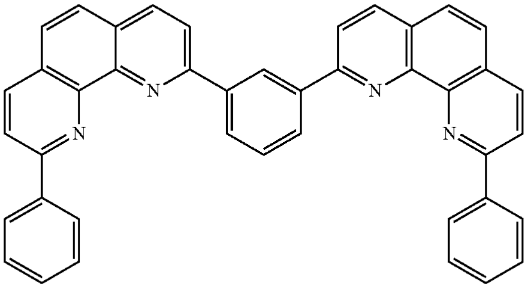

(114)

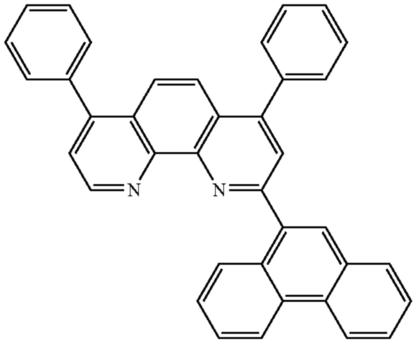

-continued (115)

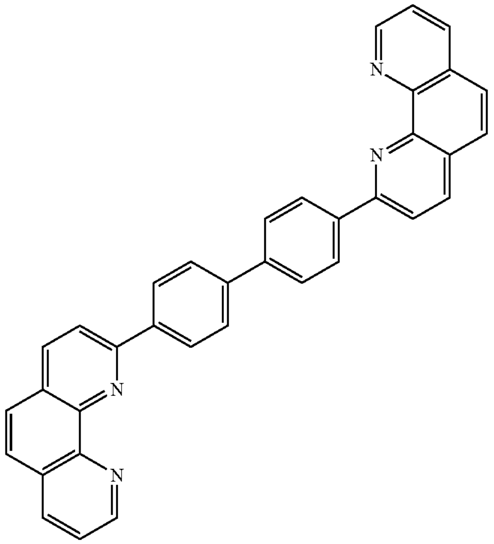

(116)

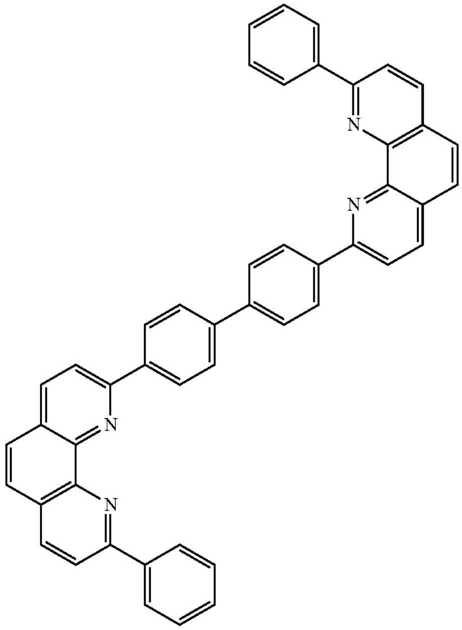

wherein a difference between a crystallization temperature (Tpc) of a powder state and a crystallization temperature (Ttc) of a thin film state of the first heteroaromatic compound is smaller than a difference between a crystallization temperature (Tpc) of a powder state and a crystallization temperature (Ttc) of a thin film state of the second heteroaromatic compound.

2. The light-emitting device according to claim 1, wherein the difference between the Tpc and the Ttc of the first heteroaromatic compound is less than or equal to 20° C., and wherein the difference between the Tpc and the Ttc of the second heteroaromatic compound is less than or equal to 100° C.

3. The light-emitting device according to claim 1, wherein the first electron-injection layer includes a first region covering at least the side surface of the light-emitting layer, the side surface of the first electron-transport layer, and the side surface of the second electron-transport layer, with the part of the first insulating layer provided therebetween.

4. The light-emitting device according to claim 1, wherein the first heteroaromatic compound is represented by Structural Formula (105), and (105)

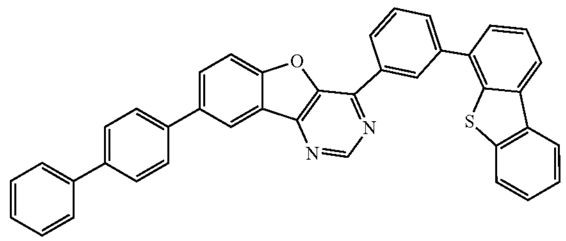

wherein the second heteroaromatic compound is represented by Structural Formula (107)

(107)

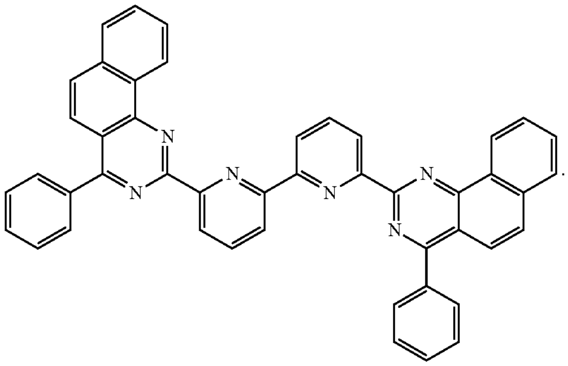

5. A light-emitting apparatus comprising the light-emitting device according to claim 1.

6. A light-emitting apparatus comprising:

a first light-emitting device and a second light-emitting device that are adjacent to each other, wherein the first light-emitting device comprises a second electrode over a first electrode with a first EL layer between the first electrode and the second electrode, wherein the first EL layer comprises at least a first light-emitting layer, a first electron-transport layer, a second electron-transport layer, and a first electron-injection layer, wherein the first electron-transport layer is over and in contact with the first light-emitting layer, wherein the second electron-transport layer is over and in contact with the first electron-transport layer, wherein a first insulating layer includes a part in contact with a side surface of the first light-emitting layer, a side surface of the first electron-transport layer, and a side surface of the second electron-transport layer, wherein the first electron-injection layer is over the second electron-transport layer and the first insulating layer, wherein the second light-emitting device comprises the second electrode over a third electrode with a second EL layer between the second electrode and the third electrode, wherein the second EL layer comprises at least a second light-emitting layer, a third electron-transport layer, a fourth electron-transport layer, and the first electron-injection layer, wherein the third electron-transport layer is over and in contact with the second light-emitting layer, wherein the fourth electron-transport layer is over and in contact with the third electron-transport layer, wherein a second insulating layer includes a first part in contact with a side surface of the second light-emitting layer, a side surface of the third electron-transport layer, and a side surface of the fourth electron-transport layer, wherein the first electron-injection layer is over the fourth electron-transport layer and the second insulating layer, wherein the first electron-transport layer comprises a first heteroaromatic compound, wherein the second electron-transport layer comprises a second heteroaromatic compound that is different from the first heteroaromatic compound, wherein each of the first heteroaromatic compound and the second heteroaromatic compound is represented by any one of Structural Formulae (102) to (116), and (102)

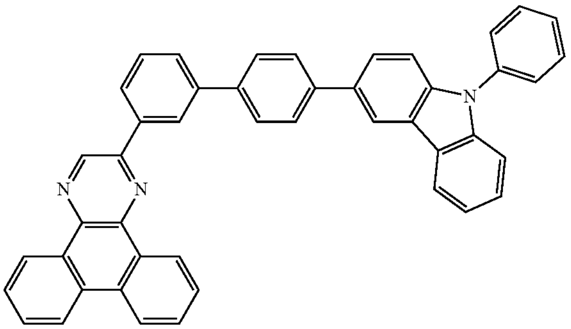

(103)

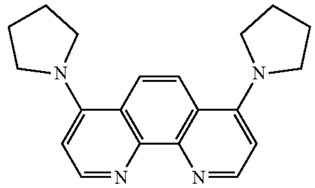

(104)

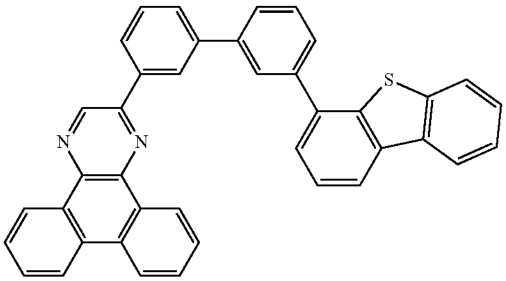

-continued
(105)
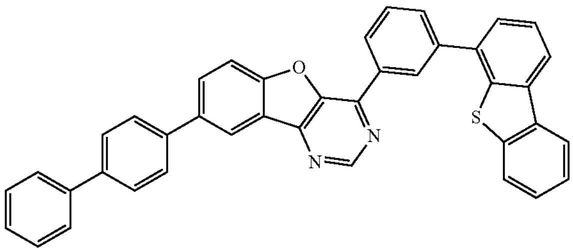
(106)
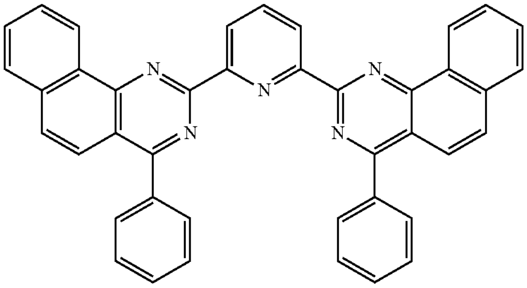
(107)
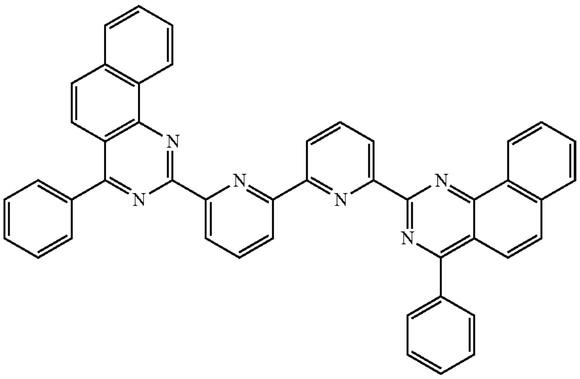
(108)
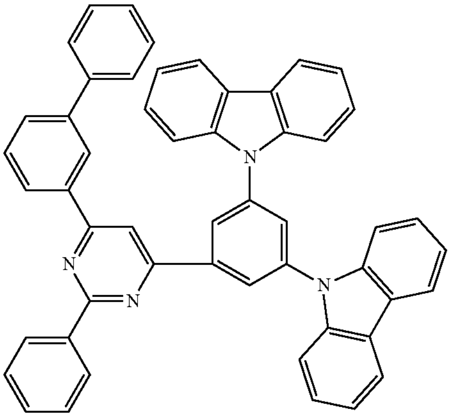
(109)
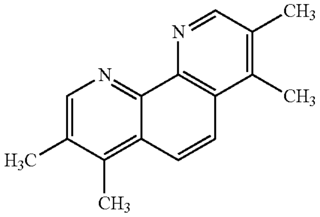
-continued
(110)
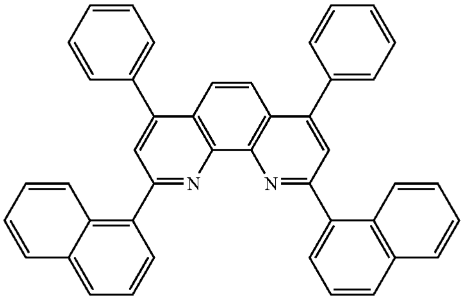
(111)
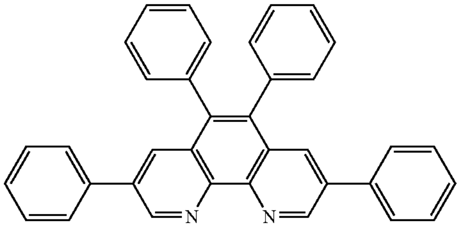
(112)
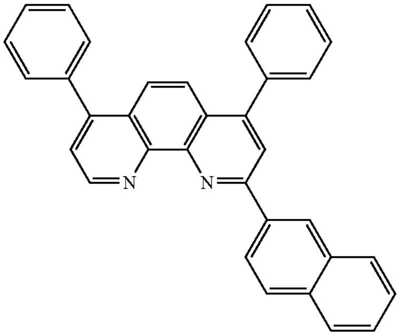
(113)
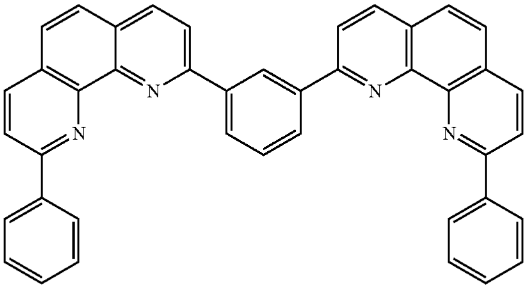
(114)
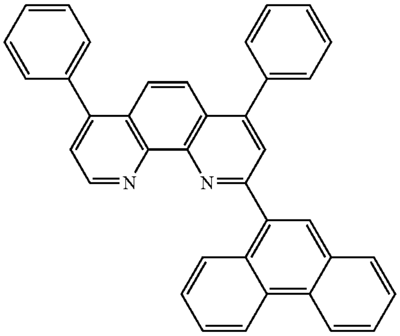

-continued (115)

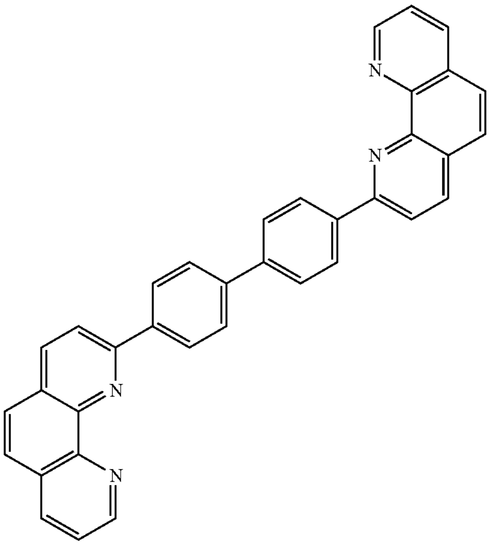

(116)

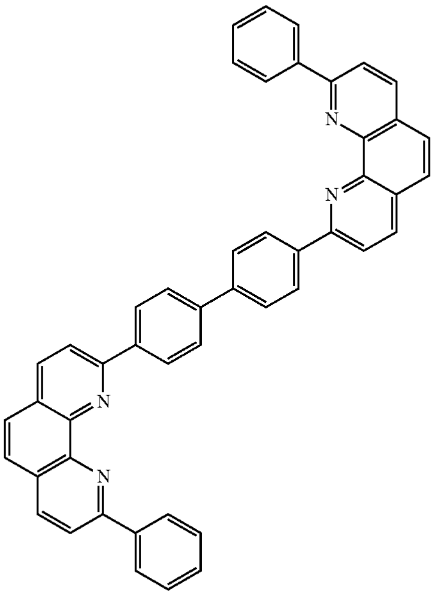

wherein a difference between a crystallization temperature (Tpc) of a powder state and a crystallization temperature (Ttc) of a thin film state of the first heteroaromatic compound is smaller than a difference between a crystallization temperature (Tpc) of a powder state and a crystallization temperature (Ttc) of a thin film state of the second heteroaromatic compound.

7. The light-emitting apparatus according to claim 6, wherein the difference between the Tpc and the Ttc of the first heteroaromatic compound is less than or equal to 20° C., and wherein the difference between the Tpc and the Ttc of the second heteroaromatic compound is less than or equal to 100° C.

8. The light-emitting apparatus according to claim 6, wherein the first electron-injection layer includes:

a first region covering the side surface of the first light-emitting layer, the side surface of the first electron-transport layer, and the side surface of the second electron-transport layer, with the part of the first insulating layer provided therebetween; and a second region covering the side surface of the second light-emitting layer, the side surface of the third electron-transport layer, and the side surface of the fourth electron-transport layer, with the first part of the second insulating layer provided therebetween.

9. The light-emitting apparatus according to claim 6, wherein the second insulating layer includes a second part in contact with a second side surface of the first light-emitting layer, a second side surface of the first electron-transport layer, and a second side surface of the second electron-transport layer.

10. The light-emitting device according to claim 6, wherein the first heteroaromatic compound is represented by Structural Formula (105), and (105)

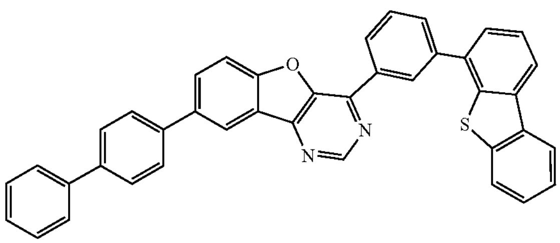

wherein the second heteroaromatic compound is represented by Structural Formula (107)

(107)

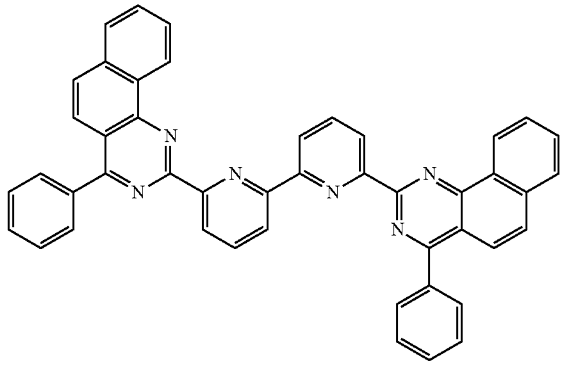

.

11. The light-emitting device according to claim 6, wherein the third electron-transport layer comprises the first heteroaromatic compound, and wherein the fourth electron-transport layer comprises the second heteroaromatic compound.

12. The light-emitting device according to claim 1, wherein each of the first heteroaromatic compound and the second heteroaromatic compound is represented by any one of Structural Formulae (102), (105), and (107), and (102)
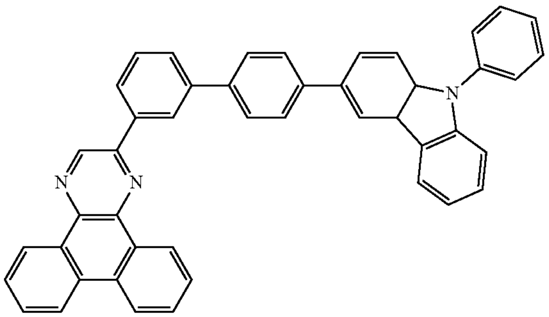
(105)
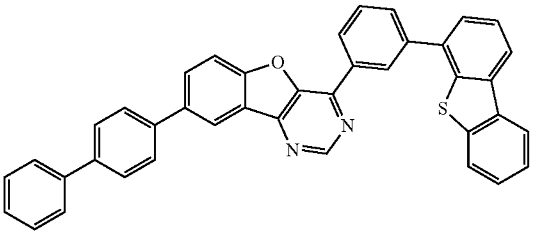
(107)
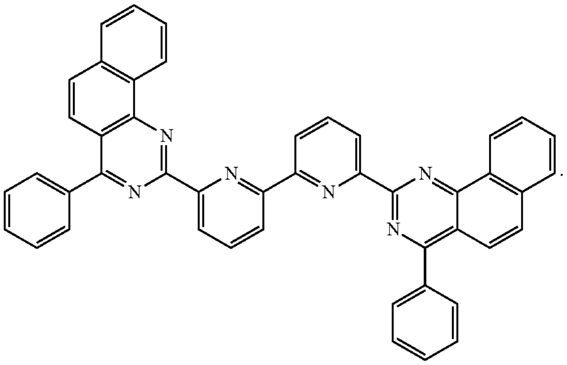
13. The light-emitting device according to claim 6,
wherein each of the first heteroaromatic compound and the second heteroaromatic compound is represented by any one of Structural Formulae (102), (105), and (107), and
(102)
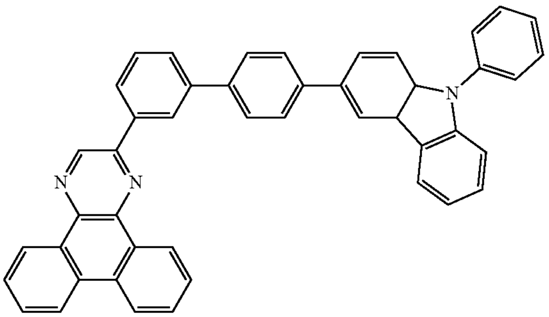
(105)
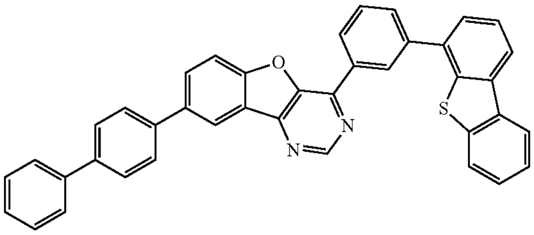
(107)
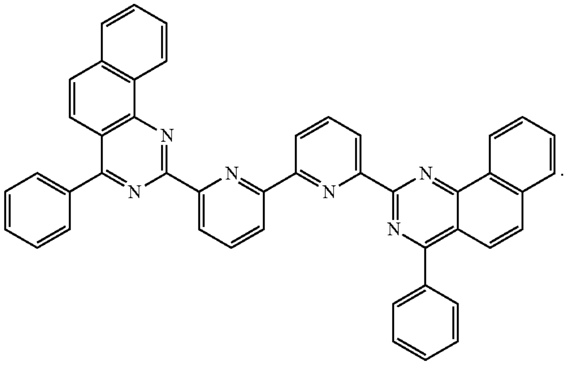
* * * * *